(12) United States Patent
Watanabe et al.

(10) Patent No.: US 6,498,159 B1
(45) Date of Patent: Dec. 24, 2002

(54) PHTHALAZINE DERIVATIVES AND REMEDIES FOR ERECTILE DYSFUNCTION

(75) Inventors: Nobuhisa Watanabe, Ibaraki (JP); Norio Karibe, Saitama (JP); Kazuki Miyazaki, Ibaraki (JP); Fumihiro Ozaki, Ibaraki (JP); Atsushi Kamada, Ibaraki (JP); Shuhei Miyazawa, Ibaraki (JP); Yoshimitsu Naoe, Ibaraki (JP); Toshihiko Kaneko, Ibaraki (JP); Itaru Tsukada, Ibaraki (JP); Tadashi Nagakura, Ibaraki (JP); Hiroki Ishihara, Ibaraki (JP); Kohtarou Kodama, Ibaraki (JP); Hideyuki Adachi, Ibaraki (JP)

(73) Assignee: Eisai Co., Ltd., Tokyo (JP)

( * ) Notice: Subject to any disclaimer, the term of this patent is extended or adjusted under 35 U.S.C. 154(b) by 0 days.

(21) Appl. No.: 09/508,197

(22) PCT Filed: Feb. 17, 1999

(86) PCT No.: PCT/JP99/00688

§ 371 (c)(1),
(2), (4) Date: Mar. 8, 2000

(87) PCT Pub. No.: WO99/42452

PCT Pub. Date: Aug. 26, 1999

(30) Foreign Application Priority Data

Feb. 19, 1998 (JP) ............................................. 10-037020
Nov. 10, 1998 (JP) ............................................. 10-319540

(51) Int. Cl.[7] .................. A61K 31/502; C07D 401/04; C07D 491/107; C07D 498/08
(52) U.S. Cl. ...................... 514/248; 544/230; 544/237; 544/62; 514/228.2
(58) Field of Search ............................ 544/237; 514/248

(56) References Cited

U.S. PATENT DOCUMENTS 5,849,741 A * 12/1998 Watanabe et al. ........... 514/248

FOREIGN PATENT DOCUMENTS

| HU | 200762 | 6/1989 |
| JP | A6135938 | 5/1997 |
| WO | A105176 | 2/1996 |
| WO | A107430 | 2/1998 |

OTHER PUBLICATIONS

Taher et al, Medline Abstract fu *World Journal of Urology* 15 p. 32–35, 1997.*
Bowman et al., *Br. J. Pharmac.*, vol. 81, pp. 665–674 (1984).
Bush et al., *Int. J. Impotence Res.*, vol. 4, pp. 85–93 (1992).
Bush et al., *The Journal of Urology*, vol. 147, pp. 1650–1655 (1992).
Rajeer et al., *The New England Journal of Medicine*, vol. 326, No. 2, pp. 90–94 (Jan. 1992).

* cited by examiner

*Primary Examiner*—Emily Bernhardt
(74) *Attorney, Agent, or Firm*—Birch, Stewart, Kolasch & Birch, LLP

(57) ABSTRACT

The present invention provides a phthalazine compound as a therapeutic agent for erectile dysfunction represented by the following formula, a pharmacologically acceptable salt thereof or a hydrate thereof:

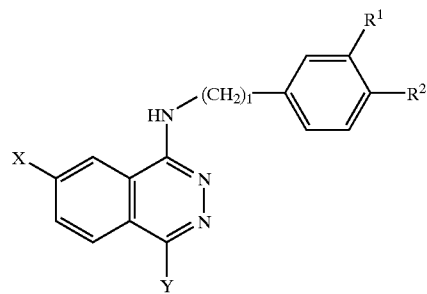

wherein $R^1$ and $R^2$ are the same as or different from each other and represent a halogen atom, a C1 to C4 alkyl group which may be substituted with a halogen atom, a C1 to C4 alkoxy group which may be substituted with a halogen atom or a cyano group; X represents a cyano group, a nitro group, a halogen atom, a hydroxyimino group which may be substituted or a heteroaryl group which may be substituted; Y represents a heteroaryl group, an aryl group which may be substituted, an alkynyl group which may substituted, an alkenyl group, an alkyl group, an optionally substituted saturated or unsaturated 4- to 8-membered amine ring, and the cyclic amine compound is a monocyclic compound, bicyclic compound or a spiro compound; l is an integer of 1 to 3; provided that the case where l is 1 or 2, X is a cyano group, a nitro group or a chlorine atom, $R^1$ is a chlorine atom, $R^2$ is a methoxy group and Y is a 5- or 6-membered amine ring substituted with a hydroxyl group is excluded.

20 Claims, No Drawings

PHTHALAZINE DERIVATIVES AND REMEDIES FOR ERECTILE DYSFUNCTION

This application is the national phase under 35 U.S.C. § 371 of PCT International Application No. PCT/JP99/00688 which has an International filing date of Feb. 17, 1999, which designated the United States of America.

FIELD OF THE INVENTION

The present invention relates to phthalazine compounds. More specifically, it relates to prophylactic and therapeutic agents for male erectile dysfunction, and prophylactic and therapeutic agents for female sexual dysfunction or dysmenorrhea.

PRIOR ART

It is said that the number of latent patients with erectile dysfunction amounts to about 3,000,000 in Japan. In U.S.A., it is reported that the number of patients with erectile dysfunction reaches 20,000,000 and 15% of males in the fifties and about ⅓ of those in the sixties suffer from this disease. In this aging society, sexual intercourse is regarded as a pleasant and emotional behavior. With the needs for the improved quality of life, it is anticipated that erectile dysfunction will raise not only a medical problem but also a social problem in future. This disease is classified into organic impotence caused by disorders in the nerves, blood vessels or muscles in the penis per se or sexual hormones and functional (psychic) impotence caused by mental or psychologic troubles. There are three factors necessary for erection, i.e., an increase in the penile arterial blood flow, the regulation of blood leakage from the penile veins, and the relaxation of the cavernous tissue. Erectile dysfunction arises when at least one of these conditions is inhibited.

The urological treatments for erectile dysfunction effected today involve drug therapy and operative penile prosthesis with the use of penile prosthetic appliances.

As the drug therapy, it is possible to inject papaverine hydrochloride or prostaglandin E1 into the penile cavernous tissue. However, this treatment is scarcely performed today, since it is not allowed in Japan that a patient gives an injection to himself and it is impossible in practice to go for a doctor every time he has coitus. In addition, the injection of papaverine hydrochloride would cause, though exceptionally, a painful symptom called priapism. Thus, the treatments with the existing drugs are not practically usable. Accordingly, it has been urgently desired to develop a drug therapy therefor which is clinically efficacious in practice.

In 1984, Bowman and Drummond reported that a selective cyclic GMP phosphodiesterase inhibitor M&B22948 (zaprinast) increased cyclic GMP in the tissue and relaxed the bovine retractor penis muscle (Cyclic GMP mediates neurogenic relaxation in the bovine retractor penis muscle, Br. J. Pharmacol., 81, 665–674, 1984). Subsequently, other workers have reported one after another the relaxation of the penis cavernosum by increasing cyclic GMP in the tissue (Int. J. Impotence Res., 4, 85–93, 1992; J. Urol., 147, 1650–1655, 1992; and N. Engl. J. Med., 326, 90–94, 1992). However, none of the compounds employed in these studies can be satisfactorily employed clinically due to poor efficacy, etc.

An inhibitor of phosphodiesterase type V is also effective against female sexual dysfunction.

Phthalazine compounds having an inhibitory action on phosphodiesterase type V are disclosed in WO9605176 (JP-A 8-225541), but there is neither disclosure on spiro compounds containing nitrogen atoms, or bicyclic and 6-memberred heterocyclic compounds thereof nor description on prevention and therapy for erectile dysfunction.

DISCLOSURE OF THE INVENTION

The present inventors have conducted various studies and consequently found that phthalazine compounds represented by the formula (I) show a high selectivity for phosphodiesterase type V which is an enzyme degrading cyclic GMP, and a potent inhibitory effect thereon, and exhibit a strong relaxing action on the penile cavernosum, with the increase in bioavailability and have high safety, thus completed the present invention.

The present invention relates to phthalazine compounds not specifically disclosed in JP-A 8-225541, to phthalazine compounds not suggested therein, and further to a process for producing some of the compounds.

It relates to a phthalazine compound represented by the formula (I), a pharmacologically acceptable salt thereof or a hydrate thereof:

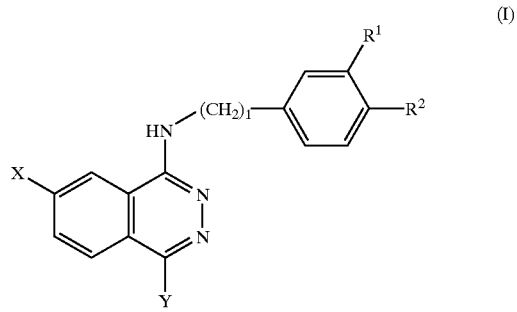

(I)

wherein $R^1$ and $R^2$ are the same as or different from each other and represent a halogen atom, a C1 to C4 alkyl group which may be substituted with a halogen atom, a hydroxyl group, a C1 to C4 alkoxy group which may be substituted with a halogen atom or a cyano group;

X represents a cyano group, a nitro group, a halogen atom, a thiocarbamoyl group, a hydroxyimino group which may be substituted with a C1 to C4 alkyl group, an aryl C1 to C4 alkyl group or a carboxy C1 to C4 alkyl group, or a heteroaryl group which may be substituted with 1 to 3 substituent groups selected from the following substituent groups A;

Y represents:
 i) a group represented by the formula (II):

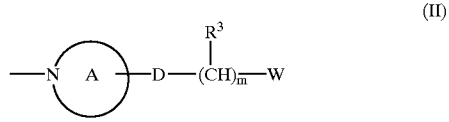

(II)

wherein ring A represents a 4- to 8-memberred amine ring which may be substituted with a methyl group and may have a double bond; D represents a single bond or an oxygen atom; R³ represents a hydrogen atom, a C1 to C4 alkyl group or a halogen atom; m represents an integer of 0 to 3; W represents an amino group, a hydroxyl group, a cyano group, a carboxyl group which may be protected, or a C1 to C4 alkoxy group;

ii) a group represented by the formula (III):

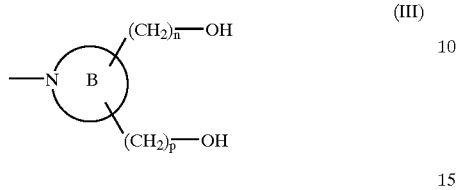

(III)

wherein ring B represents a 4- to 8-memberred amine ring which may have a double bond; and n and p are the same as or different from each other and represent an integer of 0 to 3;

iii) a group represented by the formula (IV):

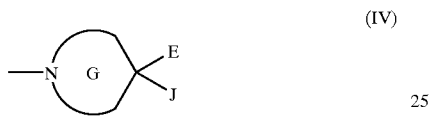

(IV)

wherein ring G represents a 4- to 8-memberred amine ring which may have a double bond, E represents a hydroxyl group, a halogen atom, a C1 to C4 alkyl group or a C1 to C4 alkoxy group, J is the formula —(CHR⁴)q—Q (wherein R⁴ represents a hydrogen atom or a C1 to C4 alkyl group, Q represents a hydroxyl group, a halogen atom, a carboxyl group which may have a protective group, a carbamoyl group or an azolyl group not containing a heteroatom other than a nitrogen atom, q is an integer of 0 or 1 to 4), or E and J may form a 3- to 6-memberred ring together with the carbon atom to which they are bound, and the ring optionally having a heteroatom and optionally having a substituent group;

iv) a group represented by the formula (V):

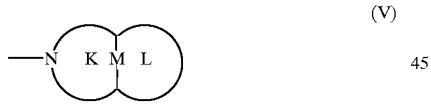

(V)

wherein M represents a single bond or a C1 to C4 alkylene group which may be substituted with a hydroxyl group, carboxyl group, a C1 to C4 alkyl group or a C1 to C4 alkoxy group, ring K represents a 5- to 8-memberred amine ring formed together with M, and ring L represents a 5- to 8-memberred alkyl ring which may have a substituent group and may have an oxygen atom;

v) a group represented by the formula (VI):

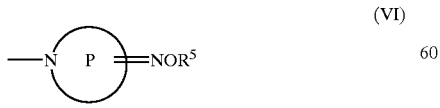

(VI)

wherein ring P represents a 5- to 7-memberred amine ring, and R⁵ represents a hydrogen atom or a C1 to C4 alkyl group which may be substituted with a halogen atom, a hydroxyl group or a carboxyl group;

vi) an alkynyl group, an alkenyl group or an alkyl group all of which may have a substituent group;

vii) a phenyl group which may be substituted with 1 to 3 substituent groups selected from the following substituent group A; or viii) a pyridyl group, a pyrimidyl group, a thienyl group, a thiazolyl group or a furyl group all of which may be substituted with 1 to 3 substituent groups selected from the following substituent group A; (substituent group A) a C1 to C4 alkyl group which may be substituted with a halogen atom, a cyano group, a nitro group or a hydroxyl group; a C1 to C4 alkoxy group which may be substituted with a halogen atom, a cyano group, a nitro group or a hydroxyl group; a cyano group; a nitro group; a carboxyl group which may have a protective group; a hydroxyl group which may have a protective group; a carbamoyl group which may be substituted with a lower alkyl group; a halogen atom; and an amino group which may be substituted with a C1 to C4 acyl group, a C1 to C4 alkylsulfonyl group or an arylsulfonyl group which may have a substituent group; l is an integer of 1 to 3;

provided that the following cases are excluded:
the case where l is 1 or 2, X is a cyano group, a nitro group or a chlorine atom, R¹ is a chlorine atom, R² is a methoxy group, ring A is a 5- or 6-memberred amine ring, D is a single bond, m is 0, and W is a carboxyl group which may have a protective group or a C1 to C4 alkoxy group; the case where l is 1, R¹ is a chlorine atom, R² is a methoxy group, ring A is a saturated 5- or 6-memberred amine ring, D is a single bond, and W is a hydroxyl group; the case where l is 1, ring B is a 5- or 6-memberred amine ring, and both n and p are 0; the case where l is 1, E and Q are hydroxyl groups, and q is 0; and the case where l is 1, X is a chlorine atom and Y is a phenyl group substituted with a methoxy group.

Further, the present inventors have found out that compounds of the following formula (VII) also exhibit a strong relaxing action on the penile cavernosum with the increase in bioavailability, and have high safety. Thus, they have completed the present invention.

A therapeutic agent for erectile dysfunction, which comprises a phthalazine compound represented by the formula (VII), a pharmacologically acceptable salt or a hydrate thereof as an active ingredient:

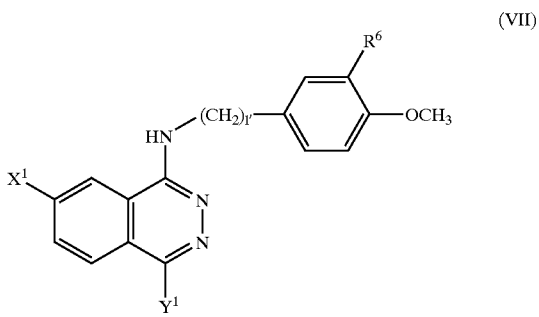

(VII)

wherein l' is an integer of 1 to 3; $R^6$ represents a halogen atom, a C1 to C4 alkyl group which may be substituted with a halogen atom or a cyano group;

$X^1$ represents a cyano group, a nitro group or a halogen atom;

$Y^1$ represents:

i) a group represented by formula (VIII):

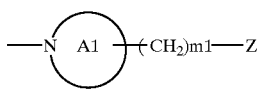

(VIII)

wherein ring A1 represents a 5- or 6-membered amine ring; m1 is an integer of 0 or 1 to 3; and Z represents an amino group, a hydroxyl group which may have a protective group, a carboxyl group which may have a protective group, a C1 to C4 alkoxy group or a cyano group;

ii) a group represented by formula (IX):

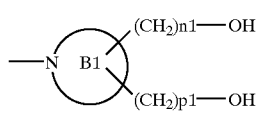

(IX)

wherein ring B1 represents a 5- or 6-membered amine ring, n1 and p1 are integers of 0 or 1 to 3;

iii) a thiomorpholino group wherein its morpholino group or its sulfur atom may be oxidized;

iv) a phenyl group which may be substituted with 1 to 3 substituent groups selected from the following substituent group A1;

v) a heteroaryl group which is a pyridyl group, a pyrimidyl group, a thienyl group or a furyl group all of which may be substituted with 1 to 3 substituent groups selected from the following substituent group A1; or vi) a group of formula $-N(R^7)-(CH_2)_s$-Het, wherein $R^7$ represents a lower alkyl group, Het represents a pyridyl group or a pyrimidyl group all of which may be substituted with 1 to 3 substituent groups selected from the following substituent group A1, and s is an integer of 0 or 1 to 3;

(substituent group A1) a lower alkyl group substituted with a halogen atom, a cyano group, a nitro group, or a hydroxyl group, a lower alkoxy group which may be substituted with a halogen atom, cyano group, nitro group, or a hydroxyl group; a cyano group; a nitro group; a carboxyl group which may have a protective group; a hydroxyl group which may have a protective group; a carbamoyl group which may be substituted with a lower alkyl group; a halogen atom; and a phenyl group which may be substituted with an alkyl group, an alkoxy group, a halogen atom or an amino group.

The present invention provides a process for producing a compound represented by the formula (XI):

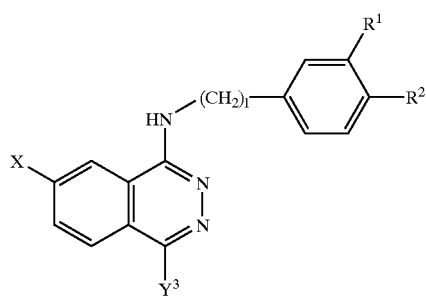

(XI)

(wherein X, $Y^3$, $R^1$, $R^2$ and l have the same meanings as defined above), which comprises the step of reacting a compound represented by the formula (X):

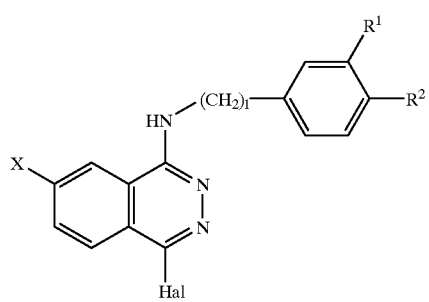

(X)

(wherein Hal represents a halogen atom; and $R^1$, $R^2$, l and X have the same meanings as defined above) with a compound of the formula $Y^3-B(OH)_2$ (wherein $Y^3$ represents a phenyl group, a pyridyl group, a pyrimidyl group, a thienyl group or a furyl group all of which may have a substituent group selected from the above substituent group A1).

The present invention provides a prophylactic and therapeutic agent for erectile dysfunction, which comprises the phthalazine compound represented by the above formula (I), a pharmacologically acceptable salt thereof or a hydrate thereof as an active ingredient. Further, it provides a prophylactic and therapeutic agent for female sexual dysfunction or dysmenorrhea, which comprises the phthalazine compound represented by the above formula (I) or (VII), a pharmacologically acceptable salt thereof or a hydrate thereof as an active ingredient.

The present invention provides a pharmaceutical composition comprising a pharmacologically or clinically effective amount of the phthalazine compound represented by the above formula (I) or (XI), a pharmacologically acceptable salt thereof or a hydrate thereof, and pharmacologically acceptable carriers.

The present invention provides a method or use for preventing or treating erectile dysfunction, female sexual dysfunction or dysmenorrhea, which comprises the step of administering a pharmacologically or clinically effective amount of the phthalazine compound represented by the above formula (I) or (VII), a pharmacologically acceptable salt thereof or a hydrate thereof to a patient suffering from erectile dysfunction, female sexual dysfunction or dysmenorrhea.

In the definitions set forth in the present invention, the halogen atoms defined in X, $R^1$, $R^2$, $R^3$, $R^4$, $R^5$, E, Q, substituent groups A and A1 mean a fluorine atom, a chlorine atom, a bromine atom and an iodine atom.

The C1 to C4 alkyl groups defined in $R^1$, $R^2$, $R^3$, $R^4$, $R^5$, $R^6$, $R^7$, substituent groups A and A1 mean linear or branched alkyl groups having 1 to 4 carbon atoms, such as methyl, ethyl, n-propyl, isopropyl, n-butyl, isobutyl, 1-methylpropyl and tert-butyl. The C1 to C4 alkoxy groups defined in $R^1$, $R^2$ and substituent groups A and A1 mean groups derived from the above-mentioned C1 to C4 alkyl groups, and such groups include, for example, a methoxy group, an ethoxy group, a propoxy group etc.

The protective groups in the carboxyl group which may have a protective group defined in Q, W, substituent groups A and A1 mean, for example, lower alkyl groups such as methyl group, ethyl group and tert-butyl group; lower alkyl groups substituted with a phenyl group which may have a substituent group such as p-methoxybenzyl, p-nitrobenzyl, 3,4-dimethoxybenzyl, diphenylmethyl, trityl and phenethyl; halogenated lower alkyl groups such as 2,2,2-trichloroethyl and 2-iodoethyl; lower alkanoyloxy lower alkyl groups such as pivaloyloxymethyl, acetoxymethyl, propionyloxymethyl, butylyloxymethyl, valelyloxymethyl, 1-acetoxyethyl, 2-acetoxyethyl, 1-pivaloyloxyethyl and 2-pivaloyloxyethyl; higher alkanoyloxy lower alkyl groups such as palmitoyloxyethyl, heptadecanoyloxymethyl and 1-palmitoyloxyethyl; lower alkoxycarbonyloxy lower alkyl groups such as methoxycarbonyloxymethyl, 1-butoxycarbonyloxyethyl and 1-(isopropoxycarbonyloxy)ethyl; carboxy lower alkyl groups such as carboxymethyl and 2-carboxyethyl; heteroaryl groups such as 3-phthalidyl; benzoyloxy lower alkyl groups optionally having a substituent group such as 4-glycyloxybenzoyloxymethyl; (substituted dioxolene) lower alkyl groups such as (5-methyl-2-oxo-1,3-dioxolene-4-yl)methyl; cycloalkyl-substituted lower alkanoyloxy lower alkyl groups such as 1-cyclohexylacetyloxyethyl; and cycloalkyloxycarbonyloxy lower alkyl groups such as 1-cyclohexyloxycarbonyloxyethyl. In short, any group which can be degraded by any means in vivo to form a carboxylic acid can serve as a protective group for the carboxyl group.

The protective groups in the hydroxyl group which may have a protective group defined in substituent groups A and A1 mean, for example, acyl groups such as formyl group, acetyl group and benzoyl group; and lower alkoxymethyl groups such as 2-methoxyethoxymethyl group. In short, any group which can be degraded by any means in vivo to form a hydroxyl group can serve as a protective group for the hydroxyl group.

The azolyl group not containing a heteroatom other than a nitrogen atom defined in Q means groups derived from pyrrole, pyrazole, imidazole, triazole, tetrazole, indazole, benzimidazole and benzotriazol.

In the formula (IV), a compound produced from a ring formed by E and J together with the carbon atom to which they are bound and a ring G is a spiro compound. The ring formed by E and J together with the carbon atom to which they are bound includes cyclobutane, cyclopentane, cyclohexane, oxirane, tetrahydrofuran, tetrahydropyran, butyrolactone and butyrolactam. Further, a substituent group on these rings includes a hydroxyl group, the carboxyl group which may have the above protective group, a C1 to C4 alkyl group which may be substituted with a hydroxyl group such as a hydroxymethyl group and hydroxyethyl group, a carbonyl group and a halogen atom such as fluorine atom and chlorine atom.

In the formula (V), a bicyclo ring which, when M is a C1 to C4 alkylene group, is formed from rings K and L is meant to be a cross-linked ring. A substituent group on ring L includes a hydroxyl group, a carboxy group which may have the above protective group, a C1 to C4 alkyl group which may be substituted with a hydroxyl group such as a hydroxymethyl group and a hydroxyethyl group, a C1 to C4 alkyl group carbonyl group which may be substituted with a carboxyl group such as a carboxymethyl group and carboxyethyl group, a halogen atom such as a fluorine atom and a chlorine atom, a vinyl group, etc.

The substituent groups in the alkynyl group, alkenyl group or alkyl group wherein Y may have a substituent group include C1 to C4 alkyl groups such as methyl group, ethyl group, propyl group, isopropyl group, butyl group, isobutyl group, sec-butyl group and tert-butyl group; groups derived from cycloalkanes such as cyclopropane, cyclobutane, cyclopentane and cyclohexane; C1 to C4 alkoxy groups derived from the above C1 to C4 alkyl groups, such as a methoxy group, ethoxy group and propoxy group etc.; a hydroxyl group; an amino group which may be substituted with a C1 to C4 alkyl group; cyclic amines which maybe substituted with a hydroxy group, for example, aziridine, azetidine, pyrrolidine and piperidine; hydroxy C1 to C4 alkyl groups; hydroxy C1 to C4 alkoxy groups; carboxyalkoxy groups; and halogen atoms such as fluorine atom and chlorine atom.

In X, the heteroaryl group includes groups derived from pyrrole, pyrazole, imidazole, triazole, tetrazole, indazole, benzimidazole, benzotriazole, thiazole, isothiazole, thiadiazole, benzothiadiazole, pyridine, pyrimidine, triazine, quinoline, isoquinoline, naphthylidine, phthalazine, etc.

In the present invention, the pharmacologically acceptable salt includes, for example, inorganic acid salts such as hydrochloride, sulfate, hydrobromate and phosphate, and organic acid salts such as formate, acetate, maleate, fumarate, tartrate, methanesulfonate, benzenesulfonate, and toluenesulfonate.

It goes without saying that in the case of compounds having an asymmetric atom in the present invention, their optically active compounds are included within the scope of the present invention.

Further, compounds which are metabolized in vivo to form the compounds of the present invention and compounds formed through metabolism from the compounds of the present invention, are also included within the scope of the present invention.

Because of being excellent in oral absorbability and ling-lasting action, these phthalazine compounds, pharmacologically acceptable salts thereof or hydrates thereof can be percutaneously, intravenously or orally administered for treatment without resort to injection directly into the penile cavernosum or the pudenda, which makes them favorable as prophylactic and therapeutic agents for erectile dysfunction and as prophylactic and therapeutic agents for female sexual dysfunction or dysmenorrhea.

Although the administration dose of the compounds of the present invention is not particularly limited, generally, they are administered to an adult in a dose of from 5 µg to 100 mg, preferably from 10 to 1,000 µg, in the case of intravenous administration, or in a dose of from 1 to 1,000 mg, preferably from 5 to 100 mg, in the case of oral administration.

PRODUCTION PROCESS 1

Production processes for producing analogous compounds of the phthalazine compounds of the present invention or pharmacologically acceptable salts thereof are described in WO9605176 (JP-A 8-225541), and the phthalazine compounds of the present invention are produced in the same manner as follows:

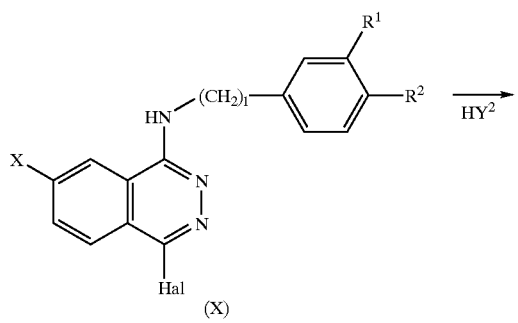

(X)

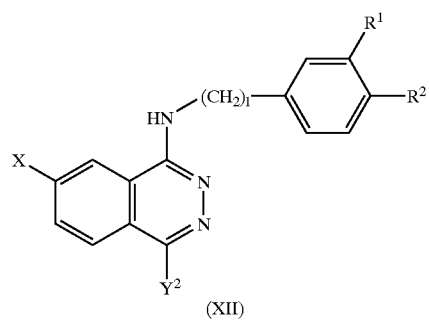

(XII)

wherein, $Y^2$ is:

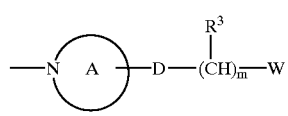

i)

wherein ring A, D, $R^3$, m and W have the same meanings as defined above;

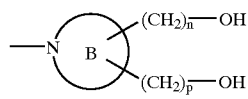

ii)

wherein ring B, n and p have the same meanings as defined above;

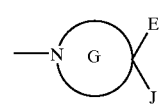

iii)

wherein ring G, E and J have the same meanings as defined above;

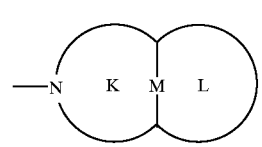

iv)

wherein ring K, ring L and M have the same meanings as defined above; and

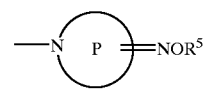

v)

wherein ring P and $R^5$ have the same meanings as defined above;

Hal is a halogen atom; and $R^1$, $R^2$, l and X have the same meanings as defined above.

It is the reaction, in which the compound represented by the formula (X) is reacted with $HY^2$ in a solvent to give the compound represented by the formula (XII). As the reaction solvent, N-methyl-2-pyrrolidine is preferable, but any solvent may be used so long as it is the one inert to the reaction. Preferable results may be obtained by using HY in excessive amount to the compound (X), or using an organic base such as diisopropyl ethylamine, or a salt such as potassium carbonate, sodium carbonate or sodium hydrogen carbonate. The reaction temperature is in the range of from room temperature to the boiling point of the solvent, preferably 100° C. or more.

Synthesis of $HY^2$ necessary for production of the compound wherein W is a cyano group, which is not described in WO9605176 (JP-A 8-225541), is conducted as follows:

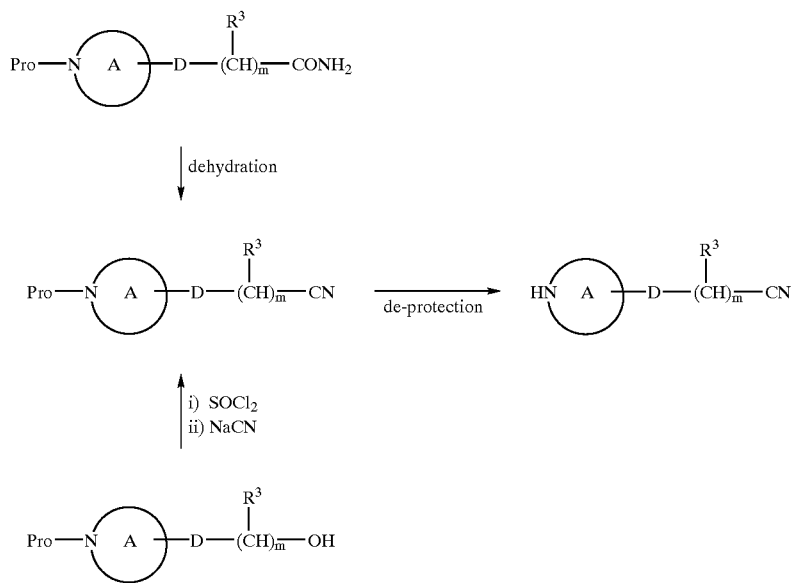

And, in the case where W defined above is an amino group, which is not specifically described in the above-mentioned publication, $HY^2$ wherein an amino group is protected is synthesized and then de-protected as follows:

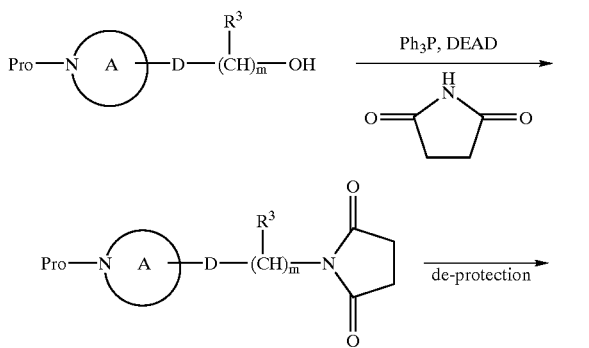

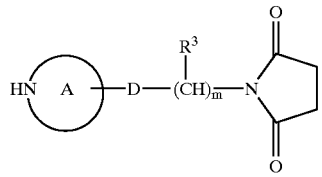

In the formula (I), $HY^2$ wherein Y is represented by the formulae (IV) and (V) can be produced by using a compound disclosed in WO9806720 or by using a process disclosed therein.

1) For example, some of the compounds represented by the formula (IV) are produced in the following process.

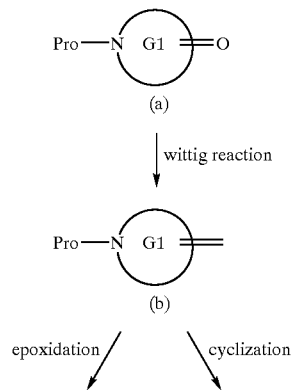

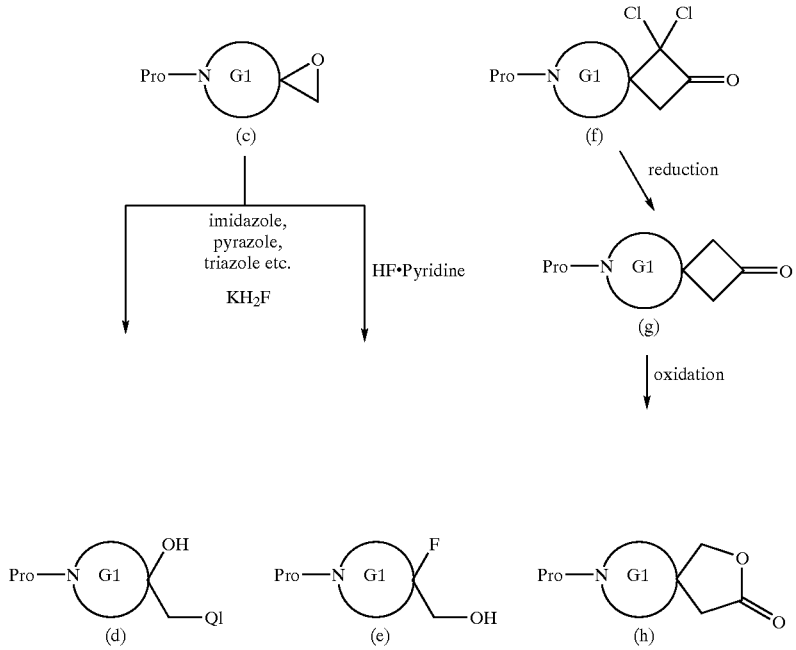

wherein G1 represents a 4- to 8-memberred ring; Q1 represents a pyrrolyl, a pyrazolyl, a imidazolyl, a triazolyl, a tetrazolyl, a indazolyl, a benzimidazolyl, a benzotriazolyl group or a fluorine atom; and Pro represents a protective group for the nitrogen atom.

In a solvent such as toluene, xylene or tetrahydrofuran methyltriphenylsulfonium bromide is treated with a base such as tert-butoxide potassium or butyl lithium, and reacted with the ketone compound represented by the formula (a), whereby the compound represented by the formula (b) can be obtained. The reaction temperature is preferably –78° C. to room temperature.

The compound (b) is reacted with trichloroacetyl chloride in a solvent such as diethyl ether, dimethoxyethane or tetrahydrofuran to give the dichlorocyclobutanone compound (f) (Alternatively, when it is reacted with diacetyl chloride, a monochloro-compound is obtained. The monochloro-compound can also be obtained by reacting with trichloroacetyl chloride, followed by treating with acetic acid.), and then the product is treated with a reducing agent such as zinc dust, whereby the cyclobutanone compound represented by the formula (g) can be obtained. The reaction temperature is preferably 10 to 50° C. When the compound (g) is treated with a peroxide such as 3-chloroperbenzoic acid in the presence of sodium hydrogen carbonate in a solvent such as dichloromethane, the lactone compound represented by the formula (h) can be obtained. The reaction temperature is preferably in the range of from room temperature to 40° C. When the compound (b) is treated with dichloroketene and diazomethane, a cyclopentanone compound in the formula (f) is obtained, and when the compound (g) is treated with diazomethane, a cyclopentanone compound in formula (g) is obtained. When the cyclopentanone compound is further treated with diazomethane, a cyclohexanone compound is obtained.

When the compound (b) is treated with a peracid such as magnesium phthalate monoperacid, the epoxide compound represented by the formula (c) is obtained. When the epoxide compound (c) is reacted with a sodium salt of azole containing nitrogen atoms only as hetero atoms in a solvent such as dimethylformamide, the corresponding compound represented by the formula (d) (Q1 is a 1-imidazolyl group, a 1-triazolyl group, etc.) is obtained. By treatment with potassium hydrogen fluoride at 100 to 150° C. in the presence of $Bu_4N \cdot H_2F_3$, a fluoromethyl compound as the compound represented by the formula (d) wherein Q1 is a fluorine atom is obtained.

On the other hand, the fluoro compound represented by the formula (e) is obtained by treating the compound (c) is treated with hydrogen fluoride pyridine in a solvent such as methylene chloride at –10 to 10° C.

2) Among the compounds represented by the formula (V), those wherein M is methylene substituted with a hydroxyl group are produced in, for example, the following process.

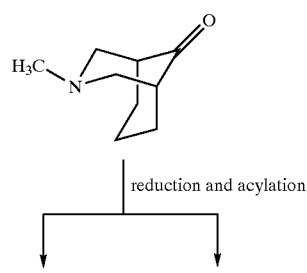

reduction and acylation

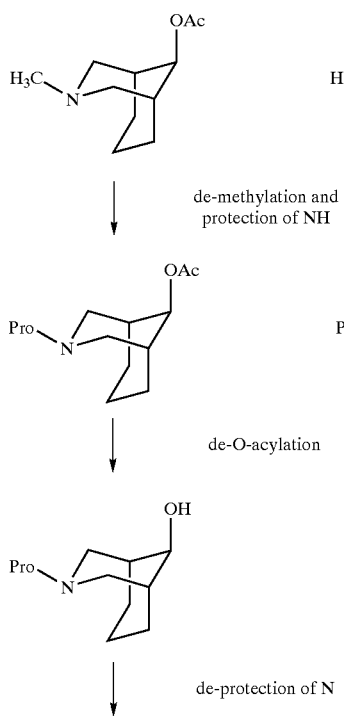
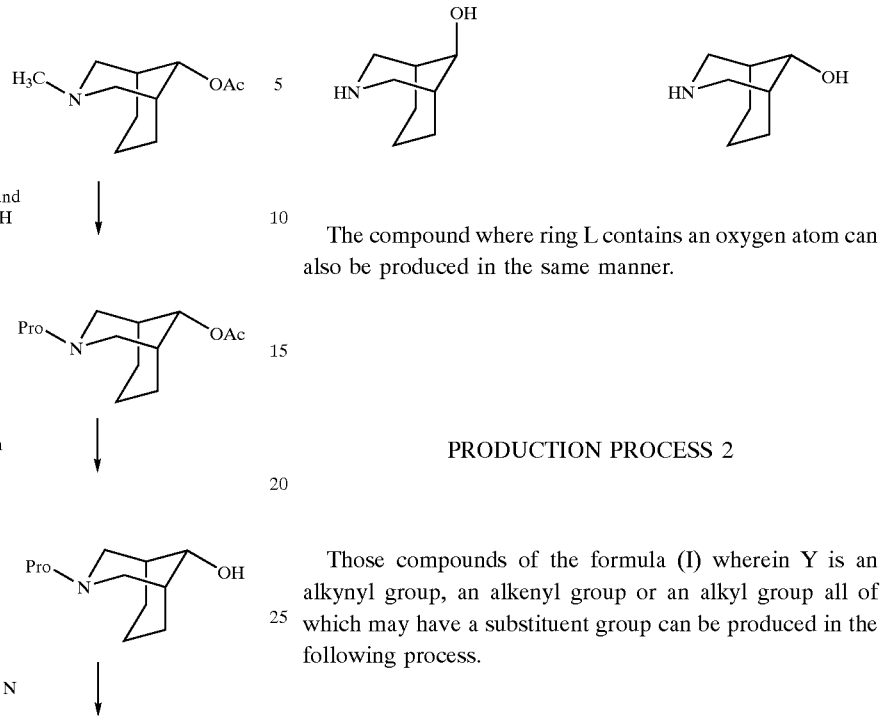
The compound where ring L contains an oxygen atom can also be produced in the same manner.
PRODUCTION PROCESS 2
Those compounds of the formula (I) wherein Y is an alkynyl group, an alkenyl group or an alkyl group all of which may have a substituent group can be produced in the following process.
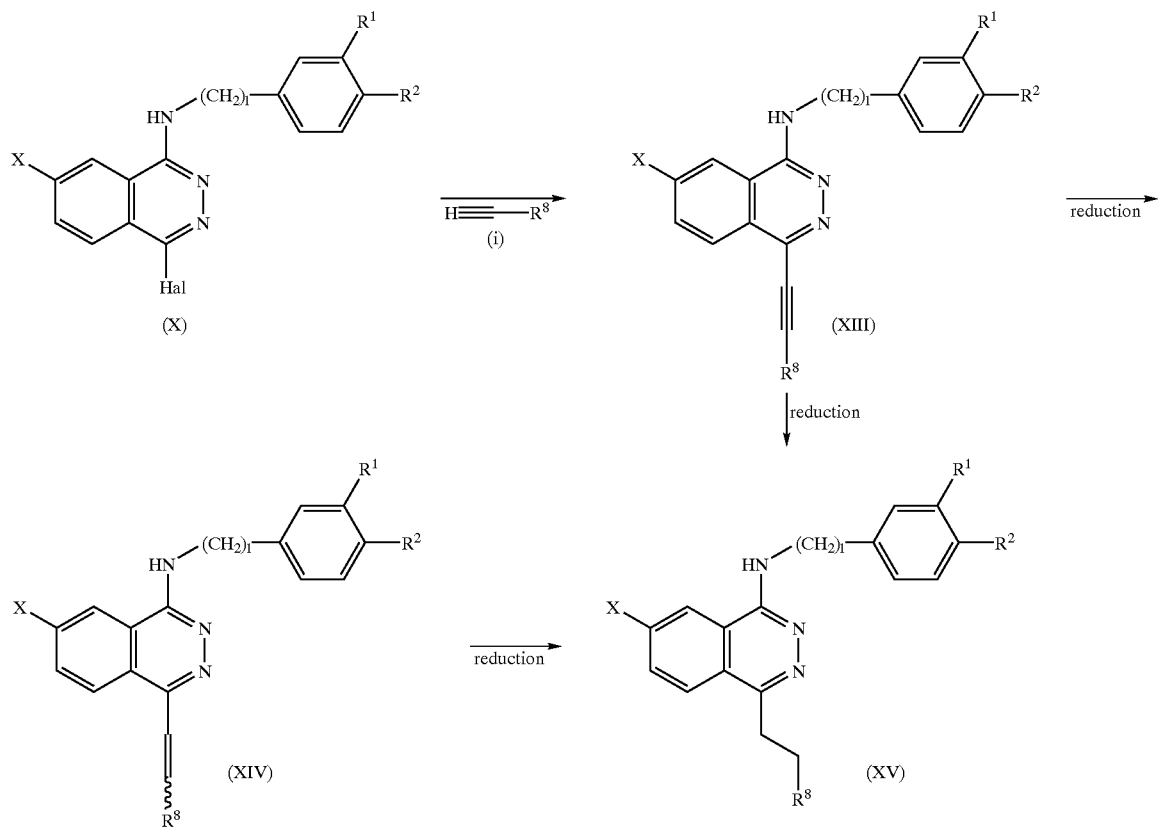

wherein Hal is a halogen atom; $R^8$ is an optionally substituted C1 to C4 alkyl group, or an optionally substituted cycloalkyl or cycloalkylalkyl group; and $R^1$, $R^2$, l and X have the meanings defined above.

The reaction of the compound of the formula (X) with the alkyne compound is conducted in the presence of a catalytic amount of dichlorobistriphenyl phosphine palladium (II), cuprous iodide and a tertiary amine, at room temperature or under heating. The solvent used includes dimethylformamide or 1-methylpyrrolidinone. The tertiary amine used includes triethylamine, diisopropylethylamine, DBU and dimethylaniline. The reaction temperature is preferably 0 to 150° C.

The conversion of the alkyne compound represented by the formula (XIII) into the alkene compound represented by the formula (XIV) or the alkane compound represented by the formula (XV) is conducted by catalytic reduction, etc. in the presence of a Lindlar catalyst or a Pd-C catalyst.

PRODUCTION PROCESS 3

Further, the phthalazine compounds wherein Y is $Y^3$ that is an optionally substituted aryl group or a heteroaryl group are produced as follow:

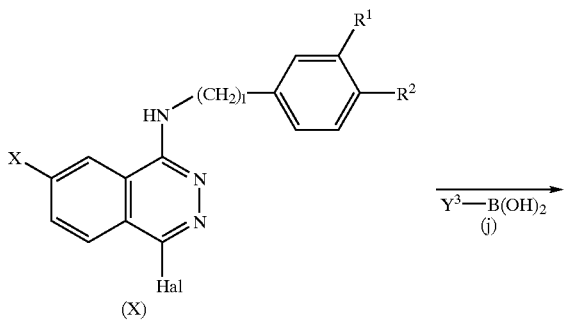

(X)

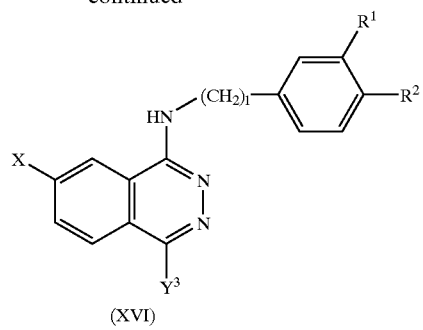

(XVI)

wherein $Y^3$ is a phenyl group, a pyridyl group, a pyrimidyl group, a thienyl group or a furyl group all of which may have 1 to 3 substituent groups selected from the above substituent group A; Hal is a halogen atom; and $R^1$, $R^2$, l and X have the same meanings as defined above.

The reaction is conducted by coupling the 1-halogenoquinazoline compound represented by the formula (X) by a zero-valent or divalent palladium complex to a boric acid, dialkoxy borane or trialkyl tin compound having a corresponding aryl group or heteroaryl group. The boric acid, dialkoxy borane or trialkyl tin compound having an aryl group or a heteroaryl group, and the palladium complex are dissolved or suspended in a 2-phase solvent consisting of an organic solvent and an aqueous solution of sodium carbonate. And the mixture is reacted at the temperature in the range of from at room temperature to the boiling point of the solvent for about 1 to 24 hr in a nitrogen gas stream. As the palladium complex, any palladium complex which allows the reaction to proceed can be used, and tetrakis(triphenylphosphine)palladium, etc. are preferable. As the organic solvent, any solvent which is inert to the the reaction can be used, and xylene, toluene, tetrahydrofuran or a mixed solvent thereof are preferable.

PRODUCTION PROCESS 4

In the formula (I), the compounds shown in the following reaction scheme can be produced by combining known reactions by using the compound (XVII) wherein X is a cyano group.

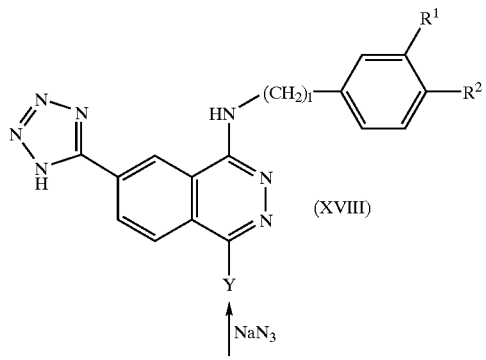

(XVIII)

-continued

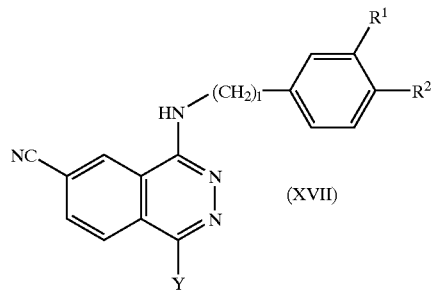

(XVII)

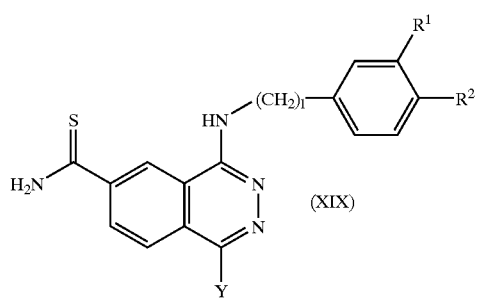

(XIX)

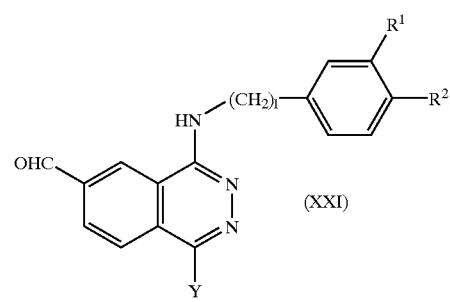

(XXI)

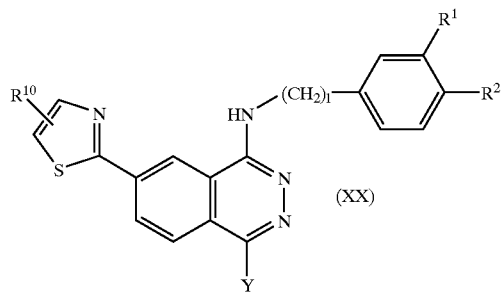

(XX)

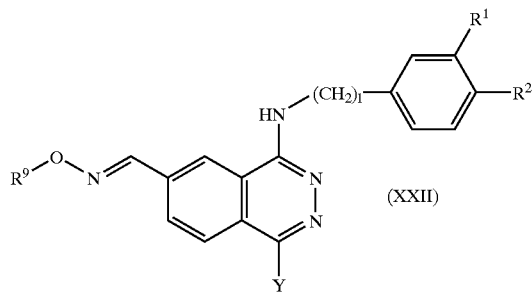

(XXII)

wherein $R^9$ is a hydrogen atom, a C1 to C4 alkyl group which may be substituted with a halogen atom, an aryl C1 to C4 alkyl group or a carboxy C1 to C4 alkyl group; $R^{10}$ is a C1 to C4 alkyl group; and $R^1$, $R^2$, l and Y have the same meanings as defined above.

PRODUCTION PROCESS 5

Some of compounds of the formula (I) wherein X is a heteroaryl group can be produced in the same manner as in Production Process 3.

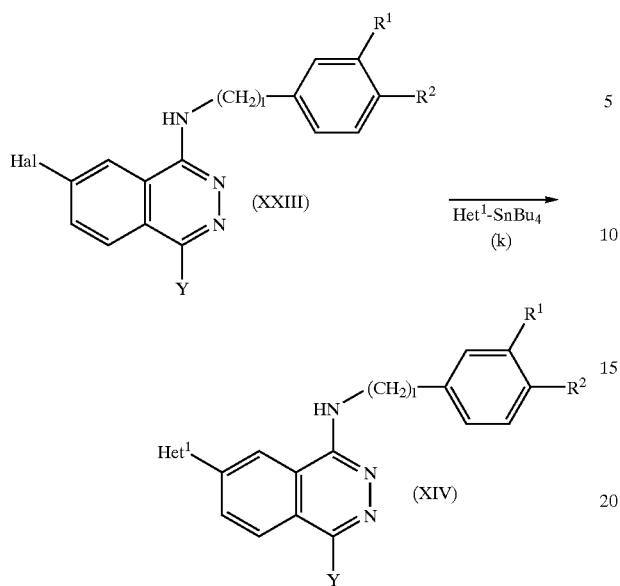

wherein Hal is a halogen atom; Het 1 is a heteroaryl group; and $R^1$, $R^2$, 1 and Y have the same meanings as defined above.

The halogen atom is preferably a bromine atom or an iodine atom.

Further, the compounds of formula (I) with an azolyl group not having a heteroatom other than a nitrogen atom are produced according to the above-mentioned Production Process 1, after the corresponding compound represented by the formula (X) is previously produced. The corresponding compound of formula (X) is produced, for example, according to a method disclosed in WO9605176 after dimethyl 4-fluorophthalate is treated with azole not containing a heteroatom other than a nitrogen atom to give dimethyl 4-azolylphthalate and then treated with hydrazine to give 6-azolyl-2,3-dihydro-1,4-phthalazine dione.

PRODUCTION PROCESS 6

The compound of the formula (I) wherein Y is represented by the formula (VI) can be produced by converting the compound represented by the following formula (XXIV) into the oxime in a known method:

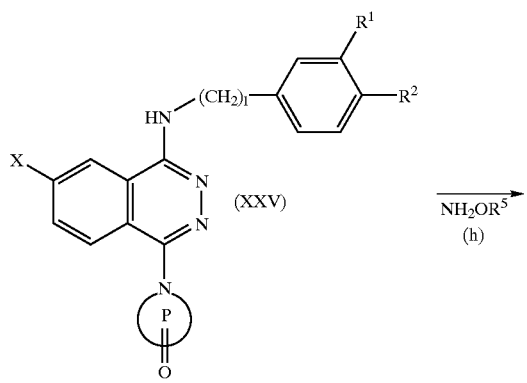

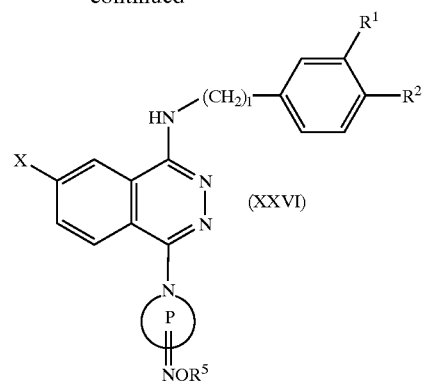

wherein $R^1$, $R^2$, $R^5$, 1 and X have the same meanings as defined above.

Hereinafter, the effect of the compounds of the present invention is described by reference to Experimental Examples.

1) Inhibitory Action on the Enzyme cGMP-PDE Obtained from Porcine Platelets

The inhibitory activity of a test compound on the enzyme cGMP-PDE prepared from porcine platelets was determined by adding a solution of the test compound dissolved in DMSO to a reaction solution, where 1 μM cGMP was used as the substrate in the presence of 1 mM EGTA in accordance with a method of Tompson et al. The final concentration of DMSO in the reaction solution was 1% or less. Preparation of cGMP-PDE was conducted as follows. Porcine platelets were added to buffer A (20 mM Tris/HCl, 2 mM magnesium acetate, 10 mM 2-mercaptoethanol, 0.1 mM EGTA; pH 7.4), and then sonicated. The resulting suspension was centrifuged at 100,000×g for 60 min, and the resulting supernatant was subjected to a column (DEAE-Toyopearl 650S produced by Tosoh, Tokyo, Japan). After the column was washed with buffer A, the enzyme was eluted with a gradient of from 0.075 to 0.25 M NaCl in buffer A to give a CGMP-PDE fraction. The resulting fraction was dialyzed, concentrated and stored.

TABLE 1

Inhibitory Action on PDE5

| | test compound | PDE 5 $IC_{50}$ (nM) |
|---|---|---|
| 1 | Production Example 1 | 0.09 |
| 2 | Production Example 3 | 0.72 |
| 3 | Production Example 4 | 0.19 |
| 4 | Production Example 5 | 0.23 |
| 5 | Production Example 6 | 0.5 |
| 6 | Production Example 7 | 0.03 |
| 7 | Production Example 8 | 0.47 |
| 8 | Production Example 11 | 0.24 |
| 9 | Example 1 | 0.78 |
| 10 | Example 2 | 0.30 |
| 11 | Example 3 | 1.1 |
| 12 | Example 4 | 0.51 |
| 13 | Example 5 | 0.051 |
| 14 | Example 6 | 0.98 |
| 15 | Example 9 | 0.54 |
| 16 | Example 11 | 0.68 |
| 17 | Example 12 | 0.54 |
| 18 | Example 25 | 0.16 |
| 19 | Example 36 | 0.25 |
| 20 | Example 43 | 0.23 |

TABLE 1-continued

Inhibitory Action on PDE5

| | test compound | PDE 5 $IC_{50}$ (nM) |
|---|---|---|
| 21 | Example 50 | 0.24 |
| 22 | Example 52 | 0.20 |
| 23 | Example 76 | 0.13 |
| 24 | Example 77 | 0.23 |
| 25 | Example 79 | 0.27 |
| 26 | Example 83 | 0.5 |
| 27 | Example 84 | 0.93 |
| 28 | Example 85 | 0.12 |
| 29 | Example 88 | 0.89 |
| 30 | Example 105 | 0.10 |
| 31 | Example 110 | 0.66 |

2) Augmenting Action of the PDE5 Inhibitor on the Relaxing Action of Nitroprusside on a Penile Cavernosum Preparation Removed from a Rabbit The penis was removed from a NZW white rabbit (about 3 kg) killed by intravenous administration of pentobarbital (50 mg/kg). After removal, the cavernosum was exposed by removal of surrounding tissues such as albuginea to give a preparation (about 10×1.5×1.5 mm). This preparation was suspended on a Magnus tube filled up with 10 ml Krebs-Henseleit's nutritive solution (118.4 mM NaCl, 4.7 mM KCl, 2.5 mM $CaCl_2$, 1.3 mM $MgSO_4$, 1.2 mM $KH_2PO_4$, 25.0 mM $NaHCO_3$, 11.0 mM glucose, 0.026 mM EDTA and 0.001 mM indomethacin) at 37° C., and a gas mixture (95% oxygen+5% carbon dioxide) was bubbled thereinto. Then, the isometric tension was recorded under a load of 2 g. To stabilize the contraction, contraction caused by adding a potassium chloride solution (final concentration: 100 mM) and washing were repeated twice, and further, contraction by adding phenylephrine (final concentration: 10 μM) and washing were also conducted.

It was filled up again with 10 ml Krebs-Henseleit's solution, and L-$N^G$-nitroarginine methyl ester (final concentration: 100 μM) was added to inhibit the formation of endogenous nitrogen monoxide. Contraction was caused by adding phenylephrine (final concentration: 10 μM), and a chemical solution was added thereto at a final concentration of 3, 30 or 300 nM. Dimethyl sulfoxide was used as the medium in this reaction. 15 min after the chemical was added, nitroprusside (final concentration: 300 μM) was added to relax the preparation. Further, papaverine (final concentration: 100 μM) was added to determine the maximum relaxation.

After the experiment, the tension generated upon adding papaverine was used as the base line, and the relaxation of the preparation by adding nitroprusside was recorded on a chart by using a DEGIMATIC CALIPER to determine the degree of relaxation.

TABLE 2

Augmenting action of PDE5 inhibitor on the relaxation, by nitroprusside, of the penile cavernosum preparation removed from a rabbit

| | Relaxation ratio (%) | | | |
|---|---|---|---|---|
| test compound | 3 nM | 30 nM | 300 nM | $EC_{50}$ (nM) |
| Example 9 | 56.6 | 77.7 | 79.6 | 2.0 |
| Example 36 | 35.0 | 60.8 | 54.8 | 3.5 |
| Example 37 | 33.4 | 50.1 | 56.0 | 29.3 |
| Example 77 | 58.8 | 71.7 | 80.6 | 0.7 |
| Example 83 | 50.6 | 67.3 | 69.9 | 2.8 |
| Example 86 | 50.2 | 70.2 | 71.5 | 3.0 |
| Example 88 | 50.0 | 67.5 | 75.0 | 3.0 |

Values in the table indicate relaxation ratio (%) after nitroprusside was added to the preparation pretreated with the 3, 30 and 300 nM compound, and the mean in a duplicate experiment was recorded. Further, the $EC_{50}$ value indicates the compound concentration at which the contraction caused by phenylephrine is relaxed by 50%, and this value was calculated by regression analysis on a relaxation curve in the duplicate experiment.

Nitrogen monoxide formed from nitroprusside activated guanylate cyclase to promote the formation of cGMP from GTP, thus relaxing the penile cavernosum. The PDE5 inhibitor augmented this relaxation action by inhibiting the degradation of cGMP.

As described above, it was demonstrated that the compounds of the present invention have an inhibitory action on PDE5 and augment the relaxation action of nitroprusside on the rabbit penile cavernosum sample dose-dependently.

That is, the present invention is useful as a prophylactic and therapeutic agent for erectile dysfunction.

Production Examples and Examples are given to facilitate the understanding of the present invention, but as a matter of course, the present invention is not limited to these compounds.

PRODUCTION EXAMPLE 1

4-(3-Chloro-4-methoxybenzyl)amino-6-cyano-1-[(3R)-3-hydroxypiperidino]phthalazine Hydrochloride

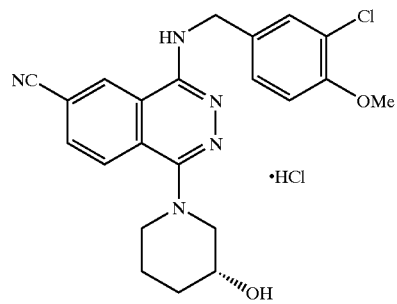

A mixture of 1.0 g 1-chloro-4-(3-chloro-4-methoxybenzyl)amino-6-cyanophthalazine, 1.92 g (R)-(+)-3-hydroxypiperidine hydrochloride, 1.80 g diisopropyl ethylamine and 12 ml 1-methyl-2-pyrrolidone was stirred at 170° C. for 1 hr and 15 min. After cooling, ethyl acetate was added to the reaction solution which was then washed with water and brine. It was dried over anhydrous sodium sulfate, the solvent was evaporated, and the resulting residue was purified by silica gel column chromatography. The resulting free compound was suspended in acetic acid/ethanol/water, 1 N aqueous hydrochloric acid was added thereto, and it was dissolved by heating. After cooling, the resulting crystals were collected by filtration to give 860 mg of the title compound as a yellow powder.

MASS (ESI): 424.1 (MH$^+$); $^1$H-NMR (400 MHz, DMSO-$d_6$) δ; 1.39–1.50 (1H, m), 1.65–1.78 (1H, m), 1.75–1.98 (2H, m), 2.82–2.91 (1H, m), 2.93–3.02 (1H, m), 3.33–3.48 (2H, m), 3.79–3.88 (1H, m), 3.85 (3H, s), 4.72 (2H, br), 7.16 (1H, d, J=8.4 Hz), 7.47 (1H, dd, J=8.4, 1.6 Hz), 7.62 (1H, d, J=1.6 Hz), 8.31 (1H, d, J=8.4 Hz), 8.48 (1H, d, J=8.4 Hz), 9.38–9.46 (1H, m), 10.27 (1H, br).

PRODUCTION EXAMPLE 2

4-(3-Chloro-4-methoxybenzyl)amino-6-cyano-1-[(3S)-3-hydroxypyrrolidino]phthalazine Hydrochloride

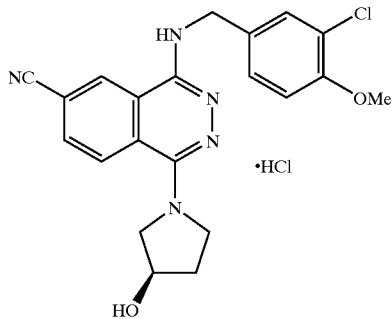

The title compound was obtained by using (S)-3-hydroxypyrrolidine in place of (R)-(+)-3-hydroxypiperidine hydrochloride in Production Example 1.

MASS (ESI); 410.0 (MH$^+$); $^1$H-NMR(400 MHz, DMSO-$d_6$) δ; 1.94–2.10 (2H, m), 3.50–3.62 (1H, m), 3.42–3.68 (1H, m), 3.83 (3H, s), 3.93–4.10 (2H, m), 4.43–4.50 (1H, m), 4.50–4.64 (2H, m), 5.30 (1H, br), 7.13 (1H, d, J=8.4 Hz), 7.34–7.44 (1H, m), 7.48–7.56 (1H, m), 8.38–8.46 (1H, m), 8.62–8.74 (1H, m), 9.10–9.32 (1H, m).

PRODUCTION EXAMPLE 3

4-(3-Chloro-4-methoxybenzyl)amino-6-cyano-1-[(2S)-2-hydroxymethylpyrrolidino]phthalazine Hydrochloride

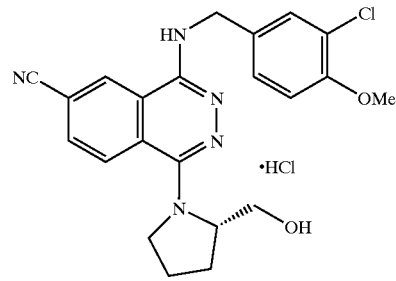

The title compound was obtained by using (S)-2-hydroxymethylpyrrolidine in place of (R)-(+)-3-hydroxypiperidine hydrochloride in Production Example 1.

MASS (ESI); 424.1 (MH$^+$); $^1$H-NMR(400 MHz, DMSO-$d_6$) δ; 1.60–2.39 (4H, m), 3.44–3.53 (1H, m), 3.83 (3H, s), 3.89–3.99 (1H, m), 4.34–4.70 (3H, m), 7.12–7.16 (1H, m), 7.38–7.46 (1H, m), 7.52–7.59 (1H, m), 8.40–8.43 (1H, m), 8.43–8.60 (1H, m), 9.23–9.30 (1H, m).

PRODUCTION EXAMPLE 4

4-(3-Chloro-4-methoxybenzyl)amino-6-cyano-1-(3-hydroxymethylpiperidino)phthalazine Hydrochloride

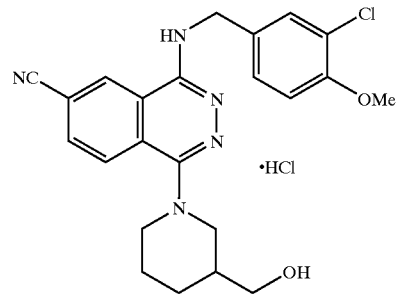

The title compound was obtained by using 3-hydroxymethylpiperidine in place of (R)-(+)-3-hydroxypiperidine hydrochloride in Production Example 1.

MASS (ESI); 438.2 (MH$^+$); $^1$H-NMR(400 MHz, DMSO-$d_6$) δ; 1.13–1.28 (1H, m), 1.70–1.86 (3H, m), 1.87–1.99 (1H, m), 2.67–2.75 (1H, m), 2.86–2.95 (1H, m), 3.33–3.50 (3H, m), 3.51–3.60 (1H, m), 3.16 (3H, s), 3.85 (3H, s), 4.71 (2H, br-s), 7.16 (1H, d, J=8.4 Hz), 7.44 (1H, dd, J=8.4, 0.8 Hz), 7.59 (1H, d, J=0.8 Hz), 8.23 (1H, d, J=8.8 Hz), 8.45 (1H, dd, J=8.8, 0.4 Hz), 9.28–9.35 (1H, m), 9.95 (1H, br), 14.00 (1H, br).

PRODUCTION EXAMPLE 5

4-(3-Chloro-4-methoxyphenethyl)amino-6-cyano-1-(3-hydroxymethylpiperidino)phthalazine Hydrochloride

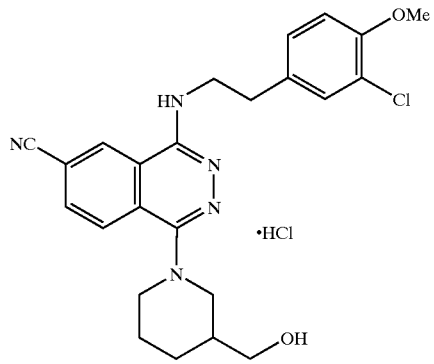

The title compound was obtained by using 1-chloro-4-(3-chloro-4-methoxyphenethyl)amino-6-cyanophthalazine in place of 1-chloro-4-(3-chloro-4-methoxybenzyl)amino-6-cyanophthalazine in Production Example 4.

MASS (ESI); 452.3 (MH$^+$); $^1$H-NMR(400 MHz, DMSO-d$_6$) δ; 1.70–1.90 (2H, m), 1.90–2.05 (2H, m), 2.70 (1H, br-t), 2.88 (1H, br-t), 2.95–3.08 (2H, m), 3.25–3.63 (2H, m), 3.78 (2H, m), 3.83 (3H, s), 7.09 (1H, d, J=8.6 Hz), 7.29 (1H, d, J=8.6 Hz), 7.47 (1H, s), 8.25 (1H, d, J=8.6 Hz), 8.49 (1H, d, J=8.6 Hz), 9.48 (1H, s).

PRODUCTION EXAMPLE 6

4-(3-Chloro-4-methoxyphenethyl)amino-6-cyano-1-(4-hydroxymethylpiperidino)phthalazine

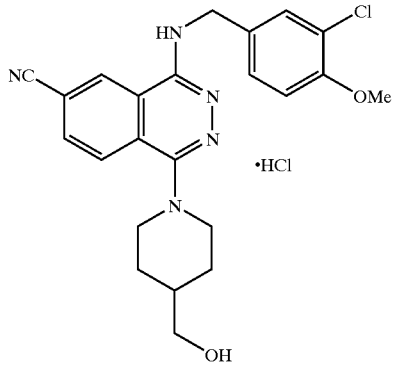

The title compound was obtained by using 4-hydroxymethylpiperidine in place of 3-hydroxymethylpiperidine in Production Example 5.

MASS (ESI); 452.3 (MH$^+$); $^1$H-NMR(400 MHz, CDCl$_3$) δ; 1.51–1.65 (2H, m), 1.79–1.85 (1H, m), 1.93 (2H, m), 2.99–3.09 (4H, m), 3.56–3.68 (4H, m), 3.90 (3H, s), 3.85–3.99 (2H, m), 4.94 (1H, br-t), 6.88 (1H, d, J=8.4 Hz), 7.13 (1H, dd, J=2.2, 8.4 Hz), 7.28 (1H, d, J=2.2 Hz), 7.94 (1H, d, J=8.4 Hz), 7.98 (1H, s), 8.13 (1H, d, J=8.4 Hz).

PRODUCTION EXAMPLE 7

4-(3-Chloro-4-methoxybenzyl)amino-6-cyano-1-[methyl(2-pyridylmethyl)amino]phthalazine Dihydrochloride

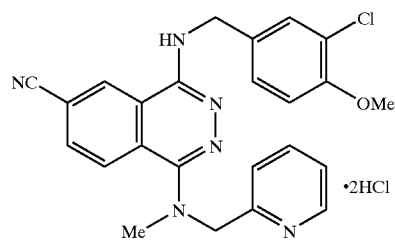

The title compound was obtained in the same treatment as in Production Example 1 except that N-methyl-[(2-pyridyl)methyl]amine was used in place of (R)-(+)-3-hydroxypiperidine hydrochloride.

MASS (ESI); 445.3 (MH$^+$); $^1$H-NMR (400 MHz, DMSO-d$_6$) δ; 2.95 (3H, s), 3.85 (3H, s), 4.73–4.79 (4H, m), 7.16 (1H, d, J=8.4 Hz), 7.49 (1H, dd, J=8.4, 2.0Hz), 7.64 (1H, d, J=2.0 Hz), 7.65–7.72 (1H, m), 7.83–7.87 (1H, m), 8.18–8.26 (1H, m), 8.52 (1H, dd, J=8.4, 1.2 Hz), 8.60 (1H, d, J=8.4 Hz), 8.74 (1H, d, J=4.8 Hz), 9.53–9.55 (1H, m), 10.64 (1H, br).

PRODUCTION EXAMPLE 8

4-(3-Chloro-4-methoxybenzyl)amino-6-cyano-1-{N-methyl-[2-(2-pyridyl)ethyl]amino}phthalazine Dihydrochloride

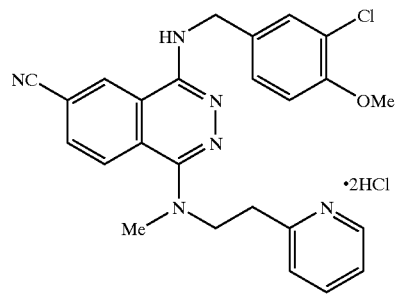

The title compound was obtained in the same treatment as in Production Example 7 except that N-methyl-[2-(2-pyridyl)ethyl]amine was used in place of N-methyl-[(2-pyridyl) methyl]amine.

MASS (ESI); 459.2 (MH$^+$); $^1$H-NMR(400 MHz, DMSO-d$_6$) δ; 3.00 (3H, s), 3.35 (2H, t, J=6.4 Hz), 3.76 (2H, t, J=6.4 Hz), 3.85 (3H, s), 4.73–4.77 (2H, m), 7.18 (1H, d, J=8.4 Hz), 7.50 (1H, d, J=8.4 Hz), 7.53–7.64 (1H, m), 7.65 (1H, s), 7.68–7.77 (1H, m), 8.81–8.30 (1H, m), 8.16 (1H, d, J=8.6 Hz), 8.44 (1H, d, J=,8.6 Hz), 8.55–8.61 (1H, m, 9.45–9.51 (1H, m), 10.53 (1H, br).

PRODUCTION EXAMPLE 9

4-(3-Chloro-4-methoxyphenethyl)amino-6-cyano-1-(4-methoxypiperidino)phthalazine Hydrochloride

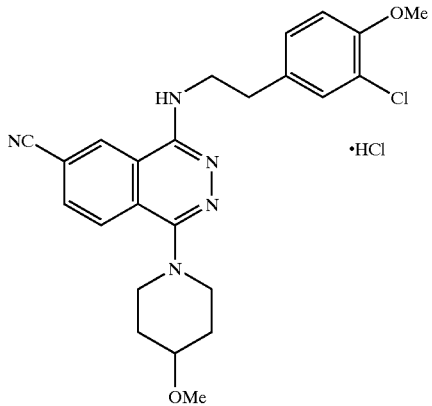

The title compound was obtained in the same treatment as in Production Example 5 except that 4-methoxylpiperidine hydrochloride was used in place of 3-hydroxymethylpiperidine.

MASS (ESI); 452.2 (MH$^+$); $^1$H-NMR(400 MHz, DMSO-d$_6$) δ; 1.66–1.76 (2H, m), 2.00–2.08 (2H, m), 2.91–2.97 (2H, m), 2.99–3.07 (2H, m), 3.29 (3H, s), 3.37–3.49 (3H, m), 3.70–3.77 (2H, m), 3.81 (3H, s), 7.07 (1H, d, J=8.6 Hz), 7.26 (1H, dd, J=8.6, 2.0 Hz), 7.43 (1H, d, J=2.0 Hz), 8.24 (1H, d, J=8.3 Hz), 8.45 (1H, dd, J=8.3, 1.6 Hz), 9.22 (1H, d, J=1.6 Hz).

PRODUCTION EXAMPLE 10

4-(3-Chloro-4-methoxybenzyl)amino-6-cyano-1-(4-methoxyphenyl)phthalazine Hydrochloride

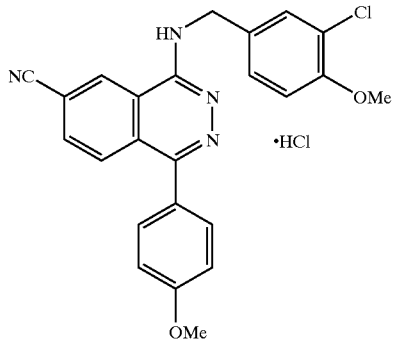

423 mg of tetrakis(triphenylphosphine)palladium (0) was added to a mixture of 1.0 g 1-chloro-4-(3-chloro-4-methoxybenzyl)amino-6-cyanophthalazine, 423 mg 4-methoxyphenylboric acid, 30 ml toluene, 30 ml tetrahydrofuran, and 30 ml of 2 M aqueous sodium carbonate in a nitrogen atmosphere. The mixture was stirred at 80° C. for 2 hr, and further at 10° C. for 15.5 hr. The reaction solution was returned to room temperature and extracted with aqueous ammonium chloride and ethyl acetate. The organic layer was washed with aqueous ammonia, water and brine, and dried over anhydrous sodium sulfate. The solvent was evaporated, and the resulting residue was purified by silica gel column chromatography. The resulting coupled compound was dissolved in ethyl acetate/ethanol, 4 N hydrochloric acid/ethyl acetate solution was added thereto, and the resulting crystals were collected by filtration to give 460 mg of the title compound as a yellow powder.

MASS (ESI); 431.2 (MH$^+$); $^1$H-NMR(400 MHz, DMSO-d$_6$) δ; 3.85 (3H, s), 3.87 (3H, s), 4.82–4.85 (2H, m), 7.16–7.21 (3H, m), 7.49 (1H, dd, J=8.6, 2.2 Hz), 7.60–7.63 (3H, m), 8.08 (1H, d, J=8.4 Hz), 8.45 (1H, dd, J=8.4, 1.4 Hz), 9.45–9.49 (1H, m), 10.39 (1H, br).

PRODUCTION EXAMPLE 11

4-[(3-Chloro-4-methoxybenzyl)amino]-1-(4-hydroxy-3-methylpiperidino)-6-phthalazinecarbonitrile Hydrochloride The title compound was obtained in the same treatment as in Production Example 1 except that 4-hydroxy-3-methylpiperidine in place of (R)-(+)-3-hydroxypiperidine hydrochloride.

$^1$H-NMR (400 MHz, DMSO-d$_6$) δ; 0.94 (3H, t, J=8.0 Hz), 1.59–2.03 (3H, m), 2.74–3.96 (5H, m), 3.83 (3H, s), 4.68 (2H, d, J=5.2 Hz), 7.15 (1H, d, J=8.4 Hz), 7.43 (1H, d, J=8.0 Hz), 7.58 (1H, s), 8.23 (1H, t, J=8.0 Hz), 8.45 (1H, d, J=8.4 Hz), 9.29 (1H, s).

PRODUCTION EXAMPLE 12

4-[(3-Chloro-4-methoxybenzyl)amino]-1-(4-hydroxy-3,3,5,5-tetramethylpiperidino)-6-phthalazinecarbonitrile Hydrochloride The title compound was obtained in the same treatment as in Production Example 1 except that 4-hydroxy-3,3,5,5-tetramethylpiperidine was used in place of (R)-(+)-3-hydroxypiperidine hydrochloride.

$^1$H-NMR (400 MHz, DMSO-d$_6$) δ; 0.91 (6H, s), 1.15 (6H, s), 2.57 (1H, d, J=12.4 Hz), 2.95 (1H, s), 3.21 (2H, d, J=12.0 Hz), 3.83 (3H, s), 4.47 (2H, d, J=5.6 Hz), 7.14 (1H, d, J=8.4 Hz), 7.47 (1H, d, J=8.8 Hz), 7.63 (1H, s), 8.29 (1H, d, J=8.4 Hz), 8.55 (1H, d, J=8.4 Hz), 9.52 (1H, s), 10.63 (1H, br-s).

INTERMEDIATE PRODUCTION EXAMPLE 1

1-Chloro-4-{[(4-methoxy-3-trifluoromethyl)benzyl]amino}-6-phthalazine Carbonitrile

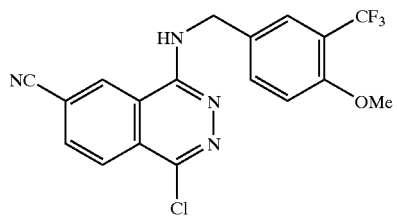

A mixture of log 2-trifluoromethyl phenol, 17 g potassium carbonate, 150 ml acetone and 7.7 ml iodomethane was heated under reflux for 2 hr. After cooling, the insoluble matters were removed by filtration, and the filtrate was evaporated. The resulting residue was dissolved in ethyl acetate, and washed with water and brine. It was dried over anhydrous magnesium sulfate, filtered, and evaporated to give 12.15 g of 2-trifluoromethyl anisole.

A mixture of 8.5 g 2-trifluoromethyl anisole and 7.0 g hexamethylene tetramine was stirred at 90° C. for 1.5 hr in 80 ml trifluoroacetic acid. The reaction solution was evaporated. The resulting residue was dissolved in ethyl acetate, and it was added dropwise into ice-cooled saturated aqueous sodium bicarbonate. The ethyl acetate layer was recovered and washed with brine. It was dried over anhydrous magnesium sulfate, filtered, and evaporated. The resulting residue was purified by silica gel column chromatography to give 5.8 g of 3-trifluoromethyl-p-anisaldehyde.

A mixture of 5.8 g 3-trifluoromethyl-p-anisaldehyde, 8.6 ml formamide, and 13.6 ml formic acid was stirred at 130° C. for 9 hr. After cooling, water and ethyl acetate were added thereto. The ethyl acetate layer was recovered and washed with brine. It was dried over anhydrous magnesium sulfate, filtered, and evaporated. The resulting residue was purified by silica gel column chromatography to give 3.8 g of N-[4-methoxy-3-(trifluoromethyl)benzyl]formamide.

3.8 g of N-[4-methoxy-3-(trifluoromethyl)benzyl] formamide was dissolved in 20 ml ethanol, 2 ml conc. hydrochloric acid was added thereto, and the mixture was heated under reflux for 3 hr. After cooling, diethyl ether was added thereto, and the resulting crystals were collected by filtration to give 2.5 g of 4-methoxy-3-(trifluoromethyl) benzylamine hydrochloride.

3.7 g of DBU was added to a mixture of 2.2 g 1,4-dichlorophthalazine-6-carbonitrile, 2.5 g 4-methoxy-3-(trifluoromethyl)benzylamine hydrochloride and 25 ml 1-methyl-2-pyrrolidinone, and the mixture was stirred at room temperature for 1.25 hr. Ethyl acetate was added to the reaction solution which was then washed with water and brine. It was dried over anhydrous sodium sulfate, filtered and evaporated. The resulting residue was purified by silica gel column chromatography to give 1.66 g of the title compound as a less polar compound.

$^1$H-NMR(400 MHz, DMSO-$d_6$) δ; 3.86 (3H, s), 4.74 (2H, d, J=5.2 Hz), 7.22 (1H, d, J=9.6 Hz), 7.67–7.71 (2H, m), 8.20 (1H, d, J=8.4 Hz), 8.35 (1H, dd, J=8.4, 1.4 Hz), 8.50 (1H, t, J=5.2 Hz), 8.99 (1H, d, J=1.4 Hz).

In the same manner, 1-chloro-4-[(3-iodo-4-methoxybenzyl)amino]-6-phthalazine carbonitrile was obtained from commercial 2-iodoanisole; 4-[(3-bromo-4-methoxybenzyl)amino]-1-chloro-6-phthalazine carbonitrile from 3-bromo-p-anisaldehyde; 1-chloro-4-[(3-fluoro-4-methoxybenzyl)amino]-6-phthalazine carbonitrile from 3-fluoro-p-anisaldehyde; and 1-chloro-4-[(4-methoxy-3-methylbenzyl)amino]-6-phthalazine carbonitrile from 3-methyl-p-anisaldehyde.

INTERMEDIATE PRODUCTION EXAMPLE 2

1-Chloro-4-[(3-iodo-4-methoxybenzyl)amino]-6-phthalazine Carbonitrile $^1$H-NMR (400 MHz, DMSO-$d_6$) δ; 3.80 (3H, s), 4.67 (2H, d, J=5.2 Hz), 6.96 (1H, d, J=8.4 Hz), 7.42 (1H, dd, J=8.4, 2.0 Hz), 7.83 (1H, d, J=2.0 Hz), 8.18 (1H, d, J=8.4 Hz), 8.34 (1H, dd, J=8.4, 1.2 Hz), 8.45 (1H, t, J=5.2 Hz), 8.99 (1H, d, J=1.2 Hz).

INTERMEDIATE PRODUCTION EXAMPLE 3

4-[(3-Bromo-4-methoxybenzyl)amino]-1-chloro-6-phthalazine Carbonitrile $^1$H-NMR (400 MHz, DMSO-$d_6$) δ; 3.82 (3H, s), 4.70 (2H, d, J=5.2 Hz), 7.07 (1H, d, J=8.4 Hz), 7.41 (1H, dd, J=8.4, 2.0 Hz), 7.63 (1H, d, J=2.0 Hz), 8.20 (1H, d, J=8.4 Hz), 8.34 (1H, dd, J=8.4, 1.2 Hz), 8.47 (1H, t, J=5.2 Hz), 8.99 (1H, d, J=1.2 Hz).

INTERMEDIATE PRODUCTION EXAMPLE 4

1-Chloro-4-[(3-fluoro-4-methoxybenzyl)amino]-6-phthalazine Carbonitrile $^1$H-NMR (400 MHz, DMSO-$d_6$) δ; 3.81 (3H, s), 4.70 (2H, d, J=5.4 Hz), 7.11 (1H, t, J=8.8 Hz), 7.19 (1H, d, J=8.8 Hz), 7.26 (1H, dd, J=12.8, 2.0 Hz), 8.20 (1H, d, J=8.4 Hz), 8.35 (1H, dd, J=8.4, 0.8 Hz), 8.46 (1H, t, J=5.4 Hz), 9.01 (1H, d, J=0.8 Hz).

INTERMEDIATE PRODUCTION EXAMPLE 5

1-Chloro-4-[(3-cyano-4-methoxybenzyl)amino]-6-phthalazine Carbonitrile

A mixture of 20 g 4-methoxybenzyl chloride, 26 g phthalimide potassium, and 100 ml dimethylformamide was stirred at 50° C. for 5 hr. After cooling, the reaction solution was poured into ice water and the resulting precipitates were collected by filtration. These were washed with water and dried to give 31 g of N-(4-methoxybenzyl)phthalimide.

18 g of hexamethylene tetramine was added little by little to a mixture of 31 g N-(4-methoxybenzyl)phthalimide and 100 ml trifluoroacetic acid, stirred at room temperature for 1 hr, and then heated under reflux for 4 hr. The reaction solution was cooled to 1° C., and water was added thereto. Potassium carbonate was added thereto and the resulting crystals were collected by filtration. The crystals were dried to give 20 g of N-(3-formyl-4-methoxybenzyl)phthalimide.

5.2 g of hydroxylamine hydrochloride, 12.2 g of sodium acetate, and 50 ml water were added to a mixture of 20 g N-(3-formyl-4-methoxybenzyl)phthalimide and 200 ml tetrahydrofuran, and stirred at room temperature for 1 hr. It was stirred at 60° C. for 1 hr, and then evaporated. Water was added to the resulting residue, and the insoluble matters were collected by filtration. These were washed with diethyl ether to give 20 g of N-(3-hydroxyimino-4-methoxybenzyl) phthalimide.

6.7 ml acetic anhydride was added to a mixture of 20 g N-(3-hydroxyimino-4-methoxybenzyl)phthalimide and 200 ml xylene, and the mixture was heated under reflex for 10 hr. It was returned to room temperature, and the resulting crystals were collected by filtration and washed with xylene to give 15 g of N-(3-cyano-4-methoxybenzyl)phthalimide.

3.9 g of hydrazine monohydrate was added to a mixture of 15 g N-(3-cyano-4-methoxybenzyl)phthalimide and 200 ml ethanol, and the mixture was heated under reflux for 3 hr. After cooling, the insoluble matters were removed by filtration. The filtrate was evaporated, 1 N aqueous sodium hydroxide was added to the resulting residue which was then extracted with dichloromethane. The extract was dried over anhydrous magnesium sulfate, and filtered. The filtrate was evaporated to give 8.0 g of 3-cyano-4-methoxybenyzlamine.

1,4-Dichlorophthalazine-6-carbonitrile and 3-cyano-4-methoxybenzylamine were stirred at room temperature in 1-methyl-2-pyrrolidinone in the presence of DBU, whereby 1-chloro-4-[(3-cyano-4-methoxybenzyl)amino]-6-phthalazine carbonitrile was obtained as a less polar product.

$^1$H-NMR (400 MHz, DMSO-d$_6$) δ; 3.87 (3H, s), 4.70 (2H, d, J=5.6 Hz), 7.20 (1H, d, J=8.4 Hz), 7.70 (1H, dd, J=2.4, 8.4 Hz), 7.75 (1H, d, J=2.4 Hz), 8.19 (1H, d, J=8.4 Hz), 8.34 (1H, dd, J=1.2, 8.4 Hz), 8.48 (1H, t, J=5.6 Hz), 8.97 (1H, s).

INTERMEDIATE PRODUCTION EXAMPLE 6

1-Chloro-4-[(3-ethyl-4-methoxybenzyl)amino]-6-phthalazinecarbonitrile 3.99 g of potassium-t-butoxide was added to 80 ml solution of 12.7 g methyltriphenyl phosphonium bromide in tetrahydrofuran at 0° C., 7 g of N-(3-formyl-4-methoxybenzyl)phthalimide was added thereto, and the mixture was stirred at room temperature for 1 hr. The reaction solution was filtered through Celite, and then evaporated. The resulting residue was purified by silica gel column chromatography to give 2.75 g of N-(4-methoxy-3-vinylbenzyl)phthalimide.

2.75 g of N-(4-methoxy-3-vinylbenzyl)phthalimide was dissolved in 50 ml tetrahydrofuran, 0.1 g of 10% Pd-C was added thereto, and the mixture was stirred for 40 min in a hydrogen atmosphere. The reaction solution was filtered through Celite, and the filtrate was evaporated. The resulting residue was purified by silica gel column chromatography to give 2.55 g of N-(3-ethyl-4-methoxybenzyl)phthalimide.

0.84 ml hydrazine monohydrate was added to a mixture of 2.55 g N-(3-ethyl-4-methoxybenzyl)phthalimide and 60 ml ethanol, and the mixture was heated under reflex for 1 hr. After cooling, it was evaporated, and 2 N aqueous sodium hydroxide was added to the resulting residue which was then extracted with dichloromethane. The extract was dried over anhydrous magnesium sulfate and filtered. The filtrate was evaporated, ethyl acetate was added thereto, and then the insoluble matters were filtered. 4 N hydrochloric acid (solution in ethyl acetate) was added thereto, and the resulting crystals were collected by filtration to give 1.75 g of 3-ethyl-4-methoxybenzylamine hydrochloride.

1,4-Dichlorophthalazine-6-carbonitrile and 3-ethyl-4-methoxybenzylamine hydrochloride were stirred at room temperature in 1-methyl-2-pyrrolidinone in the presence of DBU, whereby 1-chloro-4-[(3-ethyl-4-methoxybenzyl) amino]-6-phthalazine carbonitrile was obtained as a less polar compound.

$^1$H-NMR (400 MHz, CDCl$_3$) δ; 1.14 (3H, t, J=7.5 Hz), 2.60 (2H, q, J=7.5 Hz), 3.81 (3H, s), 4.84 (2H, s), 6.80 (1H, d, J=8.2 Hz), 7.25 (1H, d, J=2.0 Hz), 7.30 (1H, dd, J=2.0, 8.2 Hz), 8.06 (1H, d, J=9.0 Hz), 8.27 (1H, d, J=9.0 Hz), 8.42 (1H, m).

INTERMEDIATE PRODUCTION EXAMPLE 7

1-Chloro-4-[(3-chloro-4-methylbenzyl)amino]-6-phthalazinecarbonitrile 15 ml solution of 2.0 g 3-chloro-4-methylbenzonitrile in tetrahydrofuran was added dropwise into 40 ml solution of 453 mg lithium aluminum hydride in tetrahydrofuran in a nitrogen atmosphere. The mixture was heated under reflux for 2 hr and 10 min. The mixture was ice-cooled, and 0.45 ml water, 0.45 ml of 15% aqueous sodium hydroxide, and 1.35 ml water were added dropwise thereinto such that the solution was kept at 10° C. or less. The solution was filtered through Celite, and the resulting filtrate was dried by adding anhydrous sodium sulfate. It was filtered through a NH-form silica gel, and the filtrate was evaporated to give 1.74 g of 3-chloro-4-methylbenzylamine.

1,4-Dichlorophthalazine-6-carbonitrile and 3-chloro-4-methylbenzylamine were stirred at room temperature in 1-methyl-2-pyrrolidinone in the presence of DBU, whereby the title compound was obtained as a less polar compound.

$^1$H-NMR (400 MHz, DMSO-d$_6$) δ; 2.29 (3H, s), 4.73 (2H, d, J=5.2 Hz), 7.28–7.32 (2H, m), 7.45 (1H, d, J=0.8 Hz), 8.20 (1H, dd, J=8.4, 0.4 Hz), 8.34 (1H, d, J=8.4, 1.6 Hz), 8.52 (1H, t, J=5.2 Hz), 9.00 (1H, m).

INTERMEDIATE PRODUCTION EXAMPLE 8

1-Chloro-4-[(4-chloro-3-methoxybenzyl)amino]-6-phthalazinecarbonitrile

4-Chloro-3-methoxybenzylamine benzylamine hydrochloride synthesized according to the method described in WO9518097 and 1,4-dichlorophthalazine-6-carbonitrile were stirred at room temperature in 1-methyl-2-pyrrolidinone in the presence of DBU, whereby 1-chloro-4-[(4-chloro-3-methoxybenzyl)amino]-6-phthalazine carbonitrile was obtained as a less polar product.

$^1$H-NMR (400 MHz, DMSO-d$_6$) δ; 3.86 (3H, s), 4.76 (2H, d, J=5.5 Hz), 4.74 (1H, d, J=4.2 Hz), 6.99 (1H, dd, J=1.8, 8.1 Hz), 7.22 (1H, d, J=1.8 Hz), 7.35 (1H, d, J=8.1 Hz), 8.21 (1H, d, J=8.6 Hz), 8.36 (1H, d, J=8.6 Hz), 8.52 (1H, t, J=5.5 Hz), 9.03 ((H, s).

INTERMEDIATE PRODUCTION EXAMPLE 9

1-Chloro-4-[(3,4-dichlorobenzyl)amino]-6-phthalazinecarbonitrile $^1$H-NMR (400 MHz, DMSO-d$_6$) δ; 4.76 (2H, d, J=5.4 Hz), 7.40 (1H, dd, J=8.4, 1.8 Hz), 7.58 (1H, d, J=8.4 Hz), 7.68 (1H, d, J=1.8 Hz), 8.21 (1H, dd, J=8.4, 0.4 Hz), 8.36 (1H, dd, J=8.4, 1.6 Hz), 8.57 (1H, t, J=5.4 Hz), 8.99 (1H, d, J=1.6 Hz).

INTERMEDIATE PRODUCTION EXAMPLE 10

Benzyl 4-Fluoro-4-hydroxymethyl-1-piperidinecarboxylate

51.1 g of methyltoluphenylphosphonium bromide was added to a mixture of 16.1 g tert-butoxy potassium and 500 ml tetrahydrofuran, and then stirred for 1 hr and 20 min at room temperature. 16.1 g of benzyl 4-oxo-1- piperidinecarboxylate was added thereto, and the mixture was stirred for 2 hr and 40 min at room temperature. The reaction solution was evaporated, diethyl ether was added thereto, and then filtered through Celite. The filtrate was washed with water and brine, dried over anhydrous magnesium sulfate, and then filtered. The filtrate was evaporated, and the resulting residue was subjected to silica gel column chromatography to give 25.5 g of benzyl 4-methylene-1-piperidinecarboxylate.

14.7 g of benzyl 4-methylene-1-piperidinecarboxylate was dissolved in 300 ml methanol, 20.4 g of phthalic acid monoperacid magnesium salt and 13.3 g of sodium bicarbonate were added thereto, and the mixture was stirred at room temperature for 7.5 hr. The reaction solution was evaporated. Ethyl acetate was added to the resulting residue which was then washed with water and brine, dried over anhydrous magnesium sulfate, and then filtered. The filtrate was evaporated, and then subjected to silica gel column chromatography to give 11.3 g of benzyl 1-oxa-6-azaspiro[2.5]octane-6-carboxylate.

A mixture of 5 ml hydrogen fluoride pyridine and 20 ml methylene chloride was cooled, and 10 ml solution of 4.95 g of benzyl 1-oxa-6-azaspiro[2.5]octane-6-carboxylate in methylene chloride was added dropwise thereinto over 25 min such that the bulk temperature was 0° C. or less. The mixture was stirred for 35 min under ice-cooling. The reaction solution was poured into a mixture of saturated sodium bicarbonate and ice. The organic layer was recovered, dried over anhydrous magnesium sulfate, and filtered. The filtrate was evaporated, and then subjected to silica gel column chromatography to give 2.84 g of the title compound.

INTERMEDIATE PRODUCTION EXAMPLE 11 tert-Butyl 4-Hydroxy-4-(1H-1-imidazolylmethyl)-1-piperidinecarboxylate

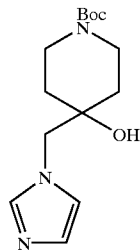

13.5 g of tert-butyl 4-methylene-1-piperidinecarboxylate was dissolved in 300 ml methanol, and 28.3 g phthalic acid monoperacid magnesium salt and 8.62 g sodium bicarbonate were added thereto, and the mixture was stirred at room temperature for 1 day. The reaction solution was filtered through Celite, and the resulting filtrate was evaporated. Ethyl acetate was added to the resulting residue which was then washed with water and brine, dried over anhydrous magnesium sulfate, and then filtered. The filtrate was evaporated, and subjected to silica gel column chromatography to give 12.2 g of tert-butyl 1-oxa-6-azaspiro[2.5]octane-6-carboxylate.

4.25 g of tert-butyl 1-oxa-6-azaspiro[2.5]octane-6-carboxylate was dissolved in 30 ml dimethylformamide, 5.38 g of sodium imidazole was added thereto, and the mixture was stirred at 60° C. for 3 hr and 40 min. After cooling, ethyl acetate was added to the reaction solution, and it was washed with water for 3 times and then with brine, dried over anhydrous magnesium sulfate, and filtered. The filtrate was evaporated and subjected to silica gel column chromatography to give 4.93 g of tert-butyl 4-hydroxy-4-(1H-1-imidazolylmethyl)-1-piperidinecarboxylate.

INTERMEDIATE PRODUCTION EXAMPLE 12 tert-Butyl 4-Hydroxy-4-(1H-1,2,4-triazole-1-ylmethyl)-1-piperidinecarboxylate

The title compound was obtained by using 1,2,4-triazole sodium in place of imidazole sodium in Intermediate Production Example 11.

INTERMEDIATE PRODUCTION EXAMPLE 13

Benzyl 4-Fluoromethyl-4-hydroxy-1-piperidinecarboxylate 3.2 g of potassium hydrogen fluoride and 610 mg tetra-n-butyl ammonium dihydrogen trifluoride were added to 5 g of benzyl 1-oxa-6-azaspiro[2.5]octane-6-carboxylate, and it was stirred at 120° C. for 7 hr. After cooling, methylene chloride was added thereto and it was filtered through Celite. The filtrate was evaporated, and the resulting residue was subjected to silica gel column chromatography to give 4.7 g of the title compound.

INTERMEDIATE PRODUCTION EXAMPLE 14

4-Hydroxy-4-piperidinecarboxamide Hydrochloride

A mixed solution of 18 ml conc. sulfuric acid and 1.8 ml water was cooled to 0° C., and 5 g of 1-benzyl-4-hydroxy-4-piperidinecarbonitrile hydrochloride was added thereto little by little. A mixed solution of 25 ml conc. sulfuric acid and 2.5 ml water was added thereto, and stirred at room temperature for 2 hr. It was left overnight in a freezer. The reaction solution was poured onto ice, and 47 g of sodium hydroxide was added thereto little by little. It was extracted 3 times with a mixed solvent of tetrahydrofuran and ethyl acetate (1:1). The extract was washed with brine, dried over anhydrous magnesium sulfate, and then filtered. The filtrate was evaporated and subjected to silica gel column chromatography to give 3.19 g of 1-benzyl-4-hydroxy-4-piperidine carboxamide.

3.19 g of 1-benzyl-4-hydroxy-4-piperidine carboxamide was dissolved in 150 ml methanol, and 1.5 g of 20% hydrous palladium hydroxide was added thereto. The mixture was shaken for 4 hr in a hydrogen atmosphere at 4 atmospheric pressure. The reaction solution was filtered through Celite, and 5 ml of 4 N HCl-dioxane was added to the filtrate which was then evaporated. The resulting crystalline residue was washed with diisopropyl ether and collected by filtration to give 1.96 g of the title compound.

INTERMEDIATE PRODUCTION EXAMPLE 15

N-(3-Chloro-4-methoxybenzyl)-N-[4-chloro-7-(1H-1-pyrazolyl)-1-phthaladinyl]amine

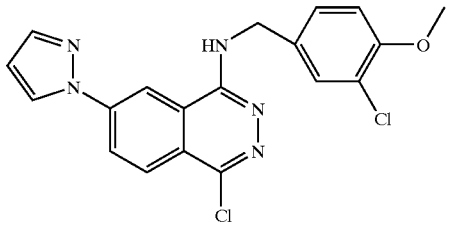

110 ml thionyl chloride was added dropwise over 30 min to a mixture of 100 g 4-fluorophthalic anhydride and 1500 ml methanol. The mixture was heated under reflux for 8 hr and evaporated. Ice water was added to the resulting residue which was then extracted with ethyl acetate. The extract was washed with brine, dried over anhydrous magnesium sulfate, and filtered. The filtrate was evaporated to give 125 g of dimethyl 4-fluorophthalate.

26 g of oily sodium hydride was added over 40 min to 200 ml solution of 44 g pyrazole in 1-methyl-2-pyrrolidinone. 125 g of dimethyl 4-fluorophthalate was added thereto over 30 min and stirred at room temperature for 2 hr. The reaction solution was cooled to 0° C. and added to ice water. It was extracted with ethyl acetate, and washed with saturated sodium bicarbonate and brine. It was dried over anhydrous magnesium sulfate and filtered. The filtrate was evaporated, and diethyl ether was added to the resulting crystalline residue which was then collected by filtration to give 77 g of dimethyl 4-(1H-1-pyrazolyl)phthalate.

22 ml hydrazine monohydrate was added to a mixture of 77 g dimethyl 4-(1H-1-pyrazolyl)phthalate and 500 ml ethanol, and heated under reflux for 6 hr. After cooling, the resulting precipitates were collected by filtration to give 36 g of 6-(1H-1-pyrazolyl)-1,4-phthalazine dione.

15 ml diisopropyl ethylamine was added to a mixture of 5.0 g 6-(1H-1-pyrazolyl)-1,4-phthalazine dione and 20 ml phosphorus oxychloride, and the mixture was stirred at 110° C. for 0.5 hr. The reaction solution was cooled at 0° C., ethyl acetate was added thereto, and further ice and water were added thereto little by little. The reaction solution was stirred at 0° C. for 0.5 hr, and the insoluble matters were removed by filtration. The ethyl acetate layer was recovered, washed with brine, dried over anhydrous magnesium sulfate, and filtered. The filtrate was evaporated, and ethyl acetate was added to the resulting crystalline residue which was then collected by filtration to give 3.8 g of 1,4-dichloro-6-(1H-1-pyrazolyl)phthalazine.

14 ml DBU was added to a mixture of 8 g 1,4-dichloro-6-(1H-1-pyrazolyl)phthalazine, 9.5 g of 3-chloro-4-methoxybenzylamine hydrochloride and 30 ml 1-methyl-2-pyrrolidinone, and the mixture was stirred at room temperature for 1 hr. It was further stirred at 60° C. for 3 hr. The reaction solution was cooled to 0° C., ethyl acetate was added thereto, followed by washing with water and brine. It was dried over anhydrous magnesium sulfate, filtered, and the filtrate was evaporated. The resulting residue was purified by silica gel column chromatography, whereby 2.6 g of the title compound was obtained as a less polar compound.

$^1$H-NMR (400 MHz, DMSO-d$_6$) δ; 3.80 (3H, s), 4.68 (2H, d, J=6.0 Hz), 6.70 (1H, t, J=2.0 Hz), 7.09 (1H, d, J=8.8 Hz), 7.35 (1H, dd, J=2.0, 8.4 Hz), 7.47 (1H, d, J=2.0 Hz), 7.91 (1H, d, J=2.0 Hz), 8.18 (1H, d, J=9.2 Hz), 8.32 (1H, t, J=5.6 Hz), 8.50 (1H, dd, J=2.0, 8.8 Hz), 8.68 (1H, d, J=2.4 Hz), 8.78 (1H, d, J=2.0 Hz).

INTERMEDIATE PRODUCTION EXAMPLE 16

N-(3-Chloro-4-methoxybenzyl)-N-[4-chloro-7-(1H-1,2,3-triazole-1-yl)-1-phthalazinyl]amine The title compound was obtained in the same manner as in Example 15 except that 1,2,3-triazole was used in place of pyrazole.

$^1$H-NMR (400 MHz, CD$_3$OD) δ; 3.82 (3H, s), 4.72 (2H, s), 6.97 (1H, d, J=8.4 Hz), 7.34 (1H, dd, J=1.6, 8.4 Hz), 7.44 (1H, d, J=1.6 Hz), 7.99 (1H, d, J=1.2 Hz), 8.34 (1H, d, J=8.8 Hz), 8.52 (1H, dd, J=1.6, 8.8 Hz), 8.72 (1H, d, J=1.2 Hz), 8.81 (1H, d, J=2 Hz).

INTERMEDIATE PRODUCTION EXAMPLE 17

6-Bromo-1-chloro-4-[(3-chloro-4-methoxybenzyl) amino]phthalazine 96.9 ml hydrazine monohydrate was added to a mixture of 20 g 4-bromophthalic anhydride and 400 ml ethanol, and the mixture was heated under reflex for 8 hr. After cooling, the resulting precipitates were collected by filtration to give 28 g of 6-bromo-1,4-phthalazinedione.

15 ml diisopropyl ethylamine was added to a mixture of 6.8 g 6-bromo-1,4-phthalazinedione and 15 ml phosphorus oxychloride, and the mixture was heated under reflux for 1.5 hr. After cooling, the reaction solution was poured into ice water, stirred well, and extracted with methylene chloride. The aqueous layer was extracted with ethyl acetate. The combined extract was dried over anhydrous magnesium sulfate, and filtered. The filtrate was evaporated, and the resulting residue was subjected to silica gel column chromatography to give 4.3 g of 6-bromo-1,4-dichlorophthalazine.

5.2 ml DBU was added to a mixture of 3.8 g 6-bromo-1,4-dichlorophthalazine, 3.5 g 3-chloro-4-methoxybenzylamine hydrochloride and 30 ml 1-methyl-2-pyrrolidinone, and the mixture was stirred at 100° C. for 3 hr. After cooling, water was added to the reaction solution which was then extracted with ethylacetate. The extract was washed with brine. It was dried over anhydrous magnesium sulfate and filtered, and the filtrate was evaporated. The resulting residue was purified by silica gel column chromatography to give 1.8 g of the title compound as a less polar compound.

INTERMEDIATE PRODUCTION EXAMPLE 18

1-(1,1-Dimethyl-2-propynyl)-4-piperidinol 24 mg cuprous chloride and 15 mg copper powder were added to a mixed solution of 5 ml solution of 7.3 g 4-hydroxypiperidine in diethyl ether (5 ml) and water (2.5 ml) in a nitrogen atmosphere. The mixture was ice-cooled, and 2.5 ml solution of 2.7 ml 3-chloro-3-methyl-1-butyne in diethyl ether was added dropwise thereinto at a bulk temperature of 17 to 22° C. Then, it was stirred at room temperature overnight. Water was added thereto, and the resulting mixture was extracted with diethyl ether for 5 times. The organic layers were combined, and dried over potassium carbonate and then over potassium hydroxide, and filtered. The filtrate was concentrated at normal pressure. The resulting crystalline residues were collected by filtration by adding ethyl acetate/hexane thereto to give 2.54 g of the title compound.

INTERMEDIATE PRODUCTION EXAMPLE 19

1-(1,1-Dimethyl-2-propynyl)pyrrolidine

The title compound was obtained from pyrrolidine and 3-chloro-3-methyl-1-butyne in the same manner as in Intermediate Production Example 18.

INTERMEDIATE PRODUCTION EXAMPLE 20

(2R)-1-oxa-8-Azaspiro[4.5]deca-2-yl Methanol 105.5 g of (5S)-5-(hydroxymethyl)tetrahydro-2-furanone was dissolved in 1.2 L pyridine, and 380 g of trityl chloride was added thereto at room temperature, and the mixture was stirred at 80° C. overnight. After the reaction was completed, the mixture was cooled, water was added thereto, extracted with ethyl acetate, and then washed with brine. The solvent was removed, and the resulting residue was dissolved in 300 ml chloroform, and after 600 ml silica gel was added thereto, the solvent was removed. The resulting residue was purified by silica gel column chromatography to give 149.3 g of (5S)-5-[(trityloxy)methyl]tetrahydro-2-furanone.

26.9 g of (5S)-5-[(trityloxy)methyl]tetrahydro-2-furanone was dissolved in 200 ml THF, 300 ml solution of 1 M vinylmagnesium bromide in THF was added thereto at room temperature, and it was stirred for 1.5 hr under heating and reflux. After the reaction was completed, saturated aqueous ammonium chloride was added thereto under ice-cooling, extracted with ethyl acetate, and then washed twice with brine. The solvent was removed and the resulting residue was purified by silica gel column chromatography to give 13.0 g of (2S)-1-(trityloxy)-5-vinyl-6-heptene-2,5-diol.

13.0 g of (2S)-1-(trityloxy)-5-vinyl-6-heptene-2,5-diol and 57.2 g of toluenesulfonyl chloride were dissolved in 200 ml pyridine, and stirred at 80° C. overnight. After the reaction was completed, water was added thereto, and it was stirred at room temperature for 10 min. After extracting twice with ethyl acetate, washed with brine, and dried over magnesium sulfate. The solvent was removed, and the resulting residue was dissolved in toluene. After the solvent was removed again, the resulting residue was purified by silica gel column chromatography to give 5.88 g of (5R)-5-[(trityloxy)methyl]-2,2-divinyltetrahydrofuran.

4.68 g of (5R)-5-[(trityloxy)methyl]-2,2-divinyltetrahydrofuran, 100 ml of 0.5 M 9-BBN and 6.1 g of 9-BBN dimer were suspended in 100 ml THF, and stirred for 30 hr under heating and reflux. After cooling, 50 ml of 30% hydrogen peroxide and 50 ml of 3 N sodium hydroxide were added thereto under ice-cooling, and stirred at 50° C. for 20 hr. After the reaction was completed, the reaction solution was returned to room temperature, extracted with ethyl acetate, washed with brine, and dried over magnesium sulfate. The solvent was removed, and the resulting residue was purified by silica gel column chromatography to give 2.68 g of 2-(5R)-2-(2-hydroxyethyl)-5-[(trityloxy)methyl] tetrahydro-2-furanyl-1-ethanol.

2.68 g of 2-(5R)-2-(2-hydroxyethyl)-5-[(trityloxy) methyl]tetrahydro-2-furanyl-1-ethanol and 12 ml pyridine were dissolved in 30 ml dichloromethane, and 11.82 g of toluenesulfonyl chloride was added thereto under ice-cooling and stirred for 2.5 hr. After the reaction was completed, 30 ml pyridine was added thereto, and then it was concentrated. After pyridine and water were added thereto again under ice-cooling, the mixture was stirred for 15 min. It was extracted with ethyl acetate, washed with brine, and then dried over magnesium sulfate. The solvent was distilled off, toluene was added thereto, the solvent was distilled off again, and then the resulting residue was purified by silica gel column chromatography to give 4.17 g of 2-(5R)-2-[2-[(4-methylphenyl)sulfonyl]oxyethyl]-5-[(trityloxy)methyl]tetrahydro-2-furanylethyl 4-methyl-1-benzene sulfonate.

4.17 g of 2-(5R)-2-[2-[(4-methylphenyl)sulfonyl] oxyethyl]-5-[(trityloxy)methyl]tetrahydro-2-furanylethyl 4-methyl-1-benzene sulfonate and 5.36 g of benzylamine were dissolved in 80 ml DMF, and stirred at 110° C. for 11.5 hr. After the reaction was completed, water was added thereto, extracted with ethyl acetate, and washed twice with brine and saturated aqueous sodium bicarbonate. After it was dried over magnesium sulfate, the solvent was removed, and the resulting residue was purified by silica gel column chromatography to give 2.1 g of (2R)-8-benzyl-2-[(trityloxy)methyl]-1-oxa-8-azaspiro[4.5]decane.

2.10 g of (2R)-8-benzyl-2-[(trityloxy)methyl]-1-oxa-8-azaspiro[4.5]decane was dissolved in 20 ml THF, 8 ml of 4 N hydrochloric acid in 1,4-dioxane was added thereto under ice-cooling, and then it was stirred for 1 hr. After the reaction was completed, water and saturated aqueous sodium bicarbonate were added thereto, extracted twice with ethyl acetate, washed with saturated aqueous sodium bicarbonate and brine, and then dried over magnesium sulfate. The solvent was removed and the resulting residue was purified by silica gel column chromatography to give 1.03 g of [(2R)-8-benzyl-1-oxa-8-azaspiro[4.5]deca-2-yl]methanol.

1.03 g of [(2R)-8-benzyl-1-oxa-8-azaspiro[4.5]deca-2-yl) methanol and 0.45 g of 10% palladium carbon were suspended in 30 ml ethanol, and stirred at room temperature for 18 hr in a hydrogen atmosphere at 1 atmospheric pressure. The insoluble matters were removed by filtration, the solvent was removed, and dried to give 0.76 g of the title compound.

INTERMEDIATE EXAMPLE 21

800 ml solution of 25.0 g tert-butyl 4-oxo-1-piperidinecarboxylate in diethyl ether was cooled in ice/methanol, and 138 ml solution of allylmagnesium bromide (1 M in diethyl ether) was added dropwise thereinto. The reaction mixture was stirred for 3 hr and 10 min. The reaction solution was poured into a mixture of saturated aqueous ammonium chloride and ice. The diethyl ether layer was recovered and washed with brine. It was dried over anhydrous magnesium sulfate, and then filtered. The filtrate was evaporated, and the resulting residue was purified by silica gel column chromatography to give 15.9 g of tert-butyl 4-allyl-4-hydroxy-1-piperidinecarboxylate.

9.83 g of tert-butyl 4-allyl-4-hydroxy-1-piperidinecarboxylate was dissolved in 60 ml tetrahydrofuran/water (9:1), a solution (2.5 wt %, 2 ml) of osmium tetraoxide in tert-butyl alcohol and 6.68 g of N-methylmorpholine-N-oxide were added thereto, and the mixture was stirred at room temperature overnight. The reaction solution was evaporated, and the resulting residue was partitioned into ethyl acetate and water, washed with brine and dried over magnesium sulfate. After filtration, the solvent was evaporated, and the resulting residue was purified by silica gel column chromatography (ethyl acetate/methanol) to give 9.11 g of tert-butyl 4-(2,3-dihydroxypropyl)-4-hydroxy-1-piperidinecarboxylate.

9.11 g of tert-butyl 4-(2,3-dihydroxypropyl)-4-hydroxy-1-piperidinecarboxylate was dissolved in 40 ml pyridine, 10.0 g of chlorotriphenylmethane was added thereto, and the mixture was stirred at room temperature overnight. The reaction solution was partitioned into ethyl acetate and water, washed with 2 N hydrochloric acid, water, saturated aqueous sodium bicarbonate and brine, and dried over magnesium sulfate. After filtration, the solvent was evaporated, and the resulting residue was purified by silica gel column chromatography (hexane/ethyl acetate) to give 10.3 g of tert-butyl 4-[3-(tert-butoxy)-2-hydroxypropyl]-4-hydroxy-1-piperidinecarboxylate.

2.59 g of tert-butyl 4-[3-(tert-butoxy)-2-hydroxypropyl]-4-hydroxy-1-piperidinecarboxylate was dissolved in 10 ml dimethylformamide, 400 mg of sodium hydride and 823 mg of benzyl chloride were added thereto, and the mixture was stirred at room temperature for 20 min. The reaction solution was poured into ice water, extracted with ethyl acetate, washed with water and brine, and dried over magnesium sulfate. After filtration, the solvent was evaporated, and the resulting residue was-purified by silica gel column chromatography (hexane/ethyl acetate) to give 2.66 g of tert-butyl 4-(2-(benzyloxy)-3-(tert-butoxy)propyl]-4-hydroxy-1-piperidinecarboxylate.

2.36 g of tert-butyl 4-[2-(benzyloxy)-3-(tert-butoxy) propyl]-4-hydroxy-1-piperidinecarboxylate was dissolved in 40 ml acetonitrile, 426 mg of cerium ammonium nitrate was added thereto, and the mixture was stirred at room temperature overnight. Silica gel was added to the reaction solution, and then it was evaporated. It was purified by adsorptive silica gel charged in a non-adsorptive silica gel column with hexane-ethyl acetate to give 547 mg of tert-butyl 4-[2-(benzyloxy)-3-hydroxypropyl]-4-hydroxy-1-piperidinecarboxylate.

4.81 g of tert-butyl 4-[2-(benzyloxy)-3-hydroxypropyl]-4-hydroxy-1-piperidinecarboxylate was dissolved in 20 ml pyridine, 2.76 g of tosyl chloride was added thereto, and the mixture was stirred at room temperature for 2 hr. Further, 1.00 g of tosyl chloride was added thereto, and the mixture was stirred at room temperature for 30 min, and at 50° C. for 35 min. The reaction solution was partitioned into ethyl acetate and water, washed with 1 N hydrochloric acid, saturated aqueous sodium bicarbonate and brine, and dried over magnesium sulfate. After filtration, the solvent was evaporated, and the resulting residue was purified by silica gel column chromatography (hexane/ethyl acetate) to give 3.72 g of tert-butyl 3-(benzyloxy)-1-oxa-8-azaspiro[4.5]decane-8-carboxylate.

6.47 g of tert-butyl 3-(benzyloxy)-1-oxa-8-azaspiro[4.5]decane-8-carboxylate was dissolved in 100 ml tetrahydrofuran, 1.3 g palladium carbon was added thereto, and the mixture was stirred overnight in a hydrogen atmosphere. The catalyst was filtered off from the reaction solution, 1.3 g of palladium carbon was added thereto, and the solution was stirred overnight in a hydrogen atmosphere. The catalyst was filtered off from the reaction solution, 2.6 g of palladium carbon was added thereto, and the solution was stirred overnight in a hydrogen atmosphere at 4.2 atmospheric pressure. The catalyst was filtered off from the reaction solution, the solvent was evaporated, and the resulting residue was purified by silica gel column chromatography (ethyl acetate/methanol) to give 4.27 g of tert-butyl 3-hydroxy-1-oxa-8-azaspiro[4.5]decane-8-carboxylate.

INTERMEDIATE PRODUCTION EXAMPLE 22

(anti)-3-oxa-9-Azabicyclo[3.3.1]nonan-7-ol Hydrochloride 2.0 g of aluminum lithium hydride was suspended in 200 ml tetrahydrofuran, and a solution of 14.17 g of 9-methyl-3-oxa-9-azabicyclo[3.3.1]nonan-7-one dissolved in 20 ml tetrahydrofuran was added dropwise thereinto under ice-cooling. After stirred for 35 min, 2.0 ml water, 2.0 ml of 15% aqueous sodium hydroxide and 6.0 ml water were added to the reaction solution sequentially, and the mixture was stirred at room temperature. The reaction solution was filtered, and the solvent was evaporated. The resulting residue was dissolved in ethyl acetate and filtered through alumina. The solvent was evaporated to give 10.00 g of (anti)-9-methyl-3-oxa-9-azabicyclo[3.3.1]nonan-7-ol was obtained as a yellow wax.

10.0 g of (anti)-9-methyl-3-oxa-9-azabicyclo[3.3.1] nonan-7-ol was dissolved in 100 ml tetrahydrofuran, 10.7 ml triethylamine, 7.2 ml acetic anhydride and 0.77 g of 4-dimethylaminopyridine were added thereto, and the mixture was stirred at 50° C. overnight. The reaction solution was evaporated, and the reulsitng residue was dissolved in ethyl acetate and filtered through alumina. The filtrate was concentrated and purified by alumina column chromatography (solvent; n-hexane/ethyl acetate) to give 8.68 g of (anti)-3-oxa-9-azabicyclo[3.3.1]nonane-7-yl acetate as a pale yellow oil.

8.68 g of (anti)-3-oxa-9-azabicyclo[3.3.1]nonan-7-yl acetate was dissolved in 40 ml 1,2-dichloroethane, and 7.0 ml vinyl chloroformate were added thereto. The mixture was stirred at room temperature for 30 min, and then heated under reflux for 2 hr and 35 min. The reaction solution was evaporated and purified by silica gel column chromatography (solvent; n-hexane/ethyl acetate) to give 8.96 g of (anti)-3-oxa-9-vinyloxycarbonyl-9-azabicyclo[3.3.1]nonan-7-yl acetate as a pale yellow oil.

8.96 g of (anti)-3-oxa-9-vinyloxycarbonyl-9-azabicyclo [3.3.1]nonan-7-yl acetate was dissolved in 45 ml methanol, and 30 ml water and 7.3 g potassium carbonate were added thereto. The mixture was stirred at room temperature for 1 hr and 30 min, and further stirred at 50° C. for 30 min. The reaction solution was evaporated, then brine was added thereto and it was extracted with ethyl acetate. After dried over anhydrous magnesium sulfate, the solvent was evaporated, whereby 7.37 g of (anti)-3-oxa-9-vinyloxycarbonyl-9-azabicyclo[3.3.1]nonan-7-ol was obtained as a pale yellow oil. 17 ml of 4 N hydrogen chloride in dioxane was added to 7.37 g of (anti)-3-oxa-9-vinyloxycarbonyl-9-azabicyclo[3.3.1]nonane-7-ol, and the mixture was stirred at room temperature for 30 min. 40 ml ethanol was added to the reaction solution, and the mixture was heated under reflux for 1 hr. The solvent was evaporated, ethyl acetate was added to the resulting residue, and the resulting precipitates were collected by filtration, whereby 5.55 g of the title compound was obtained as white needles.

INTERMEDIATE PRODUCTION EXAMPLE 23

(syn)-3-Azabicyclo[3.2.1]octan-8-ol Hydrochloride

The title compound was obtained from 3-methyl-3-azabicyclo[3.2.1]octan-8-one in the same manner as in Intermediate Production Example 22.

INTERMEDIATE PRODUCTION EXAMPLE 24

(anti)-3-oxa-7-Azabicyclo[3.3.1]nonan-9-ol Hydrochloride

The title compound was obtained from 7-methyl-3-oxa-7-azabicyclo[3.3.1]nonan-9-one in the same manner as in Intermediate Production Example 22.

INTERMEDIATE PRODUCTION EXAMPLE 25

(anti)-9-Azabicyclo[3.3.1]nonan-3-ol Hydrochloride

The title compound was obtained from 9-methyl-9-azabicyclo[3.3.1]nonane-3-one in the same manner as in Intermediate Production Example 22.

INTERMEDIATE PRODUCTION EXAMPLE 26

(exo)-8-Azabicyclo[3.2.1]octane-3-ol Hydrochloride

The title compound was obtained after acetylation from (exo)-8-methyl-8-Azabicyclo[3.2.1]octan-3-ol in the same manner as in Intermediate Production Example 22.

INTERMEDIATE PRODUCTION EXAMPLE 27

(endo)-8-Azabicyclo[3.2.1]octan-3-ol Hydrochloride

The title compound was obtained after acetylation from (endo)-8-methyl-8-azabicyclo[3.2.1]octan-3-ol in the same manner as in Intermediate Production Example 22.

INTERMEDIATE PRODUCTION EXAMPLE 28

(anti)-3-Azabicyclo[3.3.1]nonan-9-ol Hydrochloride 1.0 g of aluminum lithium hydride was suspended in 100 ml tetrahydrofuran, and a solution of 7.00 g 3-methyl-3-azabicyclo[3.3.1]nonan-9-one dissolved in 20 ml tetrahydrofuran was added dropwise thereinto under ice-cooling. After stirring for 50 min, 1.0 ml water, 1.0 ml of 15% aqueous sodium hydroxide and 3.0 ml water were added to the reaction solution sequentially, and stirred at room temperature. After filtering the reaction solution, the solvent was evaporated, whereby 7.08 g pale yellow oil was obtained. The oil was dissolved in 90 ml tetrahydrofuran, 9.55 ml triethylamine was added thereto, and then the mixture was stirred under ice-cooling. 6.46 ml acetic anhydride and 0.56 g 4-dimethylaminopyridine were added thereto, and the mixture was stirred at room temperature for 14 hr. About 20 ml methanol was added thereto, then the reaction solution was evaporated. An aqueous potassium carbonate was added to the residue which was then extracted with ethyl acetate. The organic layer was washed with water and brine, and then dried over anhydrous sodium sulfate. The solvent was evaporated, and the resulting residue was purified by silica gel column chromatography (solvent; n-hexane/ethyl acetate) to give 3.33 g of (anti)-3-methyl-3-azabicyclo[3.3.1]nonan-9-yl acetate (a colorless oil) as a less polar compound. Further, 2.06 g of (syn)-3-methyl-3-azabicyclo[3.3.1]nonan-9-yl acetate (a pale orange oil) was obtained as a more polar compound.

2.06 g of (anti)-3-methyl-3-azabicyclo[3.3.1]nonan-9-yl acetate was dissolved in 10 ml 1,2-dichloroethane, 2.07 ml vinyl chloroformate was added thereto, and the mixture was stirred at room temperature for 50 min. Then, it was heated under reflux for 5 hr and 25 min. The reaction solution was evaporated, and water was added to the residue which was then extracted with ethylacetate. The organic layer was washed with 1 N hydrochloric acid, saturated sodium bicarbonate and brine, and dried over anhydrous magnesium sulfate. The solvent was evaporated to give 2.51 g of (anti)-3-vinyloxycarbonyl-3-azabicyclo[3.3.1]nonan-9-yl acetate as a pale orange oil.

4.02 g of (anti)-3-vinyloxycarbonyl-3-azabicyclo[3.3.1]nonan-9-yl acetate was dissolved in 36 ml ethanol, 18 ml of 1 N aqueous sodium hydroxide was added thereto, and then the mixture was stirred at room temperature for 1 hr and 50 min. The reaction solution was evaporated, and water was added to the resulting residue which was then extracted with ethyl acetate. The organic layer was washed with water, saturated aqueous sodium bicarbonate and brine, and dried over anhydrous magnesium sulfate. The solvent was evaporated, and then the resulting residue was purified by silica gel column chromatography (solvent; n-hexane/ethyl acetate) to give 3.09 g of (anti)-3-vinyloxycarbonyl-3-azabicyclo[3.3.1]nonan-9-ol as a fine yellow oil.

7 ml solution of 4 N hydrogen chloride/dioxane was added to 3.09 g of (anti)-3-vinyloxycarbonyl-3-azabicyclo[3.3.1]nonan-9-ol, and the mixture was stirred at room temperature for 50 min. The reaction solution was evaporated, and 30 ml ethanol was added to the resulting residue which was then heated under reflux for 50 min. The solvent was evaporated, and then ethyl acetate was added to the resulting residue. The resulting precipitates were collected by filtration to give 2.41 g of the title compound as a fine milky white powder.

INTERMEDIATE PRODUCTION EXAMPLE 29

(syn)-3-Azabicyclo[3.3.1]nonan-9-ol Acid Salt

The title compound was obtained from (syn)-3-methyl-3-azabicyclo[3.3.1]nonan-9-yl acetate in the same manner as in Intermediate Production Example 28.

INTERMEDIATE PRODUCTION EXAMPLE 30

(anti)-2-(3-Azabicyclo[3.3.1]non-9-yl)-1-ethanol Hydrochloride 1.0 g of aluminum lithium hydride was suspended in 30 ml tetrahydrofuran, and 25 ml suspension of 3.24 g (anti)-methyl (3-azabicyclo[3.3.1]non-9-yl)acetate in tetrahydrofuran was added dropwise thereinto under ice-cooling. After stirring for 35 min, 1.0 ml water, 1.0 ml of 15% aqueous sodium hydroxide and 3.0 ml water were added to the reaction solution sequentially, and stirred at room temperature. The reaction solution was filtered by adding Celite and anhydrous sodium sulfate, and the solvent was evaporated. The residue was dissolved in ethyl acetate, 5 ml of 4 N hydrogen chloride/ethyl acetate was added thereto, and the resulting precipitates were collected by filtration to give 2.29 g of the title compound as a white powder.

INTERMEDIATE PRODUCTION EXAMPLE 31

1-Chloro-4-[(4-methoxy-3-methylbenzyl)amino]-6-phthalazine Carbonitrile $^1$H-NMR (400 MHz, DMSO-$d_6$) δ; 2.10 (3H, s), 3.73 (3H, s), 4.64 (2H, d, J=5.4 Hz), 6.85 (1H, d, J=8.0 Hz), 7.17–7.21 (2H, m), 8.15 (1H, d, J=8.6 Hz), 8.31 (1H, dd, J=8.6, 1.2 Hz), 8.35 (1H, t, J=5.4 Hz), 9.00 (1H, d, J=1.2 Hz).

EXAMPLE 1

4-(3-Chloro-4-methoxybenzyl)amino-6-cyano-1-(3-pyridyl)phthalazine Dihydrochloride

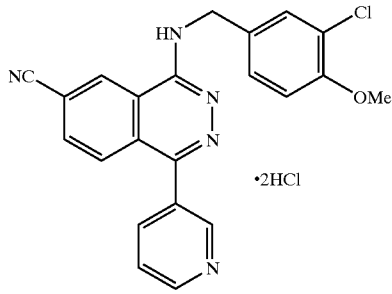

10 ml solution (1.6 M) of n-butyl lithium in hexane was added dropwise to 50 ml solution of 2.53 g 3-bromopyridine in anhydrous diethyl ether at −70° C. or less, and stirred for 30 min. 10 ml solution of 5.21 g of tri-n-butyltin chloride in anhydrous diethyl ether was added to the resulting mixture. The reaction solution was returned to room temperature over 1 hr. The reaction solution was poured into brine, and the organic layer was washed with brine. It was dried over anhydrous magnesium sulfate, and then evaporated to give 3-(1,1,1-tri-n-butylstannyl)pyridine as a yellow oil.

A mixture of 1.80 g 1-chloro-4-(3-chloro-4-methoxybenzyl)amino-6-cyanophthalazine, 579 mg tetrakis(triphenylphosphine)palladium, 25 ml xylene and 3 ml 1-methyl-2-pyrrolidone was vigorously stirred and heated under reflux, and 25 ml solution of 3-(1,1,1-tri-n-butylstannyl)pyridine obtained above in xylene was added dropwise thereto over 1 hr. The reaction solution was further heated under reflux for 15 min. The reaction solution was returned to room temperature, washed 3 times with water and once with brine. It was purified by silica gel column chromatography to give a coupled product. It was suspended in a mixed solvent of tetrahydrofuran and methanol, then a solution of 4 N hydrochloric acid/ethyl acetate was added thereto and the mixture was evaporated. The resulting product was recrystallized from ethyl acetate/methanol to give 1.80 g of the title compound as a colorless powder.

MASS (ESI); 402.0 (MH$^+$); $^1$H-NMR (400 MHz, DMSO-$d_6$) δ; 3.85 (3H, s), 4.06 (2H, br), 4.89 (2H, br), 7.18 (1H, d, J=8.0 Hz), 7.53 (1H, dd, J=8.0, 1.2 Hz), 7.67 (1H, d, J=1.2 Hz), 7.81–7.90 (1H, m), 8.07 (1H, dd, J=8.8, 0.4 Hz), 8.38–8.45 (1H, m), 8.46 (1H, dd, J=8.8, 1.4 Hz), 8.90–9.00 (2H, m), 9.57 (1H, dd, J=1.4, 0.4 Hz), 10.76 (1H, br).

EXAMPLE 2

4-(3-Chloro-4-methoxybenzyl)amino-6-cyano-1-(2-pyridyl)phthalazine Dihydrochloride

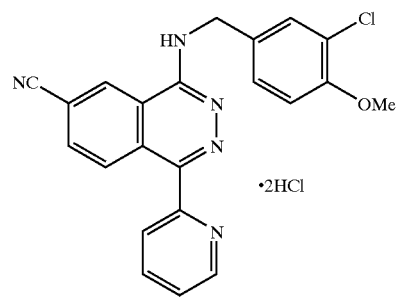

The title compound was obtained in the same manner as in Example 1 except that 2-bromopyridine was used in place of 3-bromopyridine.

MASS (ESI); 402.0 (MH$^+$); $^1$H-NMR (400 MHz, DMSO-$d_6$) δ; 3.83 (3H, s), 4.86–4.90 (2H, m), 7.16 (1H, d, J=8.6 Hz), 7.52 (1H, dd, J=8.6, 2.1 Hz), 7.63–7.69 (2H, m), 7.97 (1H, d, J=8.5 Hz), 8.08–8.13 (1H, m), 8.47 (1H, dd, J=8.5, 1.4 Hz), 8.72–8.83 (2H, m), 9.56 (1H, d, J=1.4 Hz), 10.82–10.92 (1H, m).

EXAMPLE 3

4-(3-Chloro-4-methoxybenzyl)amino-6-cyano-1-(4-cyanopiperidino)phthalazine Hydrochloride

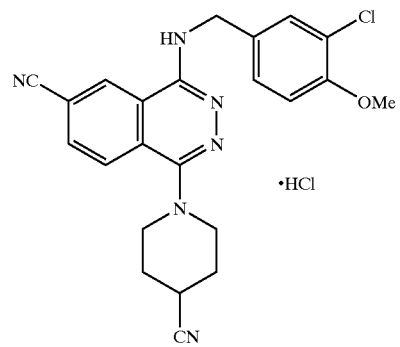

A mixture of 15 g 4-piperidinecarboxamide, 16.3 g benzyl chloride, 32.3 g potassium carbonate and 200 ml N,N- dimethylformamide was stirred at 80° C. for 4 hr. The reaction solution was returned to room temperature, and aqueous sodium hydroxide was added thereto, and then it was extracted with ethyl acetate. The organic layer was washed with brine, dried over anhydrous sodium sulfate, and then evaporated. The resulting crystalline residue was washed with hexane/ethyl acetate and collected by filtration. 12.7 g of 1-benzyl-4-piperidine carboxamide was obtained as white flaky crystals.

5 ml N,N-dimethylformamide was added to a mixture of 12.7 g 1-benzyl-4-piperidine carboxamide and 60 ml phosphorus oxychloride under ice-cooling, and it was stirred at room temperature for 1.5 hr. It was evaporated, and the resulting residue was dissolved in ethyl acetate and washed with aqueous sodium hydroxide and brine. After drying over anhydrous sodium sulfate, it was evaporated, and the resulting residue was purified by silica gel column chromatography to give 11.0 g of 1-benzyl-4-piperidine carbonitrile.

11.0 g of 1-benzyl-4-piperidinecarbonitrile was dissolved in 100 ml 1,2-dichloroethane, 7.1 ml 1-chloroethyl chloroformate was added thereto under ice-cooling. The mixture was stirred at room temperature for 15 min, and then heated under reflux for 1 hr and 20 min. After evaporating, 50 ml methanol was added thereto and it was heated under reflux for 1 hr. The reaction solution was evaporated, and the crystalline residue was washed with ethyl acetate and collected by filtration to give 8.0 g of 4-piperidinecarbonitrile hydrochloride as white crystals.

A mixture of 1.2 g of the resulting 4-piperidinecarbonitrile hydrochloride, 1.0 g 1-chloro-4-(3-chloro-4-methoxybenzyl)amino-6-cyanophthalazine, 1.8 g diisopropylethylamine, and 10 ml 1-methyl-2-pyrrolidone was stirred at 170° C. for 2 hr and 30 min. After cooling, ethyl acetate was added to the reaction solution which was then washed with water and brine. After it was dried over anhydrous sodium sulfate, the solvent was evaporated and the resulting residue was purified by silica gel column chromatography. The resulting free compound was dissolved in ethyl acetate, then a solution of 4 N hydrochloric acid/ethyl acetate was added thereto, and the resulting crystals were collected by filtration to give 880 mg of the title compound as a yellow powder.

MASS (ESI); 433.2 (MH$^+$); $^1$H-NMR (400 MHz, DMSO-d$_6$) δ; 1.98–2.17 (4H, m), 3.10–3.33 (5H, m), 3.86 (3H, s), 4.70–4.74 (2H, m), 7.17 (1H, d, J=8.4 Hz), 7.45 (1H, dd, J=8.4, 2.0 Hz), 7.61 (1H, d, J=2.0 Hz), 8.27 (1H, d, J=8.4 Hz), 8.47 (1H, dd, J=8.4, 0.8 Hz), 9.34–9.38 (1H, m), 10.28 (1H, br).

EXAMPLE 4

4-(3-Chloro-4-methoxyphenethyl)amino-6-cyano-1-(4-cyanopiperidino)phthalazine Hydrochloride

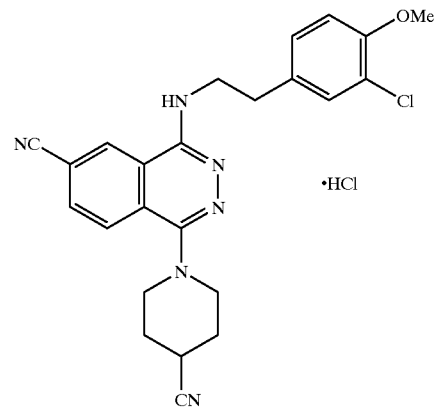

The title compound was obtained by using 1-chloro-4-(3-chloro-4-methoxyphenethyl)amino-6-cyanophthalazine in place of 1-chloro-4-(3-chloro-4-methoxybenzyl)amino-6-cyanophthalazine in Example 3.

MASS (ESI); 447.1 (MH$^+$); $^1$H-NMR (400 MHz, DMSO-d$_6$) δ; 1.97–2.18 (4H, m), 2.94–3.00 (2H, m), 3.11–3.23 (3H, m), 3.33–3.40 (2H, m), 3.72–3.80 (2H, m), 3.82 (3H, s), 7.09 (1H, d, J=8.4 Hz), 7.27 (1H, dd, J=8.4, 2.0 Hz), 7.44 (1H, d, J=2.0 Hz), 8.28 (1H, d, J=8.4 Hz), 8.47 (1H, dd, J=8.4, 0.8 Hz), 9.23–9.28 (1H, m), 9.85 (1H, br).

EXAMPLE 5

1-(4-Aminopiperidino)-4-(3-chloro-4-methoxybenzyl)amino-6-cyanophthalazine Dihydrochloride

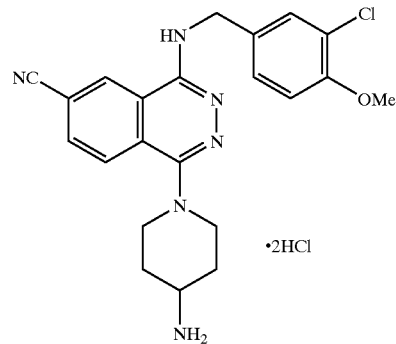

10.0 g of 1-chloro-4-(3-chloro-4-methoxybenzyl)amino-6-cyanophthalazine was dissolved in 50 ml 1-methyl-2-pyrrolidone, then 43.32 g of 4-hydroxypiperidine and 10 ml diisopropylethylamine were added thereto, and the mixture was heated at 170° C. for 8 hr. After cooling, ethyl acetate was added thereto, and the mixture was washed 3 times with water and once with brine. After drying over anhydrous magnesium sulfate, the solvent was evaporated. The resulting residue was purified by silica gel column chromatography to give 10.1 g of 1-(4-hydroxypiperidino)-4-(3-chloro-4-methoxybenzyl)amino-6-cyanophthalazine as yellow crystals.

Then, 30 ml solution of 3.48 g diethyl azodicarboxylate in tetrahydrofuran was added to 100 ml solution of 4.2 g 1-(4-hydroxypiperidino)-4-(3-chloro-4-methoxybenzyl)amino-6-cyanophthalazine, 2.94 g phthalimide, and 5.24 g triphenylphosphine in tetrahydrofuran over 30 min under ice-cooling, and then it was stirred at 4° C. for 24 hr. The reaction solution was evaporated, water and ethyl acetate were added thereto, and then the insoluble matters were removed by filtration. The organic layer was concentrated, and the resulting residue was purified by silica gel column chromatography to give 4.85 g of 4-(3-chloro-4-methoxybenzyl)amino-6-cyano-1-(4-phthalimidopiperidino)phthalazine.

A mixture of 4.85 g of the resulting 4-(3-chloro-4-methoxybenzyl)amino-6-cyano-1-(4-phthalimidopiperidino)phthalazine, 4 ml hydrazine monohydrate and 40 ml ethanol was heated under reflux for 1 hr. The reaction solution was evaporated, dissolved in ethyl acetate, and 1 N hydrochloric acid was added thereto to adjust the pH thereof to 3, and the insoluble matters were removed by filtration. The aqueous layer in the filtrate was adjusted to pH 11 with 1 N sodium hydroxide, and then extracted with ethyl acetate. The organic layer was washed with brine, dried over anhydrous sodium sulfate, evaporated, and then purified by silica gel column chromatography. The resulting product was suspended in ethanol/water, then 1 N aqueous hydrochloric acid was added thereto and dissolved by heating. After cooling, the resulting crystals were collected by filtration to give 440 mg of the title compound as a yellow powder.

MASS (FAB); 423 (MH$^+$); $^1$H-NMR (400 MHz, DMSO-d$_6$) δ; 1.78–1.92 (2H, m), 2.03–2.11 (2H, m), 2.90–3.0 (2H, m), 3.20–3.34 (1H, m), 3.54–3.63 (2H, m), 3.82 (3H, s), 4.70 (2H, d, J=5.6 Hz), 7.13 (1H, d, J=8.4 Hz), 7.47 (1H, dd, J=8.4, 2.0 Hz), 7.62 (1H, d, J=2.0 Hz), 8.17 (1H, d, J=8.4 Hz), 8.35–8.45 (2H, m), 8.47 (1H, dd, J=8.4, 1.0 Hz), 9.54 (1H, d, J=1.0 Hz), 10.63 (1H, br).

EXAMPLE 6

4-(3-Chloro-4-methoxybenzyl)amino-6-cyano-1-[4-hydroxy-4-(hydroxymethyl)piperidino]phthalazine Hydrochloride

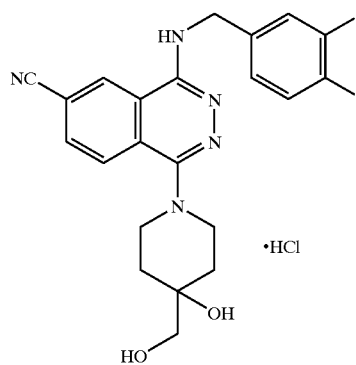

7.9 g of 60% sodium hydride was washed with hexane, followed by drying under reduced pressure. 100 ml dimethyl sulfoxide was added thereto and stirred at 80 to 100° C. for 30 min in a nitrogen atmosphere. It was ice-cooled and 180 ml tetrahydrofuran was added thereto. 150 ml solution of 4.37 g trimethylsulfonium iodide in dimethyl sulfoxide was added dropwise thereinto. After the mixture was stirred for 30 min under ice-cooling, 15 g of 1-benzyl-4-piperidone was added thereto, stirred for 30 min under ice-cooling, and then stirred at room temperature for 6 hr. Water was added to the reaction solution which was then extracted with ethyl acetate. The organic layer was washed with brine, and then dried over anhydrous sodium sulfate. It was purified by silica gel chromatography to give 6.8 g of 6-benzyl-1-oxo-6-azaspiro[2.5]octane.

100 ml water and 10 ml perchloric acid were added to 100 ml solution of 6.8 g of this 6-benzyl-1-oxo-6-azaspiro[2.5]octane in tetrahydrofuran, and the mixture was stirred at room temperature for 7 hr. The mixture was ice-cooled, and aqueous sodium carbonate was added thereto to adjust the pH thereof to 7, and then the mixture was evaporated. Ethyl acetate was added to the residue, and the insoluble mattters were removed by filtration. The filtrate was evaporated, and then purified by silica gel column chromatography to give 4 g of 1-benzyl-4-(hydroxymethyl)-4-piperidinol.

Then, 1.46 g of 1-benzyl-4-(hydroxymethyl)-4-piperidinol was dissolved in 30 ml methanol, 10 ml acetic acid and 10% Pd-C were added thereto, and then hydrogenated at 4 atmospheric pressure. The reaction solution was filtered through Celite, and the filtrate was evaporated and dissolved in methanol. 4 N hydrochloric acid/ethyl acetate was added thereto, and then it was concentrated. The resulting crystals crystallized from methanol/ethyl acetate were collected by filtration to give 880 mg of 4-(hydroxymethyl)-4-piperidinol hydrochloride.

The resulting 4-(hydroxymethyl)-4-piperidinol hydrochloride was reacted with 1-chloro-4-(3-chloro-4-methoxybenzyl)amino-6-cyanophthalazine in the same manner as in Example 4 to give the title compound.

MASS (FAB); 454.2 (MH$^+$); $^1$H-NMR (400 MHz, DMSO-d$_6$) δ; 1.46–1.54 (2H, m), 1.82–1.94 (2H, m), 3.16–3.30 (6H, m), 3.84 (3H, s), 4.68–4.72 (2H, m), 7.15 (1H, d, J=8.6 Hz), 7.44 (1H, dd, J=8.6, 2.0 Hz), 7.59 (1H, d, J=2.0 Hz), 8.22 (1H, d, J=8.6 Hz), 8.45 (1H, dd, J=8.6, 1.0 Hz), 9.36 (1H, d, J=1.0 Hz).

EXAMPLE 7

4-(3-Chloro-4-methoxybenzyl)amino-6-cyano-1-[(2S)-2-(methoxymethyl)pyrrolidino]phthalazine Hydrochloride

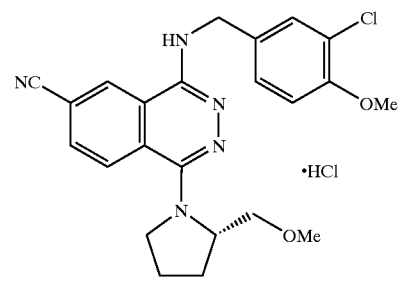

The title compound was obtained by using (S)-2-methoxymethylpyrrolidine in place of (R)-(+)-3-hydroxypiperidine hydrochloride in Production Example 1.

MASS (ESI); 438.1 (MH⁺); ¹H-NMR (400 MHz, DMSO-d₆) δ; 1.81–1.89 (2H, m), 1.95–2.03 (1H, m), 2.15–2.24 (1H, m), 3.16 (3H, s), 3.28–3.37 (1H, m), 3.46–3.58 (2H, m), 3.84 (3H, s), 3.87–3.98 (1H, m), 4.44–4.57 (1H, m), 4.62–4.78 (2H, m), 7.15 (1H, d, J=8.6 Hz), 7.47 (1H, dd, J=8.6, 0.4 Hz), 7.61 (1H, d, J=0.4 Hz), 8.41–8.51 (2H, m), 9.42–9.60 (1H, m), 10.50 (1H, br), 13.79 (1H, br).

EXAMPLE 8

4-(3-Chloro-4-methoxybenzyl)amino-6-cyano-1-phenylphthalazine Hydrochloride

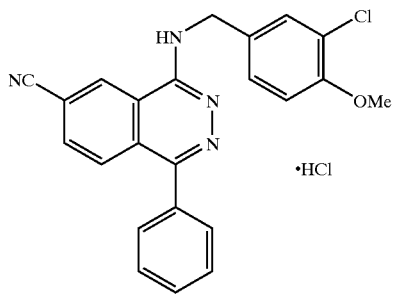

The title compound was obtained in the same manner as in Production Example 10 except that phenylboric acid was used in place of methoxyphenylboric acid.

MASS (ESI); 401.1 (MH⁺); ¹H-NMR (400 MHz, DMSO-d₆) δ; 3.84 (3H, s), 4.81–4.85 (2H, m), 7.15 (1H, d, J=8.6 Hz), 7.48 (1H, dd, J=8.6, 2.1 Hz), 7.60–7.66 (6H, m), 8.00 (1H, d, J=8.6 Hz), 8.41 (1H, dd, J=8.6, 0.9 Hz), 9.42 (1H, d, J=0.9 Hz).

EXAMPLE 9

4-[(3-Chloro-4-methoxybenzyl)amino]-1-(2-hydroxy-7-azaspiro[3.5]non-7-yl)-6-phthalazinecarbonitrile Hydrochloride

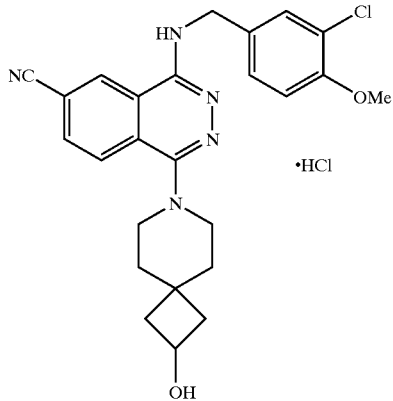

47.2 g of methyltoluphenylphosphonium bromide and 21.9 g of tert-butyl 4-oxo-1-piperidinecarboxylate were added to a mixture of 14.8 g tert-butoxy potassium and 300 ml tetrahydrofuran, and stirred for 40 min at room temperature. The reaction solution was evaporated, diethyl ether was added thereto, and then filtered through Celite. The filtrate was washed with water and brine; dried over anhydrous magnesium sulfate, and then filtered. The filtrate was evaporated, and the resulting residue was subjected to silica gel column chromatography to give 20.8 g of tert-butyl 4-methylene-1-piperidinecarboxylate.

49.3 g of tert-butyl 4-methylene-1-piperidine carboxylate was added to a mixture of 157.2 g zinc-copper alloy and 500 ml diethyl ether, and 900 ml solution of 181.8 g trichloroacetyl chloride in dimethoxyethane was added dropwise thereinto over 5.5 hours. After stirred for 30 min, the reaction solution was cooled and saturated aqueous sodium bicarbonate was added thereto at 0° C. or less. The mixture was filtered through Celite and evaporated. The resulting residue was extracted with ethyl acetate. The extract was washed with brine, dried over anhydrous magnesium sulfate, and filtered. The filtrate was evaporated, and the resulting residue was subjected to silica gel column chromatography to give 62.5 g of tert-butyl 1,1-dichloro-2-oxo-7-azaspiro[3.5]nonane-7-carboxylate.

106.1 g zinc dust was added to a mixture of 62.5 g tert-butyl 1,1-dichloro-2-oxo-7-azaspiro[3.5]nonane-7-carboxylate and 500 ml saturated ammonium chloride in methanol. The mixture was stirred for 1 hr and 20 min at room temperature and filtered through Celite. The filtrate was evaporated, 1 N hydrochloric acid/ethyl acetate was added thereto, and the organic layer was recovered. The extract was washed with water, saturated sodium bicarbonate and brine, dried over anhydrous magnesium sulfate, and filtered. The filtrate was evaporated, and the resulting residue was subjected to silica gel column chromatography to give 38.9 g of tert-butyl 2-oxo-7-azaspiro[3.5]nonane-7-carboxylate.

300 ml ethanol was ice-cooled, and 6.13 g of sodium borohydride was dissolved therein. 100 ml solution of 38.9 g of tert-butyl 2-oxo-7-azaspiro[3.5]nonane-7-carboxylate in ethanol was added dropwise thereinto over 25 min. The reaction solution was treated with saturated aqueous ammonium chloride and evaporated. The resulting residue was partitioned into ethyl acetate and water, and the ethyl acetate layer was washed with brine and dried over magnesium sulfate. After filtration, the solvent was evaporated, and the resulting residue was purified by silica gel column chromatography (hexane/ethyl acetate) to give 36.6 g of tert-butyl 2-hydroxy-7-azaspiro[3.5]nonane-7-carboxylate.

¹H-NMR (400 MHz, CDCl₃) δ; 1.45 (9H, s), 1.43–1.57 (4H, m), 1.65–1.72 (2H, m), 3.27–3.35 (4H, m), 4.32 (1H, quint, J=7.2 Hz).

6.22 g of tert-butyl 2-hydroxy-7-azaspiro[3.5]nonane-7-carboxylate was dissolved in 20 ml tetrahydrofuran, and 80 ml solution of 4 N hydrogen chloride/dioxane was added to the resulting solution, and then stirred at room temperature for 1 hr. The reaction solution was evaporated, and the resulting residue was dissolved in 20 ml 1-methyl-2-pyrrolidinone, 4.67 g of 1-chloro-4-[(3-chloro-4-methoxybenzyl)amino]-6-phthalazine carbonitrile and 6.72 g of diisopropylethylamine were added thereto, and then stirred at 160° C. for 9 hours. The reaction solution was returned to room temperature and partitioned into ethyl acetate and water, and the aqueous layer was extracted with ethyl acetate. The ethyl acetate layers were combined, and washed with water (5 times) and with brine sequentially, and dried over magnesium sulfate. After filtration, the solvent was evaporated, and the resulting residue was purified by silica gel column chromatography (ethyl acetate/methanol), and the resulting crude crystals were crushed and washed in diethyl ether to give 4.86 g yellow crystals. The resulting product was dissolved in 150 ml ethanol, 15 ml solution of 4 N hydrogen chloride/dioxane was added thereto, and the solvent was evaporated. The resulting residue was dissolved in 150 ml ethanol, heated to 80° C., and seeded with crystals separately synthesized in hydrous ethanol, and when crystallization was initiated, heating was terminated. After cooling as it stands to room temperature, collecting by filtration and washing with ethanol were conducted to give 4.35 g of the title compound.

$^1$H-NMR (400 MHz, DMSO-$d_6$) δ; 1.58–1.66 (2H, m), 1.68–1.76 (4H, m), 2.14–2.22 (2H, m), 3.05–3.16 (4H, m), 3.83 (3H, s), 4.12 (1H, t, J=7.2 Hz), 4.72 (2H, d, J=5.6 Hz), 7.14 (1H, d, J=8.8 Hz), 7.45 (1H, dd, J=8.8, 2.0 Hz), 7.60 (1H, d, J=2.0 Hz), 8.20 (1H, d, J=8.4 Hz), 8.44 (1H, dd, J=8.4, 1.2 Hz), 9.46 (1H, s).

EXAMPLE 10

4-[(3-Chloro-4-methoxybenzyl)amino]-1-(4-pyridyl)-6-phthalazine Carbonitrile

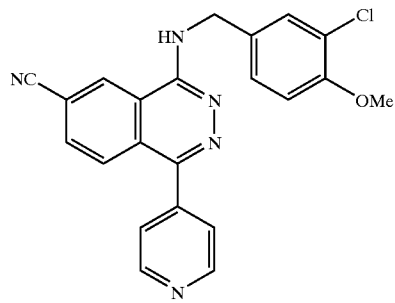

The title compound was obtained in the same manner as in Example 1.

$^1$H-NMR (400 MHz, DMSO-$d_6$) δ; 3.80 (3H, s), 4.76 (2H, d, J=5.5 Hz), 7.10 (1H, d, J=8.8 Hz), 7.38 (1H, dd, J=8.8, 2.4 Hz), 7.50 (1H, d, J=2.4 Hz), 7.64 (2H, d, J=5.6 Hz), 7.94 (1H, d, J=8.8 Hz), 8.20 (1H, d, J=8.8 Hz), 8.52 (1H, dd, J=5.5, 5.5 Hz), 8.73 (2H, d, J=5.6 Hz), 9.02 (1H, s).

EXAMPLE 11

4-[(3-Chloro-4-methoxybenzyl)amino]-1-(3-oxo-2-oxa-8-azaspiro[4.5]dece-8-yl)-6-phthalazine Carbonitrile

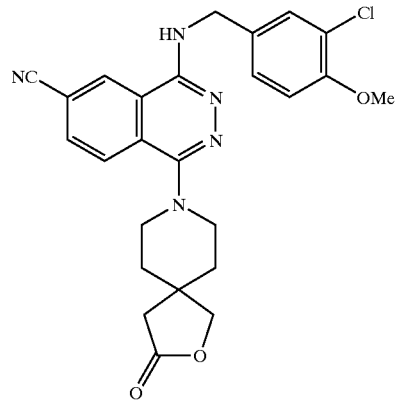

567 ml solution of 37.8 g tert-butyl 2-oxo-7-azaspiro[3.5]nonane-7-carboxylate in methanol was cooled on ice water, and 43 g of 30% aqueous hydrogen peroxide was added dropwise thereinto. 63 ml of 1 N aqueous sodium hydroxide was added dropwise thereto, and the mixture was stirred at room temperature for 2 hr. 1000 ml ethyl acetate, 600 ml water and 100 ml saturated aqueous sodium thiosulfate pentahydrate were added thereto, and the organic layer was recovered. The extracted solution was washed with brine, dried over anhydrous magnesium sulfate, and then filtered. The filtrate was evaporated to give 28.4 g of tert-butyl 3-oxo-2-oxa-8-azaspiro[4.5]decane-8-carboxylate.

1.16 g of tert-butyl 3-oxo-2-oxa-8-azaspiro[4.5]decane-8-carboxylate was dissolved in 2.3 ml methanol, 4.6 ml of 4 N hydrochloric acid/ethyl acetate was added thereto, and the mixture was stirred at room temperature for 1 hr. 5 ml ethyl acetate was added thereto, and the resulting crystals were collected by filtration to give 700 mg of 3-oxo-2-oxa-8-azaspiro[4.5]decane hydrochloride.

A mixture of 657 mg 1-chloro-4-[(3-chloro-4-methoxybenzyl)amino]-6-phthalazine carbonitrile, 700 mg 3-oxo-2-oxa-8-azaspiro[4.5]decane hydrochloride, 0.44 ml diethyl aniline, 137 mg sodium iodide, and 1.7 ml 1-methyl-2-pyrrolidinone was stirred at 130° C. for 15 hr and 40 min. After cooling, the reaction solution was diluted with 40 ml tetrahydrofuran, 100 ml ethyl acetate, and 15 ml 1-methyl-2-pyrrolidinone, and then washed with saturated aqueous sodium bicarbonate and brine. It was dried over anhydrous magnesium sulfate, and then filtered. The filtrate was evaporated and the resulting residue was purified by silica gel column chromatography to give 713 mg of 4-[(3-chloro-4-methoxybenzyl)amino]-1-(3-oxo-2-oxa-8-azaspiro[4.5]dece-8-yl)-6-phthalazinecarbonitrile.

¹H-NMR (400 MHz, CDCl₃) δ; 1.88–2.01 (4H, m), 2.53 (2H, s), 3.22–3.40 (4H, m), 3.90 (3H, s), 4.20 (2H, s), 4.77 (2H, d, J=5.2 Hz), 5.20 (1H, t, J=5.2 Hz), 6.92 (1H, d, J=8.4 Hz), 7.32 (1H, dd, J=8.4, 2.0 Hz), 7.46 (1H, d, J=2.0 Hz), 7.96 (1H, dd, J=8.4, 2.0 Hz), 8.11 (1H, d, J=8.4 Hz), 8.14 (1H, d, J=0.8 Hz).

EXAMPLE 12

4-[(3-Chloro-4-methoxybenzyl)amino]-1-(2-oxo-7-azaspiro[3.5]non-7-yl)-6-phthalazine Carbonitrile

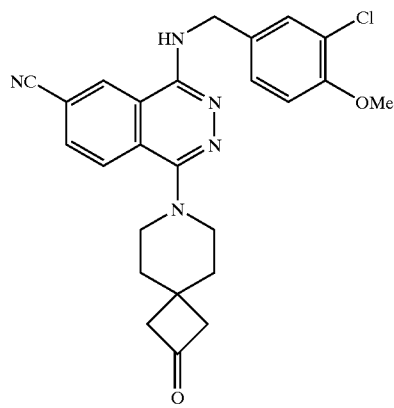

500 mg of 4-[(3-chloro-4-methoxybenzyl)amino]-1-(2-hydroxy-7-azaspiro[3.5]non-7-yl)-6-phthalazine carbonitrile was suspended in 20 ml dichloromethane and 10 ml tetrahydrofuran, then 690 mg of 1,1,1-triacetoxy-1,1-dihydro-1,2-benziodoxol-3(1H)-one was added thereto, and the mixture was stirred at room temperature for 15 min. Ethyl acetate, 30 ml saturated aqueous sodium bicarbonate and 2 ml saturated aqueous sodium thiosulfate 5H₂O were added thereto. The organic layer was recovered and the aqueous layer was extracted with ethyl acetate. The extracted solutions were combined, washed with brine, dried over anhydrous magnesium sulfate, and then filtered. The filtrate was evaporated and the resulting residue was purified by silica gel column chromatography, crystallized from ethanol, and the resulting crystals were collected filtration by adding hexane thereto to give 420 mg of 4-[(3-chloro-4-methoxybenzyl)amino]-1-(2-oxo-7-azaspiro[3.5]non-7-yl)-6-phthalazine carbonitrile.

¹H-NMR (400 MHz, DMSO-d₆) δ; 1.90 (4H, m), 2.86 (4H, m), 3.09 (4H, s), 3.80 (3H, s), 4.62 (2H, d, J=5.6 Hz), 7.07 (1H, d, J=8.5 Hz), 7.33 (1H, d, J=8.5 Hz), 7.44 (1H, s), 7.89 (1H, t, J=5.6 Hz), 8.09 (1H, d, J=8.0 Hz), 8.19 (1H, d, J=8.0 Hz), 8.88 (1H, s).

EXAMPLE 13

4-[(3-Chloro-4-methoxybenzyl)amino]-1-[4-hydroxy-4-(1H-1-imidazolylmethyl)piperidino]-6-phthalazinecarbonitrile Dihydrochloride

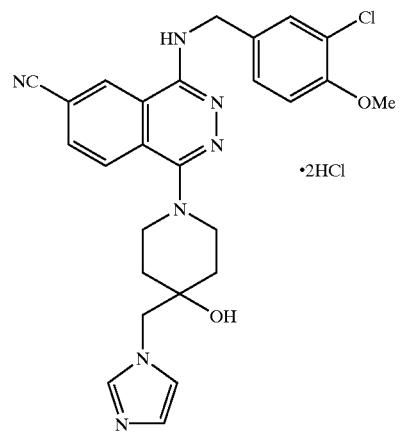

¹H-NMR (400 MHz, DMSO-d₆) δ; 1.49 (2H, d, J=12.4 Hz), 1.82–1.93 (2H, m), 3.13 (2H, t, J=10.8 Hz), 3.37 (2H, d, J=12.4 Hz), 3.82 (3H, s), 4.30 (2H, s), 4.74 (2H, d, J=5.6 Hz), 7.13 (1H, d, J=8.8 Hz), 7.48 (1H, dd, J=2.0, 8.4 Hz), 7.63 (1H, d, J=2.0 Hz), 7.66–7.71 (2H, m), 8.18 (1H, d, J=8.4 Hz), 8.48 (1H, d, J=8.4 Hz), 9.10 (1H, s), 9.60 (1H, s).

EXAMPLE 14

4-[(3-Chloro-4-methoxybenzyl)amino]-1-[4-hydroxy-4-(1H-1,2,4-triazol-1-ylmethyl)piperidino]-6-phthalazinecarbonitrile Dihydrochloride

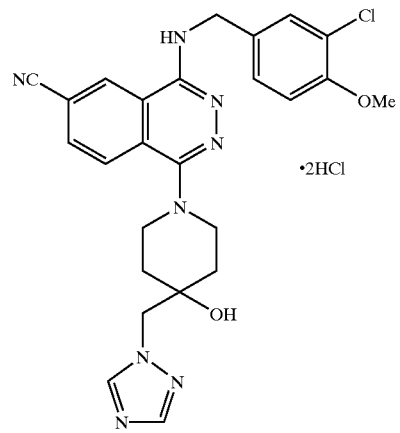

¹H-NMR (400 MHz, DMSO-d₆) δ; 1.54 (2H, d, J=12.8 Hz), 1.82–1.92 (2H, m), 3.15 (2H, t, J=11.2 Hz), 3.35 (2H, d, J=12.8 Hz), 3.82 (3H, s), 4.29 (2H, s), 4.73 (2H, d, J=6.0 Hz), 7.13 (1H, d, J=8.4 Hz), 7.48 (1H, dd, J=2.0, 8.4 Hz), 7.62 (1H, d, J=2.0 Hz), 8.20 (1H, d, J=8.4 Hz), 8.21 (1H, s), 8.45 (1H, dd, J=1.2, 8.4 Hz), 8.79 (1H, s), 9.56 (1H, s), 10.75 (1H, br-s).

EXAMPLE 15

1-[4-[(3-Chloro-4-methoxybenzyl)amino]-6-(1H-1,2,3,4-terolazol-5-yl)-1-phthalazinyl]-4-piperidinol

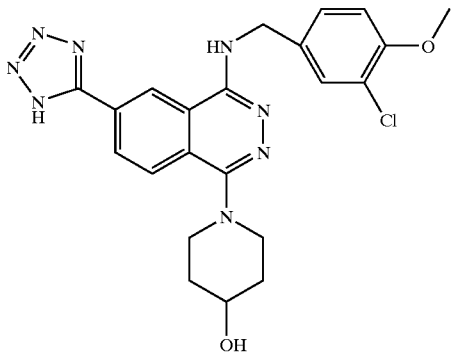

0.55 g sodium azide was added to a mixture of 1.0 g 4-[(3-Chloro-4-methoxybenzyl)amino]-1-(4-hydroxypiperidino)-6-phthalazine carbonitrile, 1.2 g triethylamine hydrochloride, and 20 ml 1-methyl-2-pyrrolidinone, and stirred at 100° C. for 8 hr. The reaction solution was returned to room temperature, water was added thereto, and the resulting crystals were collected by filtration to give 1.0 g of the title compound.

$^1$H-NMR (400 MHz, DMSO-d$_6$) δ; 1.58–1.7 (2H, m), 1.8–1.97 (2H, m), 2.8–2.98 (2H, m), 3.3–3.43 (2H, m), 3.6–3.7 (1H, m), 3.79 (3H, s), 4.6 (2H, s), 7.06 (1H, d, J=8 Hz), 7.34 (1H, d, J=8 Hz), 7.45 (1H, s), 7.95 (1H, d, J=8 Hz), 8.45 (1H, d, J=8 Hz), 8.89 (1H, s).

EXAMPLE 16

1-[4-[(3-Chloro-4-methoxybenzyl)amino]-6-(1-methyl-1H-1,2,3,4-tetrazol-5-yl)-1-phthalazinyl]-4-piperidinol

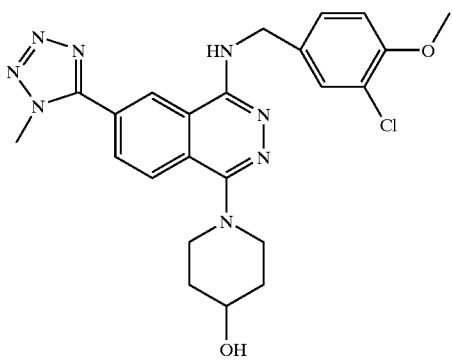

0.037 ml methyl iodide was added to a mixture of 0.25 g 1-[4-[(3-chloro-4-methoxybenzyl)amino]-6-(1H-1,2,3,4-tetrazole-5-yl)-1-phthalazinyl]-4-piperidinol, 1.2 g potassium carbonate and 5 ml dimethylformamide, and stirred at room temperature for 3 hr. Water was added to the reaction solution, and the precipitated insoluble matters were collected by filtration. Then, purified by silica gel column chromatography to give 50 mg of the title compound.

$^1$H-NMR (400 MHz, DMSO-d$_6$) δ; 1.6–1.7 (2H, m), 1.85–1.95 (2H, m), 2.85–2.95 (2H, m), 3.25–3.45 (2H, m), 3.6–3.7 (1H, m), 3.80 (3H, s), 4.48 (3H, s), 4.61 (2H, d, J=5.6 Hz), 4.73 (1H, d, J=4.0 Hz), 7.07 (1H, d, J=8.4 Hz), 7.34 (1H, dd, J=2.0, 8.4 Hz), 7.44 (1H, d, J=2.0 Hz), 8.07 (1H, t, J=5.6 Hz), 8.10 (1H, d, J=8.4 Hz), 8.47 (1H, d, J=8.8 Hz), 9.00 (1H, s).

EXAMPLE 17

4-[(3-Chloro-4-methoxybenzyl)amino]-1-(4-hydroxypiperidino)-6-phthalazine Carbothiamide

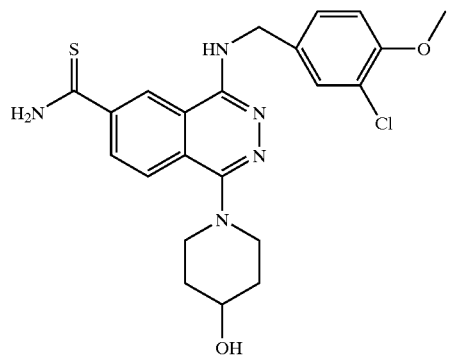

3.7 ml diethyl dithiophosphate was added to a mixture of 2.0 g 4-[(3-chloro-4-methoxybenzyl)amino]-1-(hydroxypiperidino)-6-phthalazine carbonitrile, 1 ml water and 2 ml isopropanol, and the mixture was heated under reflux for 1 hr. After cooling, water was added to the reaction solution and the resulting crystals were collected by filtration. The filtrate was extracted with ethyl acetate and washed with brine. It was dried over anhydrous sodium sulfate, and filtered. The filtrate was evaporated, and the resulting crystalline residue was combined with the crystals collected above by filtration, whereby 1.5 g of the title compound was obtained.

$^1$H-NMR (400 MHz, DMSO-d$_6$) δ; 1.6–1.7 (2H, m), 1.85–2.00 (2H, m), 2.90–3.1 (2H, m), 3.3–3.5 (2H, m), 3.6–3.8 (1H, m), 3.81 (3H, s), 4.68 (2H, d, J=4 Hz), 7.13 (1H, d, J=8 Hz), 7.40 (1H, d, J=8 Hz), 7.54 (1H, s), 8.08 (1H, d, J=8 Hz), 8.3–8.4 (1H, m), 8.9–9.1 (1H, m), 9.88 (1H, s), 10.33 (1H, s).

EXAMPLE 18

1-[4-[(3-Bromo-4-methoxybenzyl)amino]-6-(4-methyl-1,3-thiazol-2-yl)-1-phthalazinyl]4-piperidinol

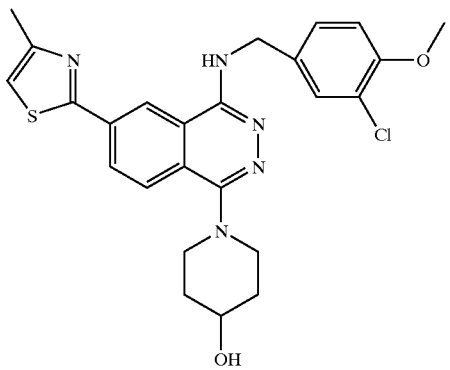

1.5 g of 4-[(3-chloro-4-methoxybenzyl)amino]-1-(4-hydroxypiperidino)-6-phthalazine carbodiamide was dissolved in 50 ml dimethylformamide, 1.1 ml chloroacetone was added thereto, and the mixture was stirred at 100° C. for 4 hr. After cooling, water was added to the reaction solution and the aqueous layer was removed by decantation. The residue was dried under reduced pressure, and then purified by silica gel chromatography to give 200 mg of the title compound.

$^1$H-NMR (400 MHz, DMSO-$d_6$) δ; 1.6–1.7 (2H, m), 1.85–1.95 (2H, m), 2.47 (3H, s), 2.83–2.94 (2H, m), 3.3–3.4 (2H, m), 3.6–3.7 (1H, m), 3.80 (3H, s), 4.63 (2H, d, J=5.6 Hz), 4.72 (1H, d, J=4.0 Hz), 7.07 (1H, d, J=8.4 Hz), 7.34 (1H, dd, J=2.0, 8.4 Hz), 7.44 (1H, d, J=2.0 Hz), 7.48 (1H, s), 7.96–8.04 (1H, m), 8.01 (1H, d, J=8.4 Hz), 8.36 (1H, dd, J=1.6, 8.4 Hz), 8.76 (1H, d, J=1.6 Hz).

EXAMPLE 19

1-[4-[(3-Chloro-4-methoxybenzyl)amino]-6-(2-thienyl)-1-phthalazinyl]-4-piperidinol Hydrochloride

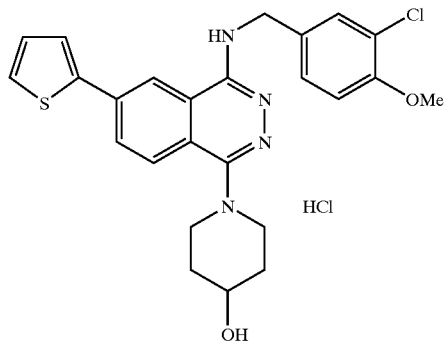

24 mg of tetrakis(triphenylphosphine)palladium (0) and 1.4 ml 2-(tributylstannyl)thiophene were added to a mixture of 200 mg 1-[6-bromo-4-[(3-bromo-4-methoxybenzyl)amino]-1-phthalazinyl]-4-piperidinol and 2 ml toluene. The mixture was heated under reflex for 2 hr. After cooling, the reaction solution was poured into ice water, and extracted with ethyl acetate. The extracted solution was dried over anhydrous magnesium sulfate, and then filtered. The filtrate was evaporated, and the residue was purified by silica gel chromatography. The resulting product was converted by 4 N hydrochloric acid/ethyl acetate into the hydrochloride to give 73 mg of the title compound.

$^1$H-NMR (400 MHz, DMSO-$d_6$) δ; 1.67 (2H, m), 1.92 (2H, m), 3.00 (2H, m) 3.45 (2H, m), 3.74 (1H, m), 3.82 (3H, s), 4.73 (2H, m), 7.13 (1H, d, J=7.2 Hz), 7.27 (1H, s), 7.46 (1H, d, J=7.2 Hz), 7.61 (1H, s), 7.79 (1H, d, J=5.6 Hz), 8.03 (1H, d, J=5.6 Hz), 8.09 (1H, d, J=8.8 Hz), 8.34 (1H, d, J=8.8 Hz), 9.20 (1H, br-s).

EXAMPLE 20

4-[(3-Chloro-4-methoxybenzyl)amino]-1-(4-hydroxypiperidino)-6-phthalazinecarbaldehyde Oxime Hydrochloride

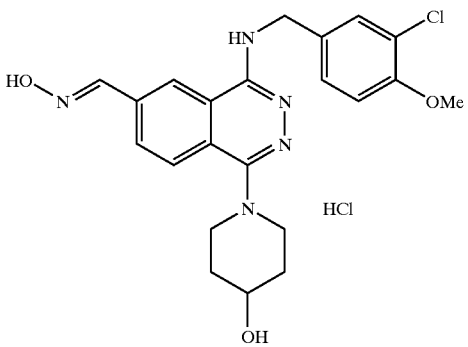

10.0 g of 4-[(3-chloro-4-methoxybenzyl)amino]-1-(4-hydroxypiperidino)-6-phthalazine carbonitrile and 5.3 g of t-butyldimethylchlorosilane were dissolved in 80 ml dimethylformamide, and 4.8 g of imidazole was added thereto. The mixture was stirred at room temperature overnight. Ethyl acetate was added to the reaction solution which was then washed once with water and twice with brine. The mixture was was dried over anhydrous magnesium sulfate and filtrated. The filtrate was evaporated to give 11.7 g of 1-[4-[[1-(tert-butyl)-1,1-dimethylsilyl]oxy]piperidino]-4-[(3-chloro-4-methoxybenzyl)amino]-6-phthalazine carbonitrile.

11.7 g of 1-[4-[[1-(tert-butyl)-1,1-dimethylsilyl]oxy] piperidino]-4-[(3-chloro-4-methoxybenzyl)amino]-6-phthalazine carbonitrile was dissolved in 150 ml methylene chloride and cooled. 44 ml solution of 1 M hydrogenated diisobutylaluminum in toluene was added thereto at −78° C. After returned to room temperature, the mixture was stirred overnight. 100 ml saturated aqueous ammonium chloride was added thereto, and the mixture was stirred at room temperature for 0.5 hr. After 40 ml of 10% sulfuric acid was added thereto, it was extracted with ethyl acetate. The extracted solution was washed with brine, dried over anhydrous magnesium sulfate, and then filtered. The filtrate was evaporated, and the residue was purified by silica gel column chromatography to give 5.3 g of 1-[4-[[(1-(tert-butyl)-1,1-dimethylsilyl]oxy]piperidino]-4-[(3-chloro-4-methoxybenzyl)amino]-6-phthalazine carbaldehyde.

1.5 g of 1-[4-[[(1-(tert-butyl)-1,1-dimethylsilyl]oxy] piperidino]-4-[(3-chloro-4-methoxybenzyl)amino]-6- phthalazine carbaldehyde and 0.35 g of hydroxylamine hydrochloride were dissolved in 50 ml methanol, and the mixture was heated under reflux for 2 hr. After cooling, water was added thereto which was then extracted with ethyl acetate. The extracted solution was washed with brine, dried over anhydrous magnesium sulfate, and then filtered. The filtrate was evaporated, and the residue was purified by silica gel column chromatography to give 1.18 g of 1-[4-[[(1-(tert-butyl)-1,1-dimethylsilyl]oxy]piperidino]-4-[(3-chloro-4-methoxybenzyl)amino]-6-phthalazine carbaldehyde oxime.

A 1 M solution of tetrabutylammonium fluoride in tetrahydrofuran was added to 30 ml solution of 1.18 g 1-[4-[[(1-(tert-butyl)-1,1-dimethylsilyl]oxy]piperidino]-4-[(3-chloro-4-methoxybenzyl)amino]-6-phthalazine carbaldehye oxime in tetrahydrofuran. The mixture was stirred at room temperature overnight. Water was added to the reaction solution which was then extracted with ethyl acetate. The extracted solution was washed with brine, dried over anhydrous magnesium sulfate, and then filtered. The filtrate was evaporated, and the resulting crystalline residue was washed with ethyl acetate and collected by filtration to give 0.34 g of the title compound. This product was converted in a usual manner into the hydrochloride.

$^1$H-NMR (400 MHz, DMSO-$d_6$) δ; 1.58–1.70 (2H, m), 1.86–1.95 (2H, m), 2.92–3.02 (2H, m), 3.08–3.22 (2H, m), 3.64–3.73 (1H, m), 3.82 (3H, s), 4.61–4.68 (2H, m), 4.77–4.79 (1H, m), 7.10 (1H, d, J=8 Hz), 7.38 (1H, d, J=8 Hz), 7.51 (1H, s), 8.06 (1H, d, J=8 Hz), 8.23 (1H, d, J=8 Hz), 8.28 (1H, s), 8.69–8.76 (1H, m).

EXAMPLE 21

4-[(3-Chloro-4-methoxybenzyl)amino]-1-[(2R)-2-(hydroxymethyl)-1-oxa-8-azaspiro[4.5]deca-8-yl]-6-phthalazinecarbonitrile Hydrochloride

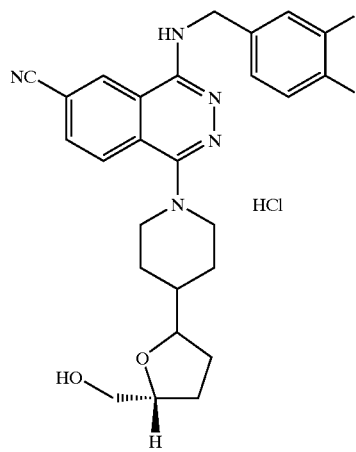

1.08 g of 1-chloro-4-[(3-chloro-4-methoxybenzyl)amino]-6-phthalazine carbonitrile and 0.76 g of (2R)-1-oxa-8-azaspiro[4.5]deca-2-yl methanol were dissolved in 20 ml N-methyl-2-pyrrolidone and stirred at 160° C. for 5 hr. After the completion of the reaction, the reaction solution was returned to room temperature, water and saturated aqueous sodium bicarbonate were added thereto, extracted with ethyl acetate, and washed with brine for three times. After it was dried over magnesium sulfate, the solvent was removed, and the residue was purified by silica gel column chromatography to give 0.60 g crystalline compound.

The resulting compound was dissolved in 20 ml ethanol, 1.40 ml of 1 N hydrochloric acid/ethanol was added thereto at room temperature, and the mixture was stirred for 10 min. After the solvent was removed, the residue was treated with diisopropyl ether, and then dried to give 555 mg of the title compound.

$^1$H-NMR (400 MHz, DMSO-$d_6$) δ; 1.67–1.98 (8H, m), 3.15–3.40 (6H, m), 3.82 (3H, s), 3.90–3.98 (1H, m), 4.68–4.77 (2H, m), 7.14 (1H, d, J=9 Hz), 7.46 (1H, dd, J=2,9 Hz), 7.62 (1H, d, J=2 Hz), 8.23 (1H, d, J=9 Hz), 8.45 (1H, d, J=9 Hz), 9.50 (1H, s).

EXAMPLE 22

(anti)-4-[(3-Chloro-4-methoxybenzyl)amino]-1-(7-hydroxy-3-oxa-9-azabicyclo[3.3.1]non-9-yl)-6-phthalazinecarbonitrile Hydrochloride

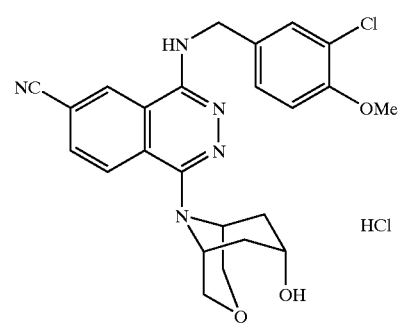

1.5 g of 1-chloro-4-[(3-chloro-4-methoxybenzyl)amino]-6-phthalazine carbonitrile, 1.13 g of (anti)-3-oxa-9-azabicyclo[3.3.1]nonan-7-ol hydrochloride and 2.16 ml diisopropylethylamine were added to 8 ml N-methyl-2-pyrrolidone, and the mixture was stirred at 170° C. for 9 hr and 15 min. Water was added to the reaction solution which was then extracted with ethyl acetate, and the organic layer was washed with water and brine. After the mixture was dried over anhydrous magnesium sulfate, the solvent was evaporated. The residue was purified by silica gel column chromatography (solvent; dichloromethane/methanol) to give 0.085 g of an yellow oil.

The resulting oil was dissolved in ethyl acetate, then 0.05 ml of 4 N hydrogen chloride/ethyl acetate was added thereto, and the mixture was stirred at room temperature. The resulting precipitates were collected by filtration to give 0.075 g of the title compound.

¹H-NMR (400 MHz, DMSO-d₆) δ; 1.69–1.78 (2H, m), 2.46–2.56 (2H, m), 3.77–3.84 (2H, m), 3.86 (3H, s), 3.86–3.95 (3H, m), 4.04–4.12 (2H, m), 4.74 (2H, s), 7.17 (1H, d, J=8.4 Hz), 7.46 (1H, dd, J=2.2, 8.4 Hz), 7.61 (1H, d, J=2.2 Hz), 8.13 (1H, d, J=8.4 Hz), 8.45 (1H, d, J=8.4 Hz), 9.39 (1H, m).

EXAMPLE 23

(anti)-4-[(3-Chloro-4-methoxybenzyl)amino]-1-(9-hydroxy-3-azabicyclo[3.3.1]non-3-yl)-6-phthalazinecarbonitrile Hydrochloride

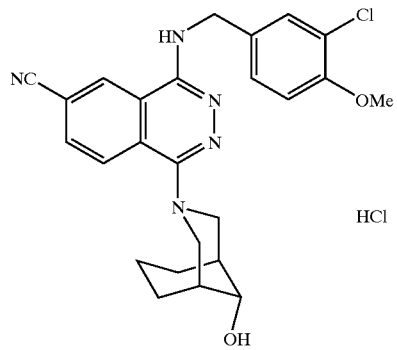

1.5 g of 12-chloro-4-[(3-chloro-4-methoxybenzyl)amino]-6-phthalazine carbonitrile, 1.12 g of (anti)-3-azabicyclo[3.3.1]nonan-9-ol hydrochloride and 2.18 ml diisopropylethylamine were added to 8 ml N-methyl-2-pyrrolidone, and the mixture was stirred at 170° C. for 9 hr. Water was added to the reaction solution which was then extracted with ethyl acetate, and the organic layer was washed with water and brine. It was dried over anhydrous magnesium sulfate, and then the solvent was evaporated. Dichloromethane was added thereto and the insoluble matters were collected by filtration to give 1.23 g pale yellow powder. The resulting powder was suspended in ethyl acetate, 0.7 ml of 4 N hydrogen chloride/ethyl acetate was added thereto, and the mixture was stirred at room temperature. The resulting precipitates were collected by filtration to give 1.28 g of the title compound as a light-colored powder.

¹H-NMR (400 MHz, DMSO-d₆) δ; 1.54 (1H, m), 1.66–1.75 (2H, m), 1.86–1.93 (2H, m), 2.11–2.23 (2H, m), 2.38 (1H, m), 3.15–3.24 (2H, m), 3.62–3.70 (2H, m), 3.75 (1H, m), 3.85 (3H, s), 4.74 (2H, s), 7.16 (1H, d, J=8.4 Hz), 7.47 (1H, dd, J=1.8, 8.4 Hz), 7.62 (1H, d, J=1.8 Hz), 8.23 (1H, d, J=8.4 Hz), 8.56 (1H, dd, J=1.3, 8.4 Hz), 9.49 (1H, m).

EXAMPLE 24

(anti)-4-[(3-Chloro-4-methoxybenzyl)amino]-1-[9-(2-hydroxyethyl)-3-azabicyclo[3.3.1]non-3-yl]-6-phthalazinecarbonitrile Hydrochloride

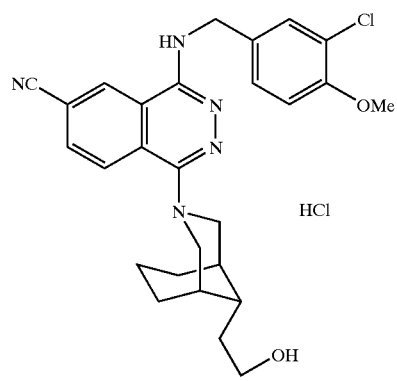

1.5 g of 1-chloro-4-[(3-chloro-4-methoxybenzyl)amino]-6-phthalazine carbonitrile, 1.29 g of (anti)-2-(3-azabicyclo[3.3.1]non-9-yl)-1-ethanol hydrochloride and 2.18 ml diisopropylethylamine were added to 8 ml N-methyl-2-pyrrolidone, and the mixture was stirred at 170° C. for 8 hr and 40 min. Water was added to the reaction solution which was then extracted with ethyl acetate, and the organic layer was washed with water and brine. The reaction solution was dried over anhydrous magnesium sulfate, and then the solvent was evaporated. The residue was purified by silica gel column chromatography (solvent; dichloromethane/methanol) and crystallized from dichloromethane-ethyl acetate-ether to give 1.12 g pale yellow powder. The resulting powder was suspended in acetone, 2 ml of 4 N hydrogen chloride/ethyl acetate and ethyl acetate were added thereto, and the mixture was stirred at room temperature. The resulting precipitates were collected by filtration to give 0.98 g of the title compound as a pale yellow powder.

¹H-NMR (400 MHz, DMSO-d₆) δ; 1.61 (1H, m), 1.66–1.73 (2H, m), 1.73–1.87 (5H, m), 1.88–2.00 (2H, m), 2.42 (1H, m), 3.14–3.23 (2H, m), 3.49 (2H, t, J=6.4 Hz), 3.67–3.76 (2H, m), 3.85 (3H, s), 4.73 (2H, s), 7.16 (1H, d, J=8.6 Hz), 7.47 (1H, dd, J=1.6, 8.6 Hz), 7.62 (1H, d, J=1.6 Hz), 8.24 (1H, d, J=8.4 Hz), 8.55 (1H, dd, J=1.3, 8.4 Hz), 9.46 (1H, m).

EXAMPLE 25

1-(3-Amino-3-methyl-1-butynyl)-4-[(3-chloro-4-methoxybenzyl)amino]-6-phthalazinecarbonitrile Hydrochloride

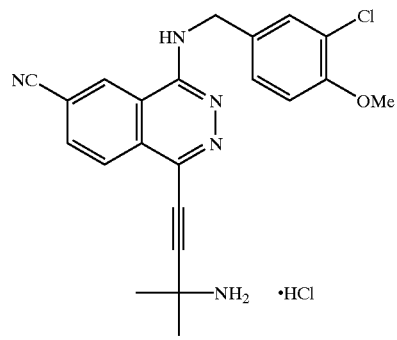

0.39 ml triethylamine was added to a mixture of 500 mg 1-chloro-4-[(3-chloro-4-methoxybenzyl)amino]-6- phthalazine carbonitrile, 53 mg cuprous iodide, 98 mg dichlorobis(triphenylphosphine)palladium (II), 347 mg 3-amino-3-methyl-1-butyne, and 10 ml dimethylformamide, and the mixture was stirred at 80° C. for 3 hr in a nitrogen atmosphere. After cooling, ethyl acetate was added to the reaction solution, then water and conc. aqueous ammonia were added thereto, and the organic layer was recovered. The organic layer was washed with dilute aqueous ammonia and brine, and dried over anhydrous sodium sulfate. It was filtered and the filtrate was evaporated. The resulting residue was purified by NH-form silica gel column chromatography to give 446 mg of the title compound. The product was converted in a usual manner into the hydrochloride.

$^1$H-NMR (400 MHz, DMSO-d$_6$) δ; 1.75 (6H, s), 3.82 (3H, s), 4.76 (2H, d, J=5.6 Hz), 7.10 (1H, d, J=8.4 Hz), 7.37 (1H, dd, J=8.4, 2.2 Hz), 7.50 (1H, d, J=2.2 Hz), 8.31 (1H, dd, J=8.4, 1.4 Hz), 8.35 (1H, d, J=8.4 Hz), 8.83 (1H, t, J=5.6 Hz), 8.92–9.05 (3H, m), 9.07 (1H, br).

EXAMPLE 26

4-[(3-Chloro-4-methoxybenzyl)amino]-1-[4-(methoxyimino)piperidino]-6-phthalazinecarbonitrile Hydrochloride

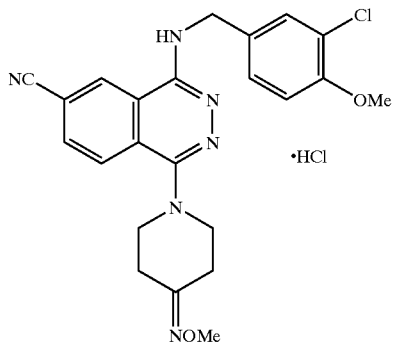

A mixture of 1.19 g 4-[(3-chloro-4-methoxybenzyl)amino]-1-[4-oxopiperidino]-6-phthalazine carbonitrile, 354 mg methoxyamine hydrochloride, 1.2 g sodium carbonate, and 10 ml ethanol was heated under reflux for 2 hr. After cooling, saline was added to the reaction solution which was then extracted with ethyl acetate. It was dried over anhydrous sodium sulfate, and filtered. The filtrate was evaporated, and the resulting residue was purified by silica gel column chromatography to give 620 mg of 4-[(3-chloro-4-methoxybenzyl)amino]-1-[4-(methoxyimino)piperidino]-6-phthalazine carbonitrile. This product was dissolved in a mixed solvent of methanol and ethanol, and recrystallized by adding 0.35 ml of 4 N hydrochloric acid/ethyl acetate to give 388 mg of 4-[(3-chloro-4-methoxybenzyl)amino]-1-[4-(methoxyimino)piperidino]-6-phthalazinecarbonitrile hydrochloride.

$^1$H-NMR (400 MHz, DMSO-d$_6$) δ; 2.50–2.55 (2H, m), 2.74–2.80 (2H, m), 3.29–3.35 (4H, m), 3.77 (3H, s), 3.85 (3H, s), 4.72 (2H, br), 7.16 (1H, d, J=8.4 Hz), 7.45 (1H, dd, J=8.4, 2.0 Hz), 7.60 (1H, d, J=2.0 Hz), 8.33 (1H, d, J=8.8 Hz), 8.48 (1H, dd, J=8.8, 0.8 Hz), 9.35 (1H, d, J=0.8 Hz), 10.19 (1H, br).

The following compounds were synthesized using their corresponding starting materials in the same manner as in Production Examples or Examples.

EXAMPLE 27

4-[(3-Chloro-4-methylbenzyl)amino]-1-(4-hydroxypiperidino)-6-phthalazinecarbonitrile Hydrochloride

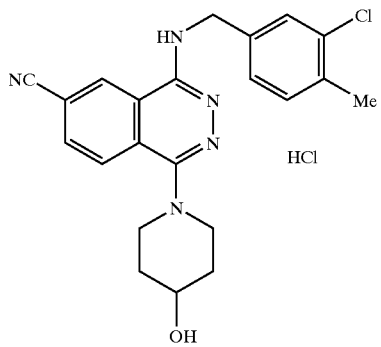

$^1$H-NMR (400 MHz, DMSO-d$_6$) δ; 1.62–1.73 (2H, m), 1.90–1.99 (2H, m), 2.32 (3H, s), 2.98–3.08 (2H, m), 3.42–3.50 (2H, m), 3.72–3.80 (1H, m), 4.76 (2H, d, J=5.6 Hz), 7.36 (2H, s), 7.57 (1H, s), 8.23 (1H, d, J=8.4 Hz), 8.47 (1H, dd, J=8.4, 1.2 Hz), 9.37 (1H, d, J=1.2 Hz), 10.21 (1H, br).

EXAMPLE 28

4-[(3-Chloro-4-methoxybenzyl)amino]-1-(5-hydroxyperhydrocyclopenta[c]pyrrol-2-yl)-6-phthalazine Carbonitrile

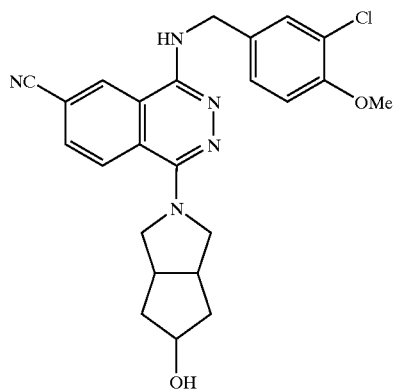

$^1$H-NMR (400 MHz, DMSO-d$_6$) δ; 1.40–1.49 (2H, m), 2.02–2.12 (2H, m), 2.55–2.64 (2H, m), 3.24 (4H, d, J=4.0 Hz), 3.80 (3H, s), 3.94–4.04 (1H, m), 4.61 (2H, d, J=5.2 Hz), 4.72 (1H, d, J=5.6 Hz), 7.07 (1H, d, J=8.4 Hz), 7.32 (1H, dd, J=2.0, 8.4 Hz), 7.77–7.83 (1H, m), 8.14–8.23 (2H, m), 8.66 (1H, d, J=0.8 Hz).

EXAMPLE 29

4-[(3-Chloro-4-methoxybenzyl)amino]-1-[4-(2-hydroxyethyl)-1,2,3,6-tetrahydro-1-pyridinyl]-6-phthalazine Carbonitrile

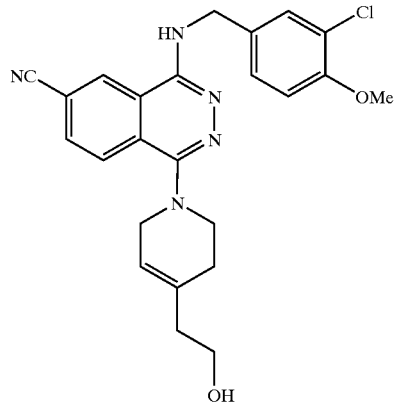

$^1$H-NMR (400 NHz, DMSO-$d_6$) δ; 2.15–2.22 (2H, m), 2.27–2.39 (2H, m), 3.20 (2H, t, J=5.6 Hz), 3.48–3.60 (2H, m), 3.69 (2H, s), 3.80 (3H, s), 4.47 (1H, t, J=5.6 Hz), 4.61 (2H, d, J=5.6 Hz), 5.55 (1H, d, J=0.4 Hz), 7.08 (1H, d, J=8.4 Hz), 7.33 (1H, dd, J=2.0, 8.4 Hz), 7.44 (1H, d, J=2.0 Hz), 7.83–7.89 (1H, m), 8.04 (1H, d, J=8.4 Hz), 8.08 (1H, dd, J=1.2, 8.4 Hz), 8.87 (1H, t, J=0.4 Hz).

EXAMPLE 30

4-[(3-Chloro-4-methoxybenzyl)amino]-1-[3-(hydroxymethyl)tetrahydro-1H-1-pyrrolyl]-6-phthalazine Carbonitrile

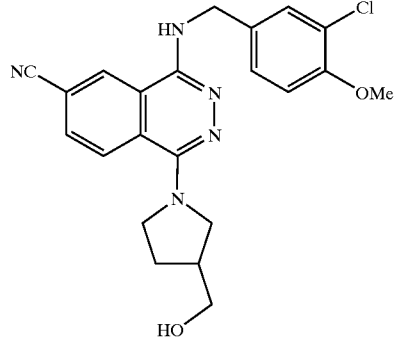

$^1$H-NMR (400 MHz, DMSO-$d_6$) δ; 1.59–1.70 (1H, m), 1.83–2.02 (2H, m), 2.31–2.41 (1H, m), 3.34–3.60 (5H, m), 4.58 (2H, J=5.6 Hz), 4.67 (1H, t, J=5.6 Hz), 7.07 (1H, d, J=8.4 Hz), 7.32 (1H, dd, J=2.0, 8.4 Hz), 7.43 (1H, d, J=2.0 Hz), 7.56–7.62 (1H, m), 8.14 (1H, dd, J=1.6, 8.8 Hz), 8.23 (1H, d, J=8.8 Hz), 8.820 (1H, d, J=1.2 Hz).

EXAMPLE 31

4-[(3-Chloro-4-methoxybenzyl)amino]-1-[4-(hydroxymethyl)-1,2,3,6-tetrahydro-1-pyridinyl]-6-phthalazine Carbonitrile

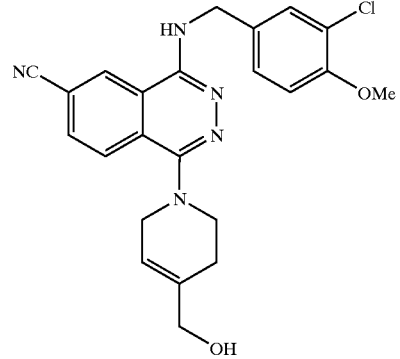

$^1$H-NMR (400 MHz, DMSO-$d_6$) δ; 2.28 (2H, br-s), 3.19–3.26 (2H, m), 3.73 (2H, br-s), 3.80 (3H, s), 3.89 (2H, d, J=4.4 Hz), 4.62 (2H, d, J=5.6 Hz), 4.78 (1H, t, J=5.6 Hz), 5.72 (1H, br-s), 7.08 (1H, d, J=8.4 Hz), 7.33 (1H, dd, J=2.0, 8.4 Hz), 7.44 (1H, d, J=2.0 Hz), 7.87 (1H, t, J=5.6 Hz), 8.05 (1H, d, J=8.4 Hz), 8.18 (1H, dd, J=1.2, 8.4 Hz), 8.87 (1H, d, J=1.2 Hz).

EXAMPLE 32

2-[1-[4-[(3-Chloro-4-methoxybenzyl)amino]-6-cyano-1-phthalazinyl]-4-piperidinyl]propionic Acid Hydrochloride

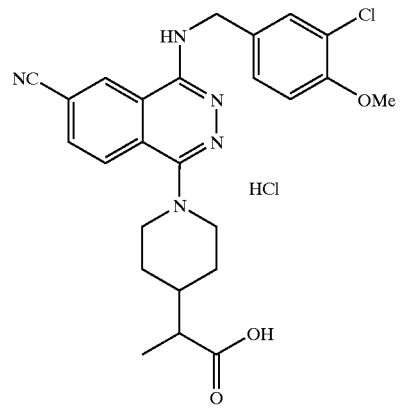

$^1$H-NMR (400 MHz, DMSO-$d_6$) δ; 1.08 (3H, d, J=6.8 Hz), 1.46–1.64 (2H, m), 1.66–1.83 (3H, m), 2.22–2.32 (1H, m), 2.78–2.90 (2H, m), 3.54–3.64 (2H, m), 3.83 (3H, s), 4.72 (2H, d, J=6.0 Hz), 7.14 (1H, d, J=8.4 Hz), 7.46 (1H, dd, J=2.0, 8.4 Hz), 7.61 (1H, d, J=2.0 Hz), 8.22 (1H, d, J=8.4 Hz), 8.45 (1H, dd, J=1.6, 8.4 Hz), 9.49 (1H, s).

EXAMPLE 33

2-[1-[4-[(3-Chloro-4-methoxybenzyl)amino]-6-cyano-1-phthalazinyl]-1,2,3,6-tetrahydro-4-pyridinyl]acetic Acid Hydrochloride

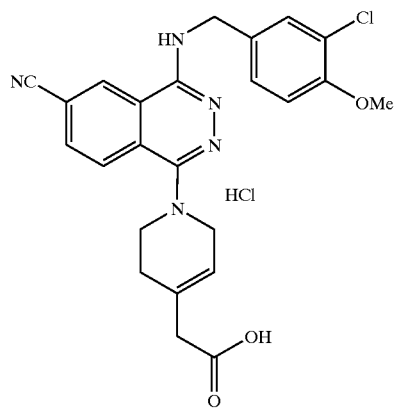

$^1$H-NMR (400 MHz, DMSO-d$_6$) δ; 2.38–2.44 (2H, m), 3.04 (2H, s), 3.79–3.83 (2H, m), 3.83 (3H, s), 4.72 (2H, t, J=2.8 Hz), 5.63–5.68 (1H, m), 7.15 (1H, d, J=8.8 Hz), 7.46 (1H, dd, J=2.4, 8.4 Hz), 7.61 (1H, d, J=2.4 Hz), 8.21 (1H, d, J=8.8 Hz), 8.46 (1H, dd, J=1.2, 8.4 Hz), 9.45 (1H, s).

EXAMPLE 34

2-[1-[4-[(3-Chloro-4-methoxybenzyl)amino]-6-cyano-1-phthalazinyl]-4-piperidinyl]-2-fluoroacetic Acid Hydrochloride

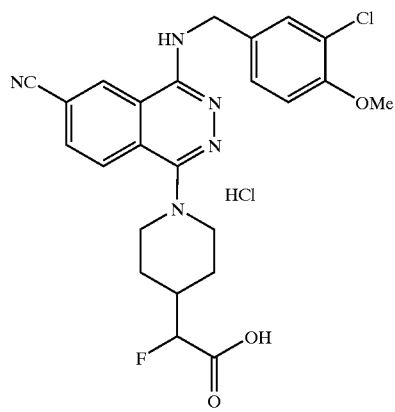

$^1$H-NMR (400 MHz, DMSO-d$_6$) δ; 1.60–1.90 (4H, m), 2.03–2.20 (1H, m), 2.83–2.98 (2H, m), 3.58–3.65 (2H, m), 3.83 (3H, s), 4.73 (2H, t, J=2.8 Hz), 4.98 (1H, dd, J=4.0, 48.4 Hz), 7.14 (1H, d, J=8.4 Hz), 7.46 (1H, dd, J=2.0, 8.4 Hz), 7.61 (1H, d, J=2.4 Hz), 8.23 (1H, d, J=8.4 Hz), 8.44 (1H, dd, J=1.2, 8.4 Hz), 8.46 (1H, s).

EXAMPLE 35

2-[1-[4-[(3-Chloro-4-methoxybenzyl)amino]-6-cyano-1-phthalazinyl]-4-piperizyl] acetic Acid Hydrochloride

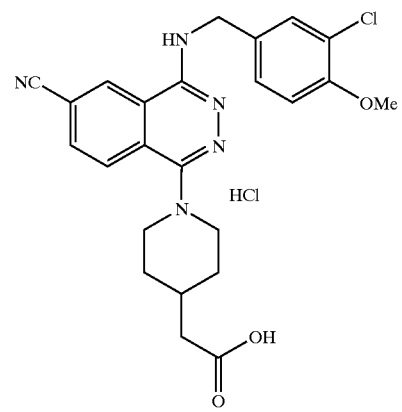

$^1$H-NMR (400 MHz, DMSO-d$_6$) δ; 1.44–1.57 (2H, m), 1.79–1.84 (2H, m), 1.85–1.96 (1H, m), 2.25 (2H, d, J=6.8 Hz), 2.89 (2H, t, J=12.0 Hz), 3.55 (2H, d, J=12.0 Hz), 3.84 (3H, s), 4.70 (2H, d, J=6.0 Hz), 7.15 (1H, d, J=8.8 Hz), 7.44 (1H, dd, J=2.0, 8.4 Hz), 7.94 (1H, d, J=2.0 Hz), 8.21 (1H, d, J=8.4 Hz), 8.46 (1H, dd, J=1.6, 8.8 Hz), 9.37 (1H, s).

EXAMPLE 36

4-[(3-Chloro-4-methoxybenzyl)amino]-1-(4-[1-fluoro-2-hydroxyethyl)piperidino]-6-phthalazinecarbonitrile Hydrochloride

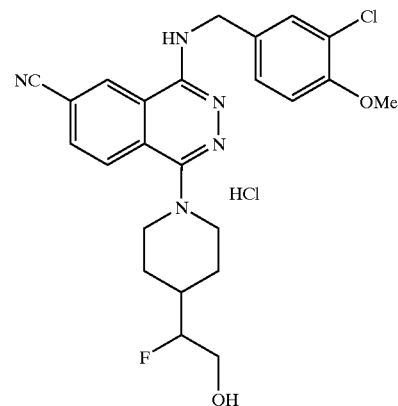

$^1$H-NMR (400 MHz, DMSO-d$_6$) δ; 1.56–1.78 (3H, m), 1.83–1.99 (2H, m), 2.80–2.91 (2H, m), 3.51–3.69 (4H, m), 3.83 (3H, s), 4.25–4.31 (1/2H, m), 4.37–4.43 (1/2H, m), 4.73 (2H, d, J=5.6 Hz), 7.14 (1H, d, J=8.4 Hz), 7.47 (1H, dd, J=2.0, 8.4 Hz), 7.62 (1H, d, J=2.0 Hz), 8.22 (1H, d, J=8.4 Hz), 8.45 (1H, dd, J=1.2, 8.4 Hz), 9.52 (1H, s), 10.58 (1H, s).

EXAMPLE 37

4-[(3-Chloro-4-methoxybenzyl)amino]-1-[4-(2-hydroxyethoxy)piperidino]-6-phthalazinecarbonitrile Hydrochloride

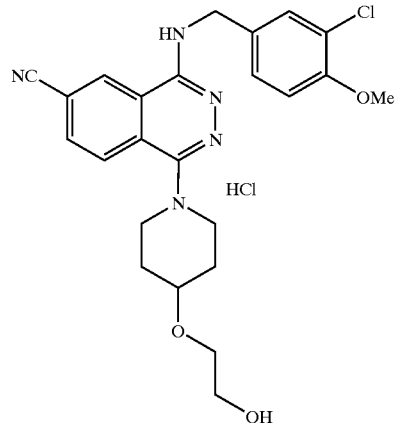

¹H-NMR (400 MHz, DMSO-d₆) δ; 1.68–1.77 (4H, m), 1.98–2.07 (2H, m), 2.98–3.07 (2H, m), 3.44–3.52 (2H, m), 3.56–3.62 (3H, m), 3.83 (3H, s), 4.74 (2H, d, J=5.6 Hz), 7.13 (1H, d, J=8.4 Hz), 7.48 (1H, dd, J=2.0, 8.4 Hz), 7.627 (1H, d, J=2.0 Hz), 8.23 (1H, d, J=8.4 Hz), 8.45 (1H, dd, J=1.6, 8.4 Hz), 9.57 (1H, s), 10.68 (1H, br-s).

EXAMPLE 38

2-[[1-[4-[(3-Chloro-4-methoxybenzyl)amino]-6-cyano-1-phthalazinyl]-4-piperizyl]oxy]acetic Acid Hydrochloride

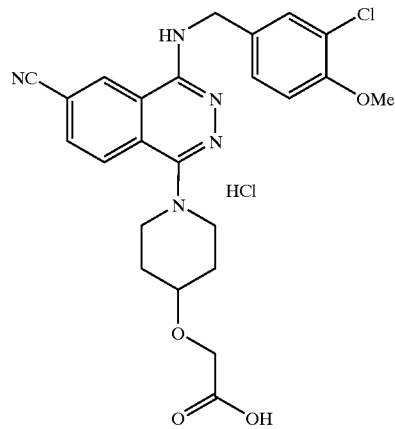

¹H-NMR (400 MHz, DMSO-d₆) δ; 1.69–1.82 (2H, m), 1.99–2.10 (2H, m), 2.98–3.09 (2H, m), 3.60–3.68 (1H, m), 3.83 (3H, s), 4.08 (2H, s), 4.72 (2H, d, J=5.6 Hz), 7.14 (1H, d, J=8.4 Hz), 7.46 (1H, dd, J=2.4, 8.4 Hz), 7.61 (1H, d, J=2.0 Hz), 8.24 (1H, d, J=8.4 Hz), 8.46 (1H, dd, J=1.2, 8.4 Hz), 9.46 (1H, s), 10.46 (1H, br-s).

EXAMPLE 39

4-[(3-Chloro-4-methoxybenzyl)amino]-1-[4-(2-hydroxy-1-methylethyl)piperidino]-6-phthalazine Carbonitrile

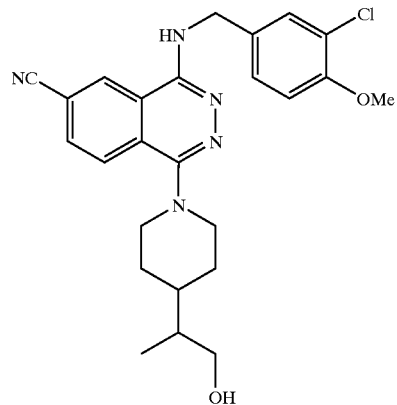

¹H-NMR (400 MHz, DMSO-d₆) δ; 0.85 (3H, d, J=6.4 Hz), 1.40–1.59 (4H, m) 1.64–1.73 (2H, m), 2.68–2.79 (2H, m), 3.33–3.47 (4H, m), 3.78 (3H, m), 4.40 (1H, t, J=5.2 Hz), 4.60 (2H, d, J=5.6 Hz), 7.06 (1H, d, J=8.4 Hz), 7.31 (1H, dd, J=2.0, 8.4 Hz), 7.42 (1H, d, J=2.0 Hz), 7.85 (1H, t, J=6.0 Hz), 8.03 (1H, d, J=8.4 Hz), 8.16 (1H, dd, J=1.6, 8.4 Hz), 8.85 (1H, d, J=0.8 Hz).

EXAMPLE 40

2-[7-[4-[(3-Chloro-4-methoxybenzyl)amino]-6-cyano-1-phthalazinyl]-7-azaspiro[3.5]non-2-yl] acetic Acid Hydrochloride

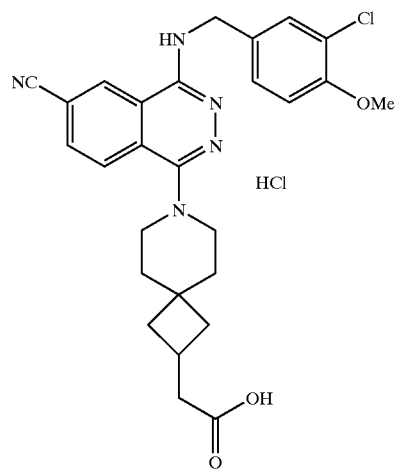

¹H-NMR (400 MHz, DMSO-d₆) δ; 1.45–1.53 (2H, m), 1.66–1.73 (2H, m), 1.77–1.84 (2H, m), 1.96–2.04 (2H, m), 2.34 (2H, d, J=7.6 Hz), 3.02 (2H, br-s), 3.11 (2H, br-s), 3.82 (3H, s), 4.67 (2H, s), 7.11 (1H, d, J=8.4 Hz), 7.40 (1H, dd, J=2.0, 8.4 Hz), 7.54 (1H, d, J=2.0 Hz), 8.15 (1H, d, J=8.8 Hz), 8.34 (1H, d, J=8.8 Hz), 9.24 (1H, s).

EXAMPLE 41

4-[(3-Chloro-4-methoxybenzyl)amino]-1-[2-(hydroxymethyl)perhydro[1.3]dioxolo[4.5-c]pyrrol-5-yl]-6-phthalazinecarbonitrile Hydrochloride

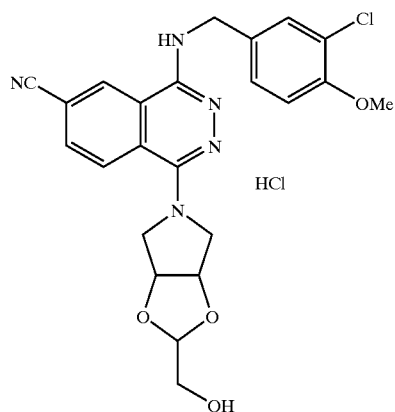

$^1$H-NMR (400 MHz, DMSO-$d_6$) δ; 3.54–3.67 (2H, m), 3.80–3.92 (2H, m), 4.16 (2/3H, br-s), 4.29 (4/3H, br-s), 4.54 (1H, t, J=5.2 Hz), 4.54–4.62 (1H, m), 5.16–5.32 (2H, m), 7.11 (1H, d, J=8.4 Hz), 7.34–7.40 (1H, m), 7.50 (1H, s), 8.37 (1H, d, J=8.4 Hz), 8.48–8.58 (1H, m), 9.12–9.21 (1H, m).

EXAMPLE 42

4-[(3-Chloro-4-methoxybenzyl)amino]-1-[4-(1-hydroxyethyl)piperidino-6-phthalazinecarbonitrile Hydrochloride

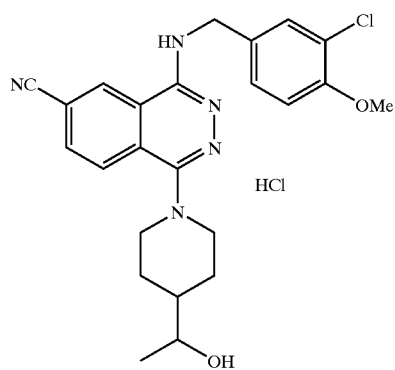

$^1$H-NMR (400 MHz, DMSO-$d_6$) δ; 1.07 (3H, d, J=6.0 Hz), 1.34–1.60 (3H, m), 1.65–1.76 (2H, m), 1.86–1.94 (2H, m), 2.75–2.86 (2H, m), 3.55–3.63 (2H, m), 3.82 (3H, s), 4.73 (2H, d, J=5.6 Hz), 7.13 (1H, d, J=8.8 Hz), 7.48 (1H, dd, J=2.0, 8.8 Hz), 7.63 (1H, d, J=2.0 Hz), 8.20 (1H, d, J=8.4 Hz), 8.45 (1H, dd, J=1.2, 8.4 Hz), 9.56 (1H, s), 10.69 (1H, br-s).

EXAMPLE 43

4-[(3-Chloro-4-methoxybenzyl)amino]-1-[4-fluoro-4-(hydroxymethyl)piperidino]-6-phthalazinecarbonitrile Hydrochloride

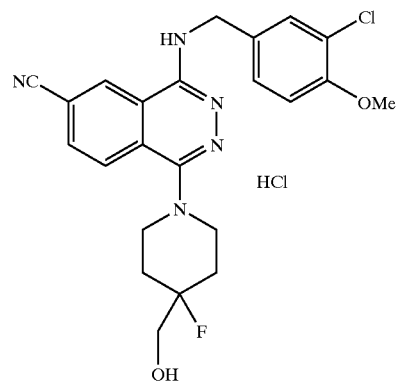

$^1$H-NMR (400 MHz, DMSO-$d_6$) δ; 1.69–1.77 (2H, m), 1.83–2.08 (2H, m), 3.05–3.16 (2H, m), 3.48 (2H, d, J=20.0 Hz), 3.82 (3H, s), 4.74 (2H, d, J=5.6 Hz), 7.14 (1H, d, J=8.8 Hz), 7.48 (1H, dd, J=2.0, 8.8 Hz), 7.63 (1H, d, J=2.0 Hz), 8.26 (1H, d, J=8.4 Hz), 8.46 (1H, dd, J=1.2, 8.4 Hz), 9.57 (1H, s), 10.73 (1H, br-s).

EXAMPLE 44

4-[(3-Chloro-4-methoxybenzyl)amino]-1-[4-(hydroxymethyl)-4-methoxypiperidino]-6-phthalazinecarbonitrile Hydrochloride

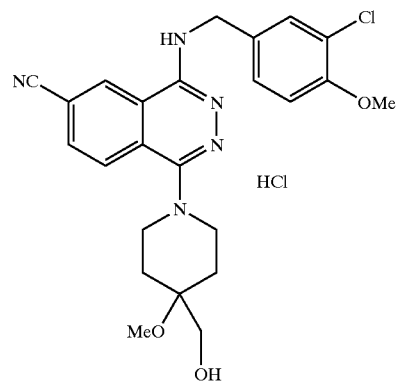

$^1$H-NMR (400 MHz, DMSO-$d_6$) δ; 1.71–1.86 (4H, m), 3.04–3.16 (2H, m), 3.16 (3H, s), 3.41 (2H, s), 3.83 (3H, s), 4.72 (2H, d, J=5.6 Hz), 7.14 (1H, d, J=8.4 Hz), 7.46 (1H, dd, J=2.0, 8.4 Hz), 7.61 (1H, d, J=2.0 Hz), 8.23 (1H, d, J=8.8 Hz), 8.44 (1H, dd, J=1.2, 8.8 Hz), 9.48 (1H, s), 10.46 (1H, br-s).

EXAMPLE 45

4-[(3-Chloro-4-methoxybenzyl)amino]-1-(2-hydroxy-6-azaspiro[3.4]oct-6-yl)-6-phthalazinecarbonitrile Hydrochloride

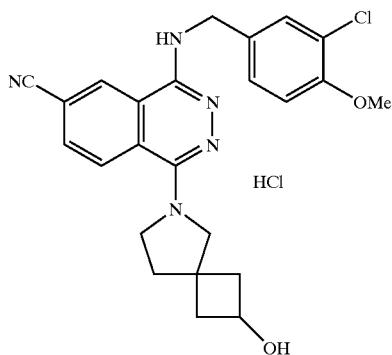

$^1$H-NMR (400 MHz, DMSO-d$_6$) δ; 1.00–1.08 (2H, m), 1.82–2.04 (4H, m), 2.19–2.35 (2H, m), 3.32–3.45 (2H, m), 3.55–3.60 (2H, m), 3.80 (3H, s), 4.04–4.19 (1H, m), 4.56 (2H, br-s), 7.10 (1H, d, J=8.4 Hz), 7.37 (1H, br-s), 7.50 (1H, br-s), 8.38 (1H, d, J=8.4 Hz), 8.45–8.73 (1H, m).

EXAMPLE 46

4-[(3-Chloro-4-methoxybenzyl)amino]-1-[3-(hydroxymethyl)-2,5-dihydro-1H-1-pyrrolyl]-6-phthalazinecarbonitrile Hydrochloride

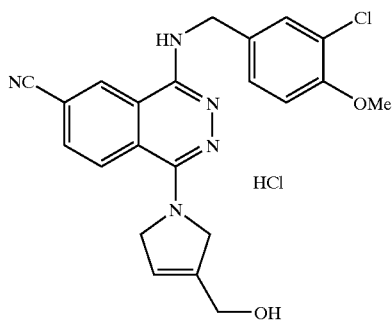

$^1$H-NMR (400 MHz, DMSO-d$_6$) δ; 3.82 (3H, s), 4.12 (2H, s), 4.45–4.83 (6H, m), 5.84 (1H, br-s), 7.11 (1H, d, J=9 Hz), 7.33–7.56 (2H, m), 8.45 (1H, d, J=9 Hz), 8.66–9.14 (2H, m).

EXAMPLE 47

4-[(3-Chloro-4-methoxybenzyl)amino]-1-[(3R,4S)-3,4-di(hydroxymethyl)tetrahydro-1H-1-pyrrolyl]-6-phthalazinecarbonitrile Hydrochloride

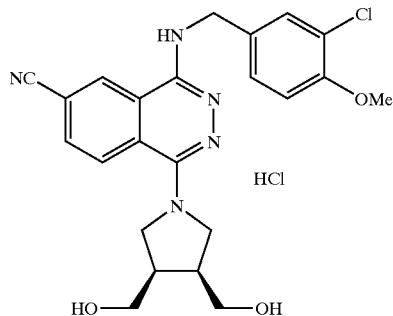

$^1$H-NMR (400 MHz, DMSO-d$_6$) δ; 2.50–2.57 (2H, m), 3.38–3.49 (2H, m), 3.56–3.60 (2H, m), 3.76–3.87 (4H, m), 3.81 (3H, s), 4.55 (2H, br-s), 7.10 (1H, d, J=8.4 Hz), 7.36 (1H, d, J=7.6 Hz), 7.49 (1H, s), 8.41 (1H, d, J=8.4 Hz), 8.68 (1H, d, J=8.4 Hz), 9.13 (1H, s).

EXAMPLE 48

1-[4-[(3-Chloro-4-methoxybenzyl)amino]-6-cyano-1-phthalazinyl]-4-hydroxy-4-piperidinecarboxamide Hydrochloride

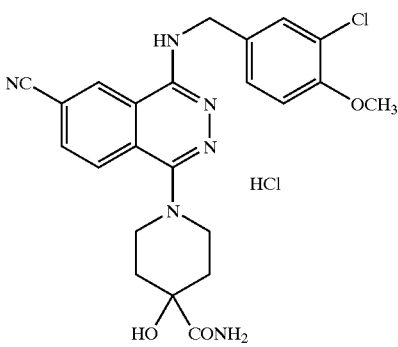

$^1$H-NMR (400 MHz, DMSO-d$_6$) δ; 1.56–1.64 (2H, m), 2.16–2.28 (2H, m), 3.12–3.24 (2H, m), 3.32–3.48 (2H, m), 3.54 (1H, brs), 3.83 (3H, s), 4.10–4.30 (1H, m), 4.74 (2H, s), 7.13 (1H, d, J=8.4 Hz), 7.15 (1H, br-s), 7.31 (1H, br-s), 7.48 (1H, d, J=8.4 Hz), 7.64 (1H, s), 8.26 (1H, d, J=8.4 Hz), 8.44 (1H, d, J=8.4 Hz), 9.52–9.60 (1H, m).

EXAMPLE 49

[4-(3-Chloro-4-methoxybenzyl)amino]-1-[4-(fluoromethyl)-4-hydroxypiperidino]-6-phthalazinecarbonitrile Hydrochloride

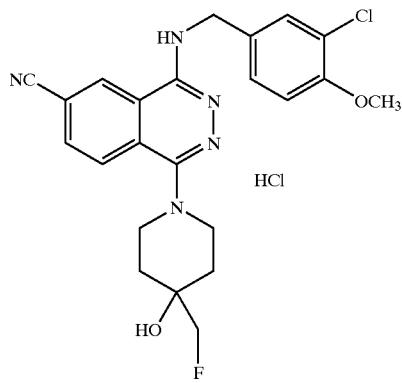

$^1$H-NMR (400 MHz, DMSO-$d_6$) δ; 1.54–1.64 (2H, m), 1.80–1.92 (2H, m), 3.18–3.26 (2H, m), 3.32–3.44 (4H, m), 3.83 (3H, s), 4.22 (2H, d, J=7.6 Hz), 4.72 (1H, d, J=6.0 Hz), 7.14 (1H, d, J=8.4 Hz), 7.48 (1H, dd, J=8.4, 1.6 Hz), 7.62 (1H, d, J=1.6 Hz), 8.23 (1H, d, J=8.4 Hz), 8.45 (1H, d, J=8.4 Hz), 9.45 (1H, br-s).

EXAMPLE 50

4-[(3-Chloro-4-methoxybenzyl)amino]-1-(4-hydroxyiminopiperidino)-6-phthalazinecarbonitrile Hydrochloride

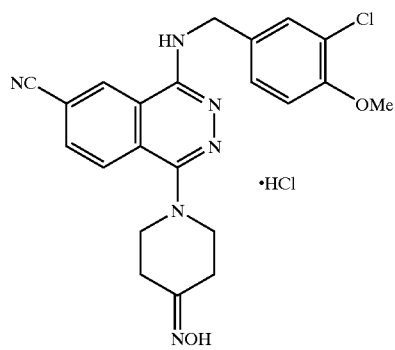

$^1$H-NMR (400 MHz, DMSO-$d_6$) δ; 2.50–2.52 (2H, m), 2.74–2.80 (2H, m), 3.26–3.35 (4H, m), 3.85 (3H, s), 4.71 (2H, br), 7.17 (1H, d, J=8.8 Hz), 7.45 (1H, dd, J=8.8, 2.0 Hz), 7.60 (1H, d, J=2.0 Hz), 8.34 (1H, d, J=8.4 Hz), 8.49 (1H, dd, J=8.4, 0.4 Hz), 9.34 (1H, d, J=0.4 Hz), 10.53 (1H, br).

EXAMPLE 51

(anti)-2-[3-[4-[(3-Chloro-4-methoxybenzyl)amino]-6-cyano-1-phthalazinyl]-3-azabicyclo[3.3.1]non-9-yl]acetic Acid Hydrochloride

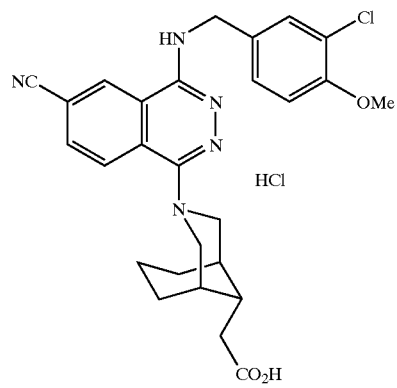

$^1$H-NMR (400 MHz, DMSO-$d_6$) δ; 1.62 (1H, m), 1.75–2.00 (4H, m), 2.12 (1H, m), 2.52 (2H, d, J=8.1 Hz), 3.16–3.24 (2H, m), 3.68–3.76 (2H, m), 3.85 (3H, s), 4.74 (2H, s), 7.16 (1H, d, J=8.6 Hz), 7.48 (1H, dd, J=1.8, 8.6 Hz), 7.62 (1H, d, J=1.8 Hz), 8.23 (1H, d, J=8.4 Hz), 8.55 (1H, dd, J=1.3, 8.4 Hz), 9.48 (1H, m).

EXAMPLE 52

(endo)-4-[(3-Chloro-4-methoxybenzyl)amino]-1-(3-hydroxy-8-azabicyclo[3.2.1]oct-8-yl)-6-phthalazinecarbonitrile Hydrochloride

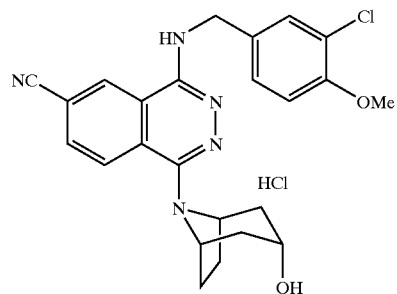

$^1$H-NMR (400 MHz, DMSO-$d_6$) δ; 1.81–1.88 (2H, m), 1.90–1.98 (2H, m), 2.19–2.30 (4H, m), 3.85 (3H, s), 4.04 (1H, m), 4.16–4.26 (2H, m), 4.71 (2H, s), 7.16 (1H, d, J=8.6 Hz), 7.46 (1H, d, J=8.6 Hz), 7.61 (1H, s), 8.29 (1H, d, J=8.4 Hz), 8.47 (1H, dd, J=1.3, 8.4 Hz), 9.44 (1H, m).

EXAMPLE 53

(syn)-4-[(3-Chloro-4-methoxybenzyl)amino]-1-(9-hydroxy-3-azabicyclo[3.3.1]non-3-yl)-6-phthalazinecarbonitrile Hydrochloride

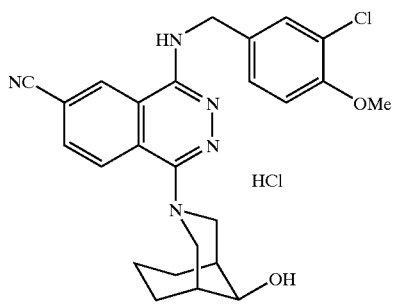

$^1$H-NMR (400 MHz, DMSO-d$_6$) δ; 1.53 (1H, m), 1.74–1.86 (2H, m), 1.87–1.93 (2H, m), 2.05–2.14 (2H, m), 2.37 (1H, m), 3.28–3.44 (2H, m), 3.41–3.61 (2H, m), 3.68 (1H, m), 3.85 (3H, s), 4.73 (2H, s), 7.15 (1H, d, J=8.6 Hz), 7.47 (1H, d, J=8.6 Hz), 7.62 (1H, s), 8.22 (1H, d, J=8.6 Hz), 8.54 (1H, d, J=8.6 Hz), 9.48 (1H, m).

EXAMPLE 54

(syn)-4-[(3-Chloro-4)amino]-1-(8-hydroxy-3-azabicyclo[3.2.1]oct-3-yl)-6-phthalazinecarbonitrile Hydrochloride

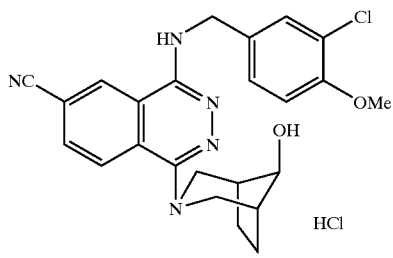

$^1$H-NMR (400 MHz, DMSO-d$_6$) δ; 1.75–1.96 (4H, m), 2.02–2.09 (2H, m), 3.06–3.18 (2H, m), 3.50–3.60 (2H, m), 3.86 (3H, s), 3.91 (1H, t, J=4.8 Hz), 4.73 (2H, s), 7.16 (1H, d, J=8.6 Hz), 7.47 (1H, d, J=8.6 Hz), 7.61 (1H, s), 8.36 (1H, d, J=8.6 Hz), 8.48 (1H, dd, J=1.5, 8.6 Hz), 9.43 (1H, m).

EXAMPLE 55

(exo)-4-[(3-chloro-4-methoxybenzyl)amino]-1-(3-hydroxy-8-azabicyclo[3.2.1]oct-8-yl)-6-phthalazinecarbonitrile Hydrochloride

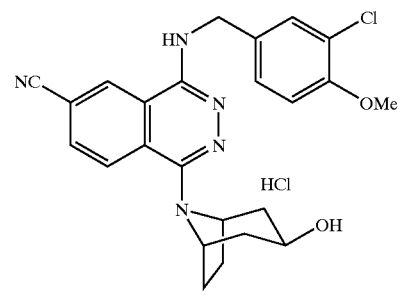

$^1$H-NMR (400 MHz, DMSO-d$_6$) δ; 6.68–1.83 (2H, m), 1.90–2.02 (4H, m), 3.85 (3H, s), 3.97 (1H, m), 4.18–4.28 (2H, m), 4.70 (2H, s), 7.15 (1H, d, J=8.6 Hz), 7.44 (1H, d, J=8.6 Hz), 7.59 (1H, s), 8.29 (1H, d, J=8.6 Hz), 8.45 (1H, d, J=8.6 Hz), 9.36 (1H, m).

EXAMPLE 56

(anti)-4-[(3-Chloro-4-methoxybenzyl)amino]-1-(9-hydroxy-3-oxa-7-azabicyclo[3.3.1]non-7-yl)-6-phthalazinecarbonitrile Hydrochloride

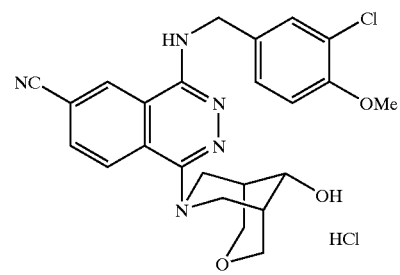

$^1$H NMR (DMSO-d$_6$) δ; 1.69–1.76 (2H, m), 3.24–3.38 (2H, m), 3.73–3.83 (2H, m), 3.85 (3H, s) 3.85–3.93 (2H, m), 4.11–4.20 (2H, m), 4.73 (2H, s), 7.16 (1H, d, J=8.6 Hz), 7.47 (1H, d, J=8.6 Hz), 7.62 (1H, s), 8.36 (1H, d, J=8.4 Hz), 8.52 (1H, d, J=8.4 Hz), 9.43 (1H, m).

EXAMPLE 57

(anti)-4-[(3-Chloro-4-methoxybenzyl)amino]-1-(3-hydroxy-9-azabicyclo[3.3.1]non-9-yl)-6-phthalazinecarbonitrile Hydrochloride

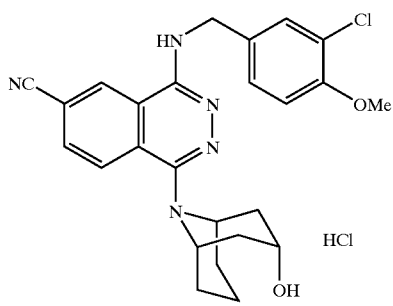

$^1$H-NMR (400 MHz, DMSO-d$_6$) δ; 1.38–1.54 (4H, m), 1.59 (1H, m), 1.90–2.02 (2H, m), 2.22–2.45 (3H, m), 3.86 (3H, s), 3.87 (1H, m), 4.08–4.17 (2H, m), 4.69 (2H, s), 7.16 (1H, d, J=8.6 Hz), 7.44 (1H, d, J=8.6 Hz), 7.58 (1H, s), 8.07 (1H, d, J=8.6 Hz), 8.44 (1H, d, J=8.6 Hz), 9.29 (1H, m).

EXAMPLE 58

N$^1$-[3-[4-[(3-Chloro-4-methoxybenzyl)amino]-6-cyano-1-phthalazinyl]phenyl]acetamide

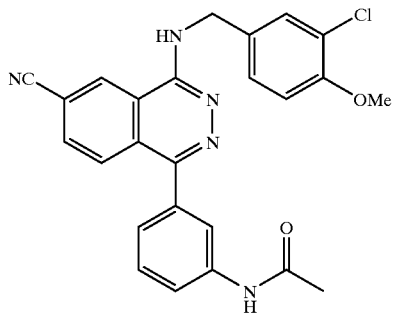

$^1$H-NMR (400 MHz, DMSO-d$_6$) δ; 2.0.5 (3H, s) 3.81 (3H, s) 4.76 (2H, d, J=6.0 Hz), 7.09 (1H, d, J=8.4 Hz), 7.24 (1H, d, J=8.0 Hz), 7.38 (1H, dd, J=8.0, 1.6 Hz), 7.45 (1H, dd, J=8.4, 8.0 Hz), 7.50 (1H, d, J=1.6 Hz), 7.67 (1H, d, J=8.0 Hz), 7.86 (1H, m), 7.92 (1H, d, J=8.4 Hz), 8.17 (1H, dd, J=8.4, 1.6 Hz), 8.35 (1H, dd, J=6.0, 6.0 Hz), 9.00 (1H, s), 10.09 (1H, s).

EXAMPLE 59

1-(3-Aminophenyl)-4-[(3-chloro-4-methoxybenzyl)amino]-6-phthalazinecarbonitrile Dihydrochloride

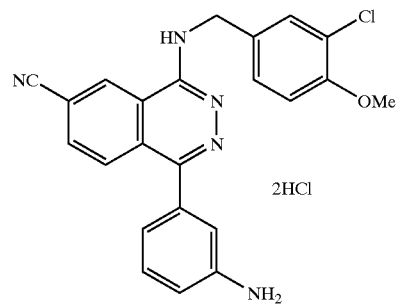

$^1$H-NMR (400 MHz, DMSO-d$_6$) δ; 3.83 (3H, s), 4.89 (2H, br-s), 7.16 (1H, d, J=8.6 Hz), 7.38–7.44 (3H, m), 7.53 (1H, dd, J=8.6, 2.0 Hz), 7.58–7.62 (2H, m), 7.68 (1H, d, J=2.0 Hz), 8.02 (1H, d, J=8.4 Hz), 8.45 (1H, d, J=8.4 Hz), 9.65 (1H, s).

EXAMPLE 60

N-[3-[4-[(3-Chloro-4-methoxybenzyl)amino]-6-cyano-1-phthalazinyl]phenyl]methanesulfonamide Hydrochloride

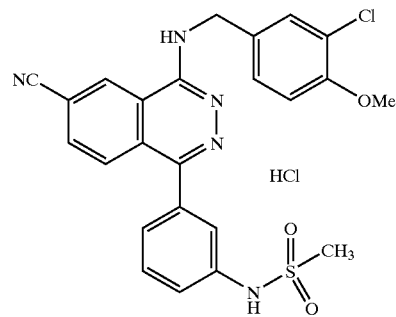

$^1$H-NMR (400 MHz, DMSO-d$_6$) δ; 3.06 (3H, s), 3.84 (3H, s), 4.86 (2H, d, J=5.6 Hz), 7.15 (1H, d, J=8.4 Hz), 7.35 (1H, d, J=7.6 Hz), 7.43 (1H, d, J=7.6 Hz), 7.50 (1H, br-s), 7.53 (1H, dd, J=8.4, 2.0 Hz), 7.55 (1H, dd, J=7.6, 7.6 Hz), 7.66 (1H, d, J=2.0 Hz), 8.03 (1H, d, J=8.8 Hz), 8.44 (1H, d, J=8.8 Hz), 9.60 (1H, br-s), 10.14 (1H, br-s)

EXAMPLE 61

4-[(3-Chloro-4-methoxybenzyl)amino]-1-[4-(methylsulfinyl)phenyl]-6-phthalazinecarbonitrile Hydrochloride

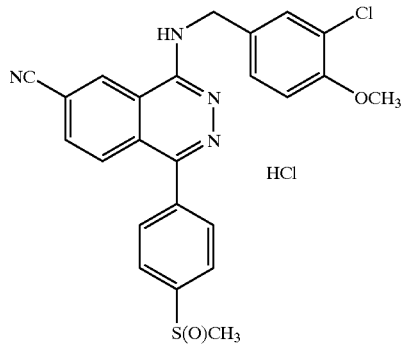

$^1$H-NMR (400 MHz, DMSO-d$_6$) δ; 2.84 (3H, s), 3.83 (3H, s), 4.87 (2H, br-s), 7.16 (1H, d, J=8.4 Hz), 7.51 (1H, d, J=8.4 Hz), 7.66 (1H, br-s), 7.83 (2H, d, J=8.4 Hz), 7.92 (2H, d, J=8.4 Hz), 8.00 (1H, d, J=8.4 Hz), 8.43 (1H, d, J=8.4 Hz), 9.52–9.60 (1H, m).

EXAMPLE 62

4-[(3-Chloro-4-methoxybenzyl)amino]-1-(4-(methylsulfonyl)phenyl]-6-phthalazinecarbonitrile Hydrochloride

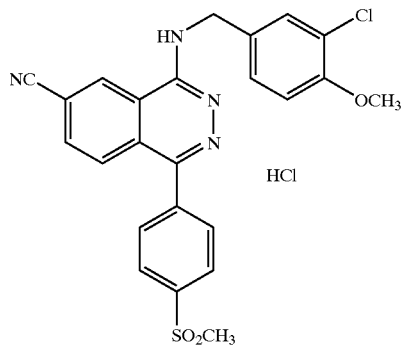

$^1$H-NMR (400 MHz, DMSO-d$_6$) δ; 3.31 (3H, s), 3.82 (3H, s), 4.80 (2H, br-s), 7.12 (1H, d, J=8.8 Hz), 7.43 (1H, dd, J=8.8, 2.0 Hz), 7.56 (1H, d, J=2.0 Hz), 7.90 (2H, d, J=8.0 Hz), 7.93 (1H, d, J=8.4 Hz), 8.11 (2H, d, J=8.0 Hz), 8.28 (1H, d, J=8.4 Hz), 9.19–9.22 (1H, m).

EXAMPLE 63

4-[(3-Chloro-4-methoxybenzyl)amino]-1-(4-formylphenyl)-6-phthalazinecarbonitrile Hydrochloride

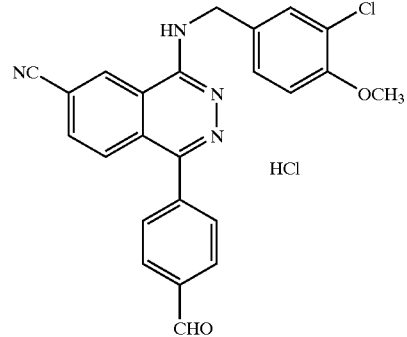

$^1$H-NMR (400 MHz, DMSO-d$_6$) δ; 3.84 (3H, s), 4.86 (2H, br-s), 7.16 (1H, d, J=8.4 Hz), 7.51 (1H, d, J=8.4 Hz), 7.66 (1H, br-s), 7.86 (2H, d, J=8.0 Hz), 7.99 (1H, d, J=8.8 Hz), 8.13 (2H, d, J=8.0 Hz), 8.42 (1H, d, J=8.8 Hz), 9.48–9.53 (1H, m), 10.15 (1H, s).

EXAMPLE 64

4-[(3-Chloro-4-methoxybenzyl)amino]-1-[4-hydroxymethyl)phenyl]-6-phthalazinecarbonitrile Hydrochloride

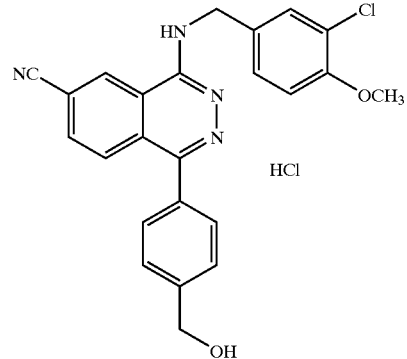

$^1$H-NMR (400 MHz, DMSO-d$_6$) δ; 3.84 (3H, s), 4.62 (2H, s), 4.84 (2H, br-s), 7.16 (1H, d, J=8.4 Hz), 7.49 (1H, dd, J=8.4, 2.0 Hz), 7.55 (2H, d, J=8.0 Hz), 7.60 (2H, d, J=8.0 Hz), 7.65 (1H, d, J=2.0 Hz), 8.02 (1H, d, J=8.4 Hz), 8.43 (1H, d, J=8.4 Hz), 9.50–9.58 (1H, m).

EXAMPLE 65

4-[4-[(3-Chloro-4-methoxybenzyl)amino]-6-cyano-1-phthalazinyl]benzoic Acid

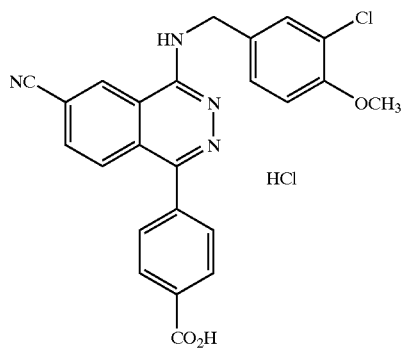

$^1$H-NMR (400 MHz, DMSO-$d_6$) δ; 3.84 (3H, s), 4.76 (2H, d, J=6.0 Hz), 7.10 (1H, d, J=8.8 Hz), 7.38 (1H, dd, J=8.8, 2.0 Hz), 7.50 (1H, d, J=2.0 Hz), 7.72 (2H, d, J=8.4 Hz), 7.91 (1H, d, J=8.8 Hz), 8.08 (2H, d, J=8.4 Hz), 8.19 (1H, dd, J=8.4, 1.6 Hz), 8.44 (1H, dd, J=6.0, 6.0 Hz), 9.01 (1H, d, J=1.6 Hz).

EXAMPLE 66

4-[(3-Chloro-4-methoxybenzyl)amino]-1-(1,3-thiazol-2-yl)-6-phthalazinecarbonitrile Hydrochloride

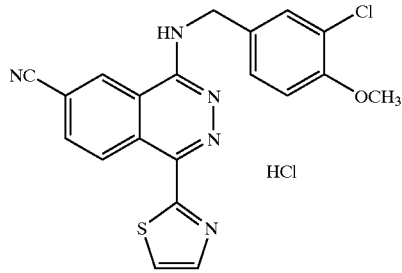

$^1$H-NMR (400 MHz, DMSO-$d_6$) δ; 3.80 (3H, s), 4.82 (2H, s), 7.13 (1H, d, J=8.4 Hz), 7.42 (1H, d, J=8.4 Hz), 7.57 (1H, s), 7.94 (1H, d, J=3.6 Hz), 8.11 (1H, d, J=3.6 Hz), 8.46 (1H, d, J=8.4 Hz), 9.20–9.26 (1H, m), 9.70 (1H, d, J=8.4 Hz).

EXAMPLE 67

4-[(3-Chloro-4-methoxybenzyl)amino]-1-(3-hydroxy-3-methyl-1-butynyl)-6-phthalazinecarbonitrile Hydrochloride

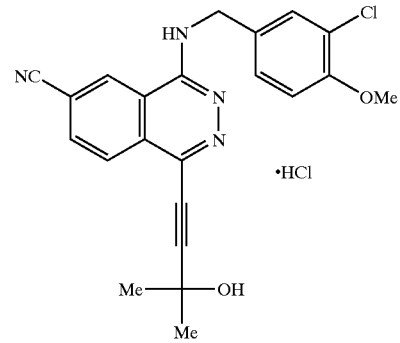

$^1$H-NMR (400 MHz, DMSO-$d_6$) δ; 1.57 (6H, s), 3.84 (3H, s), 4.84 (2H, s), 7.15 (1H, d, J=8.8 Hz), 7.46 (1H, dd, J=8.8, 2.0 Hz), 7.61 (1H, d, J=2.0 Hz), 8.34 (1H, d, J=8.4 Hz), 8.52 (1H, dd, J=8.4, 0.4 Hz), 9.04 (1H, d, J=0.4 Hz), 10.36 (1H, br).

EXAMPLE 68

4-[(3-Chloro-4-methoxybenzyl)amino]-1-(3-hydroxy-1-propynyl)-6-phthalazinecarbonitrile Hydrochloride

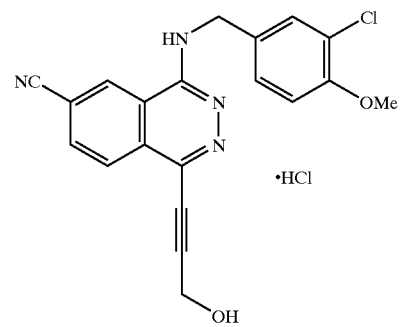

$^1$H-NMR (400 MHz, DMSO-$d_6$) δ; 3.84 (3H, s), 4.49 (2H, s), 4.81 (2H, d, J=4.0 Hz), 7.14 (1H, d, J=8.4 Hz), 7.43 (1H, dd, J=8.4, 2.4 Hz), 7.58 (1H, d, J=2.4 Hz), 8.35 (1H, d, J=8.8 Hz), 8.48 (1H, dd, J=8.8, 0.8 Hz), 9.28 (1H, d, J=0.8 Hz), 9.92 (1H, br).

EXAMPLE 69

4-[(3-Chloro-4-methoxybenzyl)amino]-1-(3,4-dihydroxy-3-(hydroxymethyl)-1-butynyl-6-phthalazine Carbonitrile

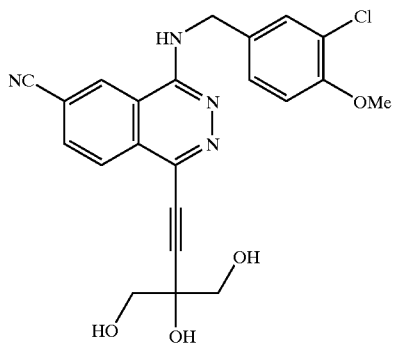

¹H-NMR (400 MHz, DMSO-d₆) δ; 3.54–3.66 (4H, m), 3.82 (3H, s), 4.76 (2H, d, J=5.2 Hz), 4.98 (2H, t, J=5.2 Hz), 5.62 (1H, s), 7.10 (1H, d, J=8.8 Hz), 7.36 (1H, dd, J=8.8, 2.0 Hz), 7.49 (1H, d, J=2.0 Hz), 8.29–8.34 (1H, m), 8.51 (1H, t, J=5.2 Hz), 8.96 (1H, s).

EXAMPLE 70

4-[(3-Chloro-4-methoxybenzyl)amino]-1-[3-(dimethylamino)-1-propynyl]-6-phthalazinecarbonitrile Dihydrochloride

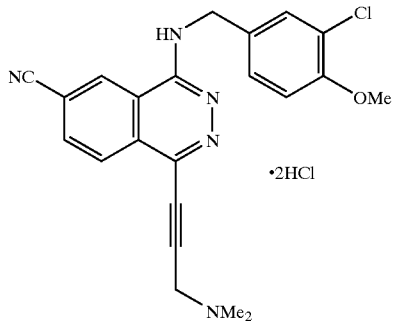

¹H-NMR (400 MHz, DMSO-d₆) δ; 2.91 (6H, s), 3.83 (3H, s), 4.52 (2H, s), 4.83 (2H, d, J=4.8 Hz), 7.13 (1H, d, J=8.8 Hz), 7.42 (1H, dd, J=8.8, 2.0 Hz), 7.56 (1H, d, J=2.0 Hz), 8.40 (1H, dd, J=8.4, 1.4 Hz), 8.46 (1H, d, J=8.4 Hz), 9.27 (1H, d, J=1.4 Hz), 9.76 (1H, br), 11.39 (1H, br).

EXAMPLE 71

2-[[3-[4-[(3-Chloro-4-methoxybenzyl)amino]-6-cyano-1-phthalazinyl]-1,1-dimethyl-2-propynyl]oxy] acetic Acid Hydrochloride

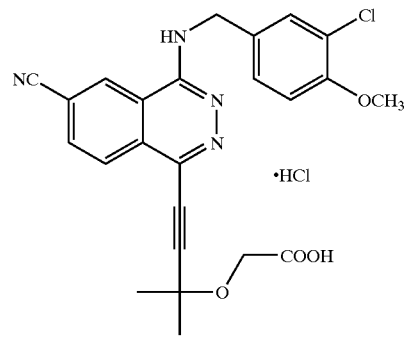

¹H-NMR (400 MHz, DMSO-d₆) δ; 1.62 (6H, s), 3.84 (3H, s), 4.21–4.24 (2H, m), 4.77–4.82 (2H, br), 7.11–7.15 (1H, m), 7.38–7.42 (1H, m), 7.51–7.55 (1H, m), 8.19–8.24 (1H, m), 8.38–8.42 (1H, m), 9.12–9.16 (1H, m).

EXAMPLE 72

4-[(3-Chloro-4-methoxybenzyl)amino]-1-[3-(2-hydroxyethoxy)-3-methyl-1-butynyl]-6-phthalazinecarbonitrile Hydrochloride

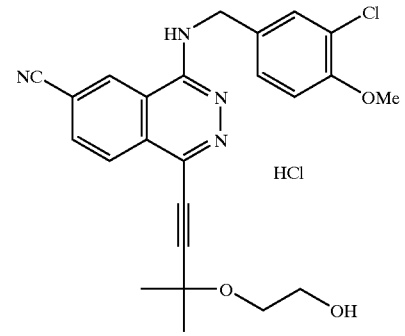

¹H-NMR (400 MHz, DMSO-d₆) δ; 1.61 (6H, s), 3.55 (2H, t, J=5.6 Hz), 3.65 (2H, t, J=5.6 Hz), 3.84 (3H, s), 4.85 (2H, d, J=4.8 Hz), 7.14 (1H, d, J=8.6 Hz), 7.46 (1H, dd, J=8.6, 2.2 Hz), 7.61 (1H, d, J=2.2 Hz), 8.30 (1H, d, J=8.4 Hz), 8.48 (1H, dd, J=8.4, 1.6 Hz), 9.42 (1H, d, J=1.6 Hz), 10.41 (1H, br).

EXAMPLE 73

4-[(3-Chloro-4-methoxybenzyl)amino]-1-[3-(4-hydroxypiperidino)-3-methyl-1-butynyl]-6-phthalazinecarbonitrile Dihydrochloride

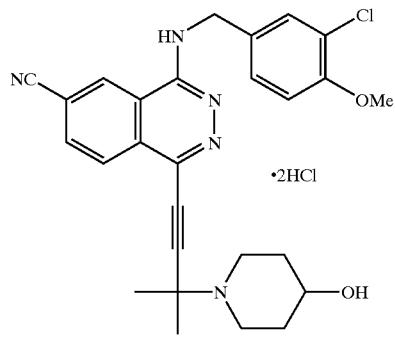

$^1$H-NMR (400 MHz, DMSO-$d_6$) δ; 1.79–2.04 (10H, m), 2.12–2.23 (1H, m)), 3.04–3.19 (1H, m), 3.26–3.37 (2H, m), 3.54–3.77 (1H, m), 3.82 (3H, s), 4.83 (2H, d, J=5.6 Hz), 7.12 (1H, d, J=8.4 Hz), 7.43 (1H, dd, J=8.4, 1.2 Hz), 7.56 (1H, d, J=1.2 Hz), 8.38 (1H, dd, J=8.4, 0.8 Hz), 8.43 (1H, d, J=8.4 Hz), 9.30 (1H, d, J=0.8 Hz), 9.91 (1H, br), 11.40–11.66 (1H, m).

EXAMPLE 74

4-[(3-Chloro-4-methoxybenzyl)amino]-1-(3-methyl-3-tetrahydro-1H-1-pyrrolyl-1-butynyl)-6-phthalazinecarbonitrile Dihydrochloride

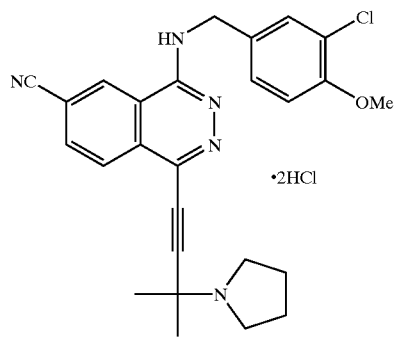

$^1$H-NMR (400 MHz, DMSO-$d_6$) δ; 1.85 (6H, s), 1.90–2.08 (4H, m), 3.30–3.42 (2H, m), 3.60–3.72 (2H, m), 3.83 (3H, s), 4.80 (2H, d, J=5.2 Hz), 7.11 (1H, d, J=8.4 Hz), 7.39 (1H, dd, J=8.4, 2.0 Hz), 7.52 (1H, d, J=2.0 Hz), 8.28 (1H, d, J=8.4 Hz), 8.36 (1H, dd, J=8.4, 0.8 Hz), 9.14 (1H, d, J=0.8 Hz), 9.33 (1H,br), 11.89 (1H, m).

EXAMPLE 75

1-(4-Hydroxypiperidino)-4-[[4-methoxy-3-(trifluoromethyl)benzyl]amino]-6-phthalazinecarbonitrile Hydrochloride

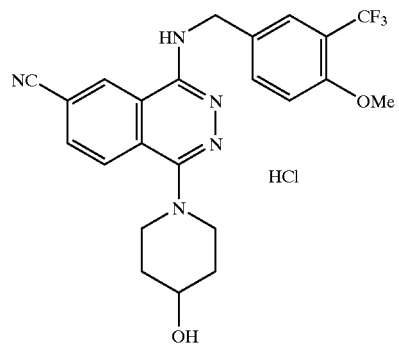

$^1$H-NMR (400 MHz, DMSO-$d_6$) δ; 1.62–1.73 (2H, m), 1.90–1.99 (2H, m), 2.97–3.07 (2H, m), 3.40–3.52 (2H, m), 3.72–3.80 (1H, m), 3.89 (3H, s), 4.80 (2H, d, J=5.6 Hz), 7.28 (1H, d, J=8.4 Hz), 7.81–7.85 (2H, m), 8.24 (1H, d, J=8.4 Hz), 8.47 (1H, dd, J=8.4, 1.2 Hz), 9.53 (1H, d, J=1.2 Hz), 10.29 (1H, br), 14.02 (1H, br).

EXAMPLE 76

1-(4-Hydroxypiperidino)-4-[(3-iodo-4-methoxybenzyl)amino]-6-phthalazinecarbonitrile Hydrochloride

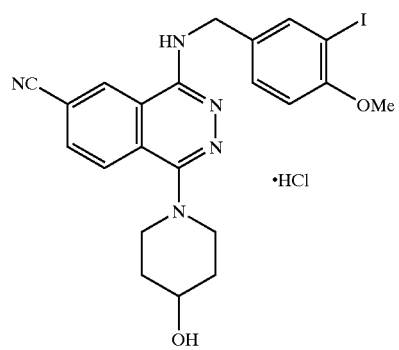

$^1$H-NMR (400 MHz, DMSO-$d_6$); δ; 1.62–1.73 (2H, m), 1.90–2.00 (2H, m), 2.98–3.08 (2H, m), 3.40–3.50 (2H, m), 3.72–3.80 (1H, m), 3.82 (3H, s), 4.68 (2H, d, J=4.8 Hz), 7.02 (1H, d, J=8.8 Hz), 7.50 (1H, dd, J=8.8, 2.2 Hz), 7.93 (1H, d, J=2.2 Hz), 8.24 (1H, d, J=8.6 Hz), 8.46 (1H, dd, J=8.6, 0.8 Hz), 9.32 (1H, d, J=0.8 Hz), 10.05 (1H, br).

EXAMPLE 77

4-[(3-Bromo-4-methoxybenzyl)amino]-1-(4-hydroxypiperidino)-6-phthalazinecarbonitrile Hydrochloride

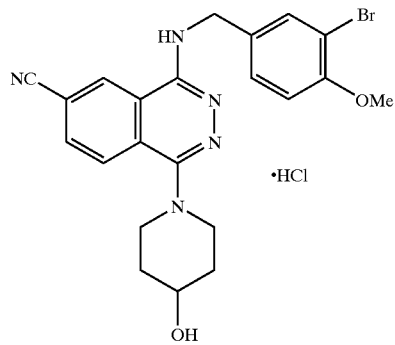

$^1$H-NMR (400 MHz, DMSO-d$_6$) δ; 1.62–1.73 (2H, m), 1.90–1.99 (2H, m), 2.98–3.07 (2H, m), 3.39–3.50 (2H, m), 3.72–3.80 (1H, m), 3.84 (3H, s), 4.71 (2H, d, J=4.8 Hz), 7.13 (1H, d, J=8.6 Hz), 7.49 (1H, dd, J=8.6, 2.2 Hz), 7.75 (1H, d, J=2.2 Hz), 8.24 (1H, d, J=8.4 Hz), 8.46 (1H, dd, J=8.4, 0.8 Hz), 9.34 (1H, d, J=0.8 Hz), 10.11 (1H, br).

EXAMPLE 78

4-[(3-Bromo-4-methoxybenzyl)amino]-1-[3-(hydroxymethyl)tetrahydro-1H-1-pyrrolyl]-6-phthalazinecarbonitrile Hydrochloride

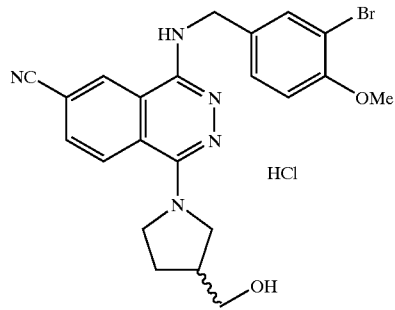

$^1$H-NMR (400 MHz, DMSO-d$_6$) δ; 1.72–1.86 (1H, m), 1.99–2.12 (1H, m), 2.39–2.51 (1H, m), 3.42 (1H, dd, J=7.2, 10.8 Hz), 3.48 (1H, dd, J=6.0, 10.8 Hz), 3.60–3.90 (4H, m), 3.80 (3H, s), 7.06 (1H, d, J=8.4 Hz), 7.38–7.46 (1H, m), 7.64 (1H, s), 8.40 (1H, dd, J=1.6, 8.8 Hz), 8.65 (1H, d, J=8.0 Hz), 9.18 (1H, s).

EXAMPLE 79

4-[(3-Bromo-4-methoxybenzyl)amino]-1-[(3S)-3-(hydroxymethyl)tetrahydro-1H-1-pyrrolyl]-6-phthalazinecarbonitrile Hydrochloride

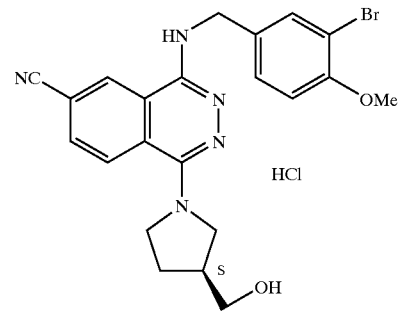

$^1$H-NMR (400 MHz, DMSO-d$_6$) δ; 1.58–1.76 (3H, m), 1.92–2.02 (2H, m), 2.29–2.42 (2H, m), 3.42–3.60 (2H, m), 3.78 (3H, s), 4.58 (2H, J=6.0 Hz), 4.69 (1H, t, J=5.6 Hz), 7.03 (1H, d, J=8.4 Hz), 7.36 (1H, dd, J=2.0, 8.4 Hz), 7.57 (1H, d, J=2.0 Hz), 7.59 (1H, d, J=6.0 Hz), 8.13 (1H, dd, J=1.2, 8.8 Hz), 8.22 (1H, d, J=8.8 Hz), 8.81 (1H, d, J=0.8 Hz).

EXAMPLE 80

4-[(3-Bromo-4-methoxybenzyl)amino]-1-[(3R)-3-(hydroxymethyl)tetrahydro-1H-1-pyrrolyl]-6-phthalazinecarbonitrile Hydrochloride

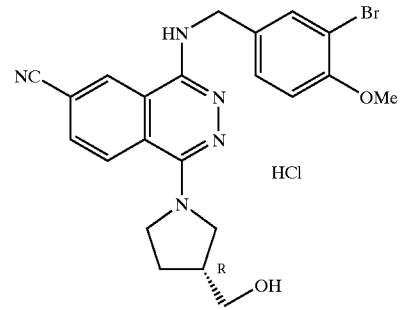

$^1$H-NMR (400 MHz, DMSO-d$_6$) δ; 1.72–1.86 (1H, m), 1.99–2.12 (1H, m), 2.39–2.51 (1H, m), 3.42 (1H, dd, J=7.2, 10.8 Hz), 3.48 (1H, dd, J=6.0, 10.8 Hz), 3.60–3.90 (4H, m), 3.80 (3H, s), 7.06 (1H, d, J=8.8 Hz), 7.38–7.46 (1H, m), 7.65 (1H, s), 8.40 (1H, d, J=8.8 Hz), 8.59–8.68 (1H, m), 9.26 (1H, s).

EXAMPLE 81

4-[(3-Bromo-4-methoxybenzyl)amino]-1-[4-(2-hydroxyethyl)piperidino]-6-phthalazinecarbonitrile Hydrochloride

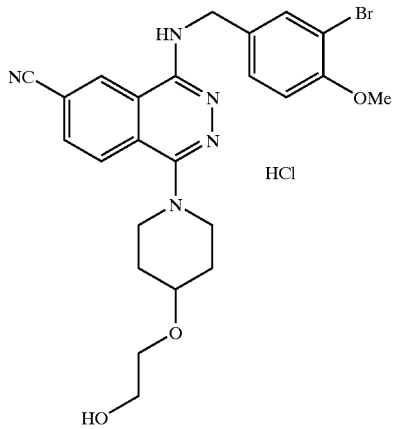

$^1$H-NMR (400 MHz, DMSO-d$_6$) δ; 1.68–1.77 (2H, m), 1.96–2.07 (2H, m), 3.02 (2H, t, J=12.0 Hz), 3.38–3.59 (6H, m), 3.80 (3H, s), 3.81–3.99 (3H, m), 4.72 (2H, d, J=6.0 Hz), 7.10 (1H, d, J=8.6 Hz), 7.49 (1H, d, J=8.6 Hz), 7.76 (1H, s), 8.22 (1H, d, J=8.6 Hz), 8.45 (1H, d, J=8.6 Hz), 9.50 (1H, s).

EXAMPLE 82

4-[(3-Bromo-4-methoxybenzyl)amino]-1-(2-hydroxy-7-azaspiro[3.5]non-7-yl)-6-phthalazinecarbonitrile Hydrochloride

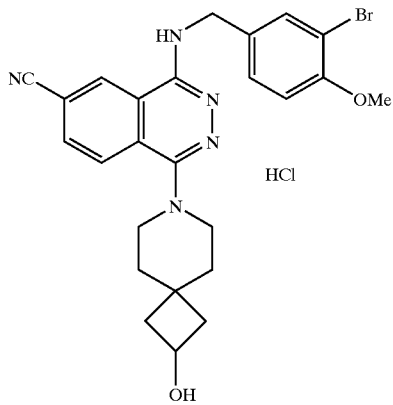

$^1$H-NMR (400 MHz, DMSO-d$_6$) δ; 1.58–1.66 (2H, m), 1.68–1.76 (4H, m), 2.14–2.23 (2H, m), 3.08 (2H, br-s), 3.13 (2H, br-s), 4.08–4.17 (1H, m), 4.73 (1H, d, J=5.6 Hz), 7.10 (1H, d, J=8.4 Hz), 7.52 (1H, dd, J=2.0, 8.4 Hz), 7.70 (1H, d, J=2.0 Hz), 8.20 (1H, d, J=8.4 Hz), 8.44 (1H, dd, J=1.6, 8.4 Hz), 9.55 (1H, s).

EXAMPLE 83

4-[(3-Bromo-4-methoxybenzyl)amino]-1-[4-fluoro-4-(hydroxymethyl)piperidino]-6-phthalazinecarbonitrile Hydrochloride

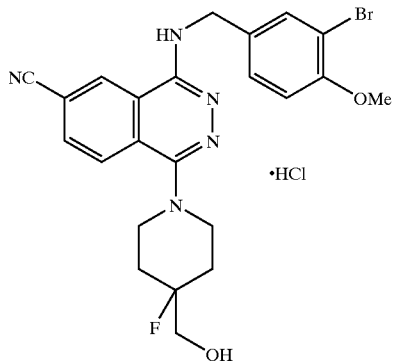

EXAMPLE 84

4-[(3-Bromo-4-methoxybenzyl)amino]-1-[4-(hydroxymethyl)piperidino]-6-phthalazinecarbonitrile Hydrochloride

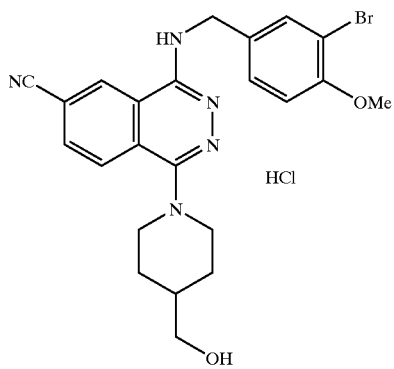

$^1$H-NMR (400 MHz, DMSO-d$_6$) δ; 1.41–1.52 (2H, m), 1.58–1.69 (1H, m), 1.79–1.86 (2H, m), 2.85–2.94 (2H, m), 3.35–3.40 (2H, m), 3.59 (2H, d, J=12.8 Hz), 3.84 (3H, s), 4.71 (2H, d, J=5.2 Hz), 7.13 (1H, d, J=8.4 Hz), 7.50 (1H, dd, J=8.4, 2.0 Hz), 7.76 (1H, d, J=2.0 Hz), 8.22 (1H, d, J=8.4 Hz), 8.47 (1H, dd, J=8.4, 0.8 Hz), 9.38 (1H, br), 10.21 (1H, br).

EXAMPLE 85

(endo)-4-[(3-Bromo-4-methoxybenzyl)amino]-1-(3-hydroxy-8-azabicyclo[3.2.1]octo-8-yl)-6-phthalazine Carbonitrile

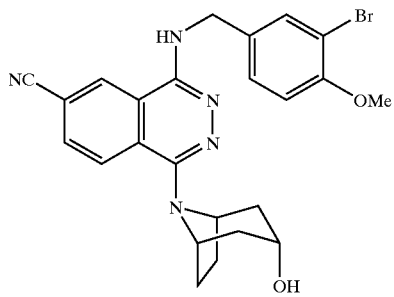

¹H-NMR (400 MHz, DMSO-d₆) δ; 1.70–1.95 (4H, m), 2.14–2.28 (4H, m), 3.82 (3H, s), 4.15 (1H, m), 4.09 (2H, m), 4.49 (1H, d, J=2.2 Hz), 4.62 (2H, d, J=5.5 Hz), 7.05 (1H, d, J=8.6 Hz), 7.38 (1H, dd, J=2.2, 8.6 Hz), 7.60 (1H, d, J=2.2 Hz), 7.72 (1H, t, J=5.5 Hz), 8.11 (1H, d, J=8.6 Hz), 8.18 (1H, dd, J=1.5, 8.6 Hz), 8.87 (1H, d, J=1.5 Hz).

EXAMPLE 86

1-(4-Hydroxypiperidino)-4-[(4-methoxy-3-methylbenzyl)amino]-6-phthalazinecarbonitrile Hydrochloride

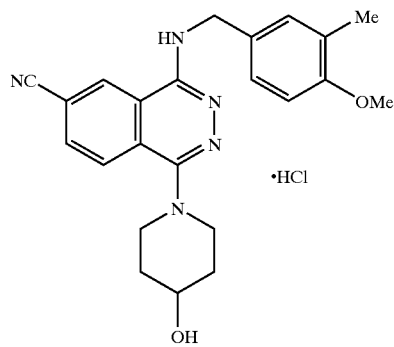

¹H-NMR (400 MHz, DMSO-d₆) δ; 1.62–1.73 (2H, m), 1.90–1.99 (2H, m), 2.15 (3H, s), 2.98–3.07 (2H, m), 3.42–3.50 (2H, m), 3.72–3.80 (1H, m), 3.78 (3H, s), 4.67–4.70 (2H, m), 6.94 (1H, d, J=8.2 Hz), 7.28 (1H, d, J=2.0 Hz), 7.31 (1H, dd, J=8.2, 2.0 Hz), 8.23 (1H, d, J=8.4 Hz), 8.47 (1H, dd, J=8.4, 1.2 Hz), 9.45 (1H, d, J=1.2 Hz), 10.39 (1H, br).

EXAMPLE 87

1-(2-Hydroxy-7-azaspiro[3.5]non-7-yl)-4-[(4-methoxy-3-methylbenzyl)amino]-6-phthalazinecarbonitrile Hydrochloride

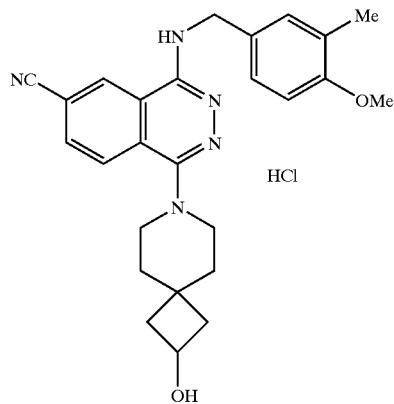

¹H-NMR (400 MHz, DMSO-d₆) δ; 1.57–1.66 (2H, m), 1.67–1.8 (4H, m), 2.11 (3H, s), 2.14–2.23 (2H, m), 3.07 (2H, br-s), 3.12 (2H, br-s), 3.55–3.61 (1H, m), 4.07–4.17 (1H, m), 4.69 (1H, d, J=5.2 Hz), 6.91 (1H, d, J=8.4 Hz), 7.29 (1H, s), 7.31 (1H, dd, J=2.0, 8.4 Hz), 8.19 (1H, d, J=8.4 Hz), 8.44 (1H, dd, J=1.2, 8.4 Hz), 9.56 (1H, s), 10.59 (1H, br-s).

EXAMPLE 88

1-[4-Fluoro-4-(hydroxymethyl)piperidino]-4-[(4-methoxy-3-methylbenzyl)amino]-6-phthalazinecarbonitrile Hydrochloride

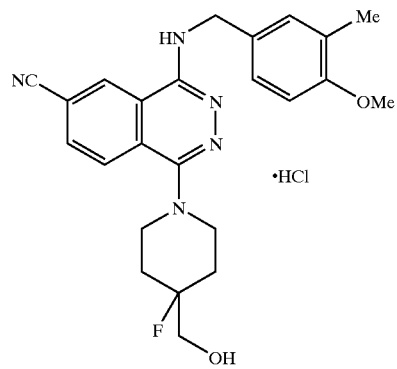

¹H-NMR (400 MHz, DMSO-d₆) δ; 1.88–2.10 (4H, m), 2.15 (3H, s), 3.08–3.17 (2H, m), 3.40–3.50 (2H, m), 3.51 (2H, d, J=19.6 Hz), 3.78 (3H, s), 4.68 (2H, d, J=5.2 Hz), 6.94 (1H, d, J=8.0 Hz), 7.28–7.33 (2H, m), 8.28 (1H, d, J=8.4 Hz), 8.47 (1H, dd, J=8.4, 1.4 Hz), 9.42 (1H, dd, J=1.4 Hz), 10.26 (1H, br), 13.96 (1H, br).

EXAMPLE 89

1-[4-(Hydroxymethyl)piperidino]-4-[(3-methoxy-4-methylbenzyl)amino]-6-phthalazinecarbonitrile Hydrochloride

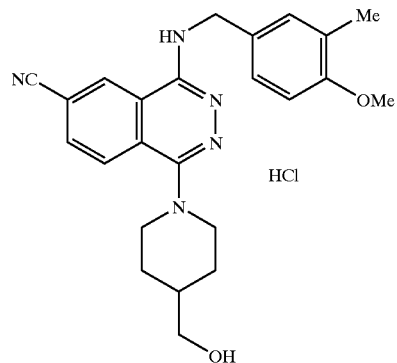

¹H-NMR (400 MHz, DMSO-d₆) δ; 1.41–1.52 (2H, m), 1.58–1.68 (1H, m), 1.79–1.87 (2H, m), 2.15 (3H, s), 2.82–2.93 (2H, m), 3.30–3.40 (2H, m), 3.58 (2H, d, J=12.8 Hz), 3.78 (3H, s), 4.67 (2H, d, J=5.2 Hz), 6.94 (1H, d, J=8.8 Hz), 7.26–7.32 (2H, m), 8.22 (1H, d, J=8.4 Hz), 8.47 (1H, dd, J=8.4, 0.8 Hz), 9.36 (1H, br), 10.09 (1H, br).

EXAMPLE 90

(endo)-1-(3-Hydroxy-8-azabicyclo[3.2.1]octo-8-yl)-4-[(4-methoxy-3-methylbenzyl)amino]-6-phthalazine Carbonitrile

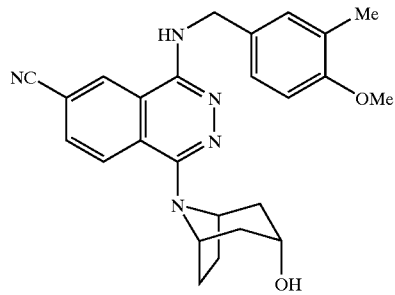

$^1$H-NMR (400 MHz, DMSO-d$_6$) δ; 1.79–1.93 (4H, m), 2.13 (3H, s), 2.13–2.27 (4H, m), 3.75 (3H, s), 4.03 (1H, m), 4.08 (2H, m), 4.49 (1H, d, J=2.2 Hz), 4.59 (2H, d, J=5.3 Hz), 6.87 (1H, d, J=7.9 Hz), 7.16–7.22 (2H, m), 7.61 (1H, t, J=5.3 Hz), 8.11 (1H, d, J=8.4 Hz), 8.17 (1H, dd, J=1.5, 8.4 Hz), 8.90 (1H, d, J=1.5 Hz).

$^1$H-NMR (400 MHz, DMSO-d$_6$) δ; 1.79–1.93 (4H, m), 2.13 (3H, s), 2.13–2.27 (4H, m), 3.75 (3H, s), 4.03 (1H, m), 4.08 (2H, m), 4.49 (1H, d, J=2.2 Hz), 4.59 (2H, d, J=5.3 Hz), 6.87 (1H, d, J=7.9 Hz), 7.16–7.22 (2H, m), 7.61 (1H, t, J=5.3 Hz), 8.11 (1H, d, J=8.4 Hz), 8.17 (1H, dd, J=1.5, 8.4 Hz), 8.90 (1H, d, J=1.5 Hz).

EXAMPLE 91

1-[3-(Hydroxymethyl)tetrahydro-1H-1-pyrrolyl]-4-[(4-methoxy-3-methylbenzyl)amino]-6-phthalazine Carbonitrile

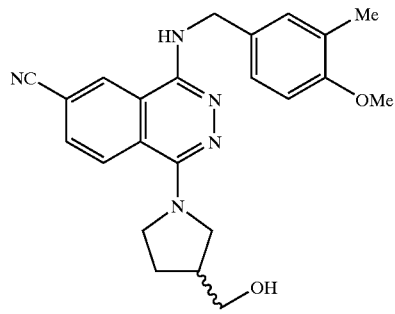

$^1$H-NMR (400 MHz, DMSO-d$_6$) δ; 1.67 (1H, m), 2.00 (1H, m), 2.16 (3H, s), 2.38 (1H, m), 3.36–3.61 (6H, m), 3.75 (3H, s), 4.58 (2H, d, J=5.5 Hz), 4.68 (1H, t, J=5.5 Hz), 6.86 (1H, d, J=8.1 Hz), 7.16–7.22 (2H, m), 7.50 (1H, t, J=5.3 Hz), 8.15 (1H, dd, J=1.5, 8.6 Hz), 8.24 (1H, dd, J=8.6 Hz), 8.88 (1H, d, J=1.5 Hz).

EXAMPLE 92

4-[(3-Fluoro-4-methoxybenzyl)amino]-1-(4-hydroxypiperidino)-6-phthalazine Carbonitrile

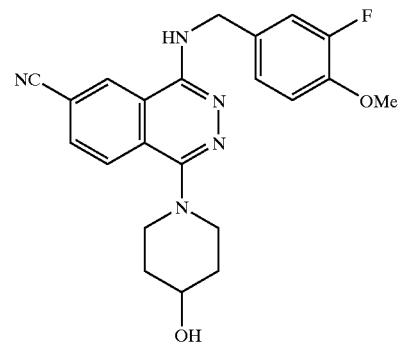

$^1$H-NMR (400 MHz, DMSO-d$_6$) δ; 1.60–1.73 (2H, m), 1.88–1.97 (2H, m), 2.86–2.94 (2H, m), 3.42–3.50 (2H, m), 3.64–3.71 (1H, m), 3.80 (3H, s), 4.62 (2H, d, J=5.4 Hz), 4.77 (1H, d, J=2.0 Hz), 7.09 (1H, t, J=8.2 Hz), 7.18 (1H, d, J=8.2 Hz), 7.23 (1H, dd, J=12.0, 2.0 Hz), 7.84 (1H, t, J=5.4 Hz), 8.04 (1H, d, J=8.4 Hz), 8.20 (1H, dd, J=8.4, 1.2 Hz), 8.89 (1H, d, J=1.2 Hz).

EXAMPLE 93

4-[(4-Chloro-3-methoxybenzyl)amino]-1-(4-hydroxypiperidino)-6-phthalazine Carbonitrile

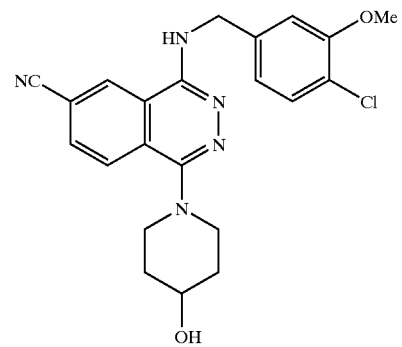

$^1$H-NMR (400 MHz, DMSO-d$_6$) δ; 1.60–1.72 (2H, m), 1.87–1.96 (2H, m), 2.86–2.95 (2H, m), 3.31–3.39 (2H, m), 3.68 (1H, m), 3.84 (3H, s), 4.72 (2H, d, J=5.5 Hz), 4.74 (1H, d, J=4.2 Hz), 6.98 (1H, dd, J=1.8, 8.1 Hz), 7.20 (1H, d, J=1.8 Hz), 7.34 (1H, d, J=8.1 Hz), 7.92 (1H, t, J=5.5 Hz), 8.07 (1H, d, J=8.6 Hz), 8.21 (1H, dd, J=1.5, 8.6 Hz), 8.92 (1H, d, J=1.5 Hz).

EXAMPLE 94

4-[(3-Cyano-4-methoxybenzyl)amino]-1-(4-hydroxypiperidino)-6-phthalazinecarbonitrile Hydrochloride

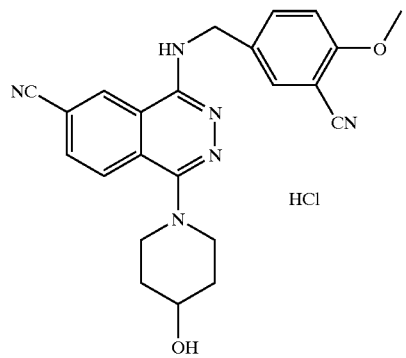

¹H-NMR (400 MHz, DMSO-d₆) δ; 1.6–1.73 (2H, m), 1.88–2.0 (2H, m), 2.95–3.08 (2H, m), 3.4–3.7 (2H, m), 3.7–3.8 (1H, m), 3.90 (3H, s), 4.74 (2H, d, J=5.6 Hz), 7.27 (1H, d, J=9.2 Hz), 7.79 (1H, dd, J=2.0, 8.8 Hz), 7.87 (1H, d, J=2.0 Hz), 8.24 (1H, d, J=8.4 Hz), 8.47 (1H, dd, J=1.2, 8.4 Hz), 9.38 (1H, s).

EXAMPLE 95

(endo)-4-[(3-Cyano-4-methoxybenzyl)amino]-1-(3-hydroxy-8-azabicyclo[3.2.1]oct-8-yl)-6-phthalazinecarbonitrile Hydrochloride

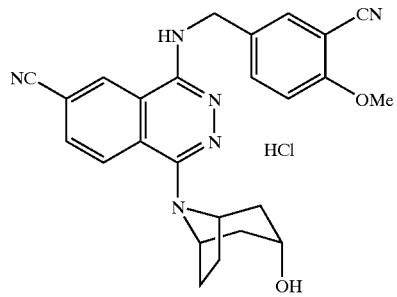

¹H-NMR (400 MHz, DMSO-d₆) δ; 1.9–1.96 (4H, m), 2.17–2.29 (4H, m), 3.91 (3H, s), 4.04 (1H, m), 4.15 (2H, m), 4.68 (2H, s), 7.25 (1H, d, J=8.6 Hz), 7.74 (1H, d, J=8.6 Hz), 7.80 (1H, s), 8.21 (1H, d, J=8.6 Hz), 8.34 (1H, m), 9.07 (1H, m).

EXAMPLE 96

4-[(3-Cyano-4-methoxybenzyl)amino]-1-[3-(hydroxymethyl)tetrahydro-1H-1-pyrrolyl]-6-phthalazinecarbonitrile Hydrochloride

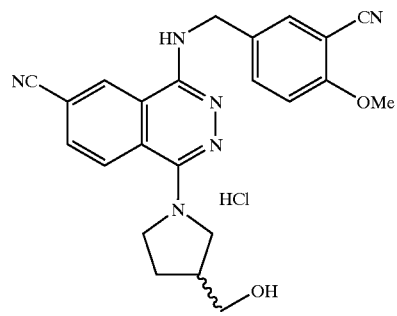

¹H-NMR (400 MHz, DMSO-d₆) δ; 1.84 (1H, m), 2.09 (1H, m), 2.48 (1H, m), 3.40–3.55 (2H, m), 3.64–3.90 (4H, m), 3.91 (3H, s), 4.59 (2H, m), 7.24 (1H, d, J=8.8 Hz), 7.74 (1H, d, J=8.8 Hz), 7.79 (1H, s), 8.42 (1H, d, J=9.3 Hz), 8.70 (1H, m), 9.15 (1H, m).

EXAMPLE 97

4-[(3-Ethyl-4-methoxybenzyl)amino]-1-(4-hydroxypiperidino)-6-phthalazinecarbonitrile Hydrochloride

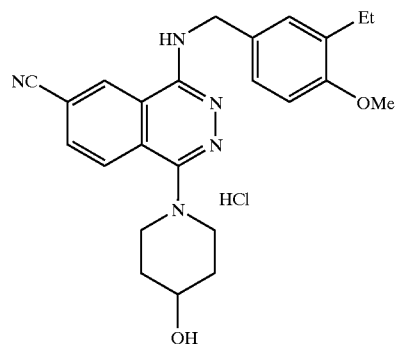

¹H-NMR (400 MHz, DMSO-d₆) δ; 1.14 (3H, t, J=7.5 Hz), 1.63–1.74 (2H, m), 1.90–2.01 (2H, m), 2.57 (2H, q, J=7.5 Hz), 2.97–3.08 (2H, m), 3.40–3.54 (2H, m), 3.75 (1H, m), 3.79 (3H, s), 4.69 (2H, s), 6.95 (1H, d, J=8.2 Hz), 7.26–7.35 (2H, m), 8.25 (1H, d, J=8.6 Hz), 8.48 (1H, dd, J=1.3, 8.6 Hz), 9.44 (1H, m).

EXAMPLE 98

4-[(3-Chloro-4-methoxyphenethyl)amino]-1-(2-hydroxy-7-azaspiro[3.5]non-7-yl)-6-phthalazinecarbonitrile Hydrochloride

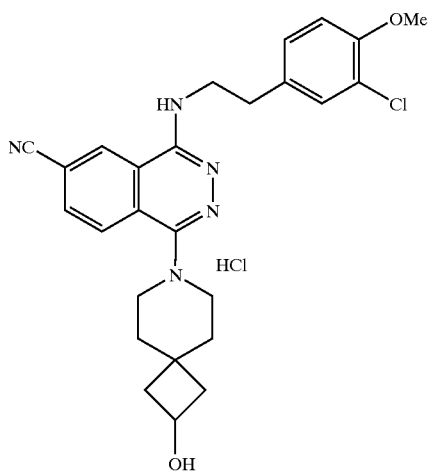

¹H-NMR (400 MHz, DMSO-d₆) δ; 1.58–1.66 (2H, m), 1.67–1.78 (4H, m), 2.14–2.23 (2H, m), 2.92–3.01 (2H, m), 3.07 (2H, s), 3.11 (2H, s), 3.70–3.82 (3H, m), 3.80 (3H, s), 4.08–4.18 (1H, m), 7.06 (1H, d, J=8.4 Hz), 7.26 (1H, dd, J=2.0, 8.4 Hz), 7.43 (1H, d, J=2.0 Hz), 8.19 (1H, d, J=8.4 Hz), 8.44 (1H, dd, J=1.2, 8.4 Hz), 9.55 (1H, s), 10.47 (1H, br-s), 13.9 (1H, br-s).

EXAMPLE 99

4-[(3-Chloro-4-methoxyphenethyl)amino]-1-[4-(2-hydroxyethoxy)piperidino]-6-phthalazinecarbonitrile Hydrochloride

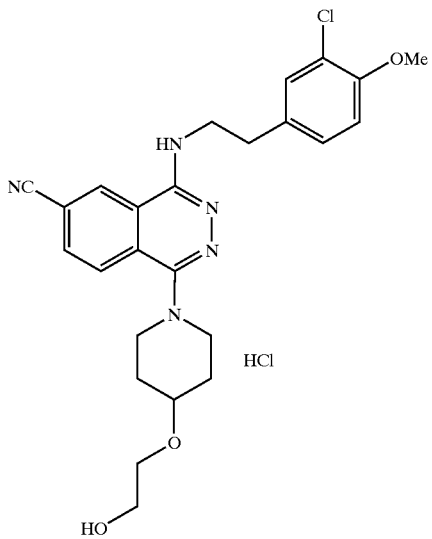

¹H-NMR (400 MHz, DMSO-d₆) δ; 1.68–1.77 (2H, m), 2.00–2.06 (2H, m), 2.76 (2H, t, J=8.0 Hz), 3.03 (2H, t, J=12.0 Hz), 3.32 (10H, m), 3.75 (2H, d, J=8.0 Hz), 3.81 (3H, s), 7.07 (1H, d, J=8.6 Hz), 7.25 (1H, d, J=8.6 Hz), 7.43 (1H, s), 8.24 (1H, d, J=8.6 Hz), 8.45 (1H, d, J=8.6 Hz), 9.32 (1H, s).

EXAMPLE 100

4-[(3-Chloro-4-methoxyphenethyl)amino]-1-[4-fluoro-4-(hydroxymethyl)piperidino]-6-phthalazine Carbonitrile

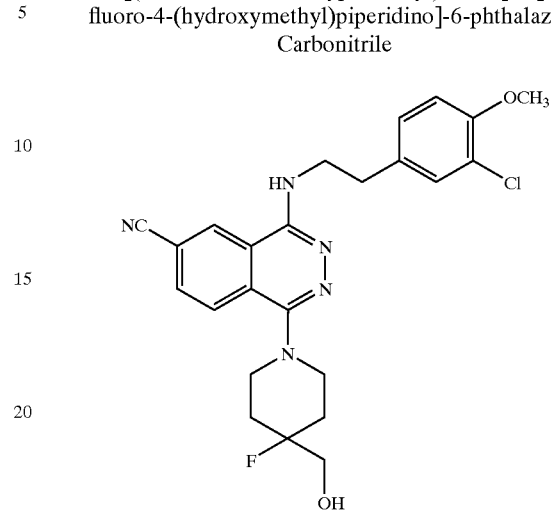

¹H-NMR (400 MHz, DMSO-d₆) δ; 1.82–2.06 (4H, m), 2.83–2.94 (2H, m), 3.04–3.14 (2H, m), 3.24–3.30 (1H, m), 3.49 (2H, dd, J=10.2, 6.0 Hz), 3.54–3.60 (1H, m), 3.64–3.70 (2H, m), 3.80 (3H, s), 5.03 (1H, dd, J=6.0, 6.0 Hz), 7.05 (1H, d, J=12.6 Hz), 7.19 (1H, dd, J=12.6, 2.0 Hz), 7.32 (1H, d, J=2.0 Hz), 7.40–7.45 (1H, m), 8.08 (1H, d, J=8.4 Hz), 8.18 (1H, d, J=8.4 Hz), 8.82 (1H, brs).

EXAMPLE 101

(endo)-4-[(3-Chloro-4-methoxyphenethyl)amino]-1-(3-hydroxy-8-azabicyclo[3.2.1]oct-8-yl)-6-phthalazine Carbonitrile

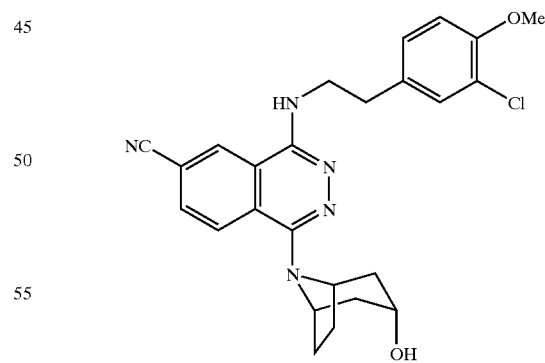

¹H-NMR (400 MHz, DMSO-d₆) δ; 1.78–1.94 (4H, m), 2.14–2.28 (4H, m), 2.92 (2H, t, J=7.0 Hz), 3.67 (2H, q, J=7.0 Hz), 3.82 (3H, s), 4.04 (1H, m), 4.09 (2H, m), 4.49 (1H, d, J=1.8 Hz), 7.06 (1H, d, J=8.4 Hz), 7.20 (1H, dd, J=2.2, 8.4 Hz), 7.27 (1H, m), 7.33 (1H, d, J=2.2 Hz), 8.11 (1H, d, J=8.6 Hz), 8.17 (1H, dd, J=1.5, 8.6 Hz), 8.80 (1H, d, J=1.5 Hz).

EXAMPLE 102

4-[(3-Chloro-4-methoxyphenethyl)amino]-1-[3-(hydroxymethyl)tetrahydro-1H-1-pyrrolyl]-6-phthalazine Carbonitrile

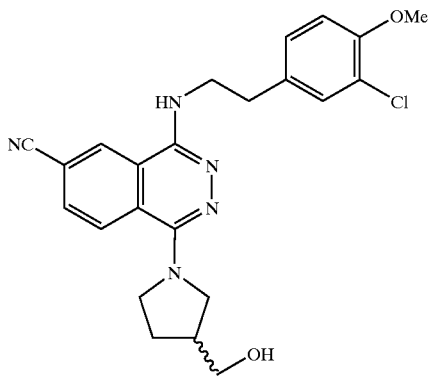

$^1$H-NMR (400 MHz, DMSO-d$_6$) δ; 1.68 (1H, m), 2.00 (1H, m), 2.40 (1H, m), 2.92 (2H, t, J=7.5 Hz), 3.37–3.70 (8H, m), 3.82 (3H, s), 4.69 (1H, d, J=5.3 Hz), 7.06 (1H, d, J=8.6 Hz), 7.16 (1H, m), 7.20 (1H, dd, J=2.0, 8.6 Hz), 7.33 (1H, d, J=2.0 Hz), 8.15 (1H, dd, J=1.3, 8.6 Hz), 8.25 (1H, d, J=8.6 Hz), 8.78 (1H, m).

EXAMPLE 103

4-[(3,4-Dichlorobenzyl)amino]-1-(4-hydroxypiperidino)-6-phthalazinecarbonitrile Hydrochloride

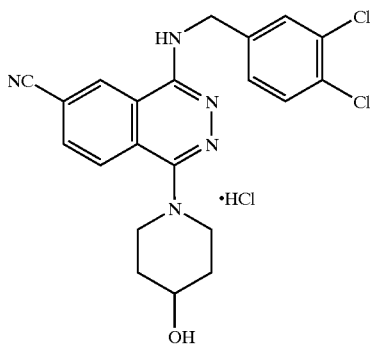

$^1$H-NMR (400 MHz, DMSO-d$_6$) δ; 1.61–1.72 (2H, m), 1.90–2.00 (2H, m), 3.01–3.18 (2H, m), 3.40–3.52 (2H, m), 3.72–3.80 (1H, m), 4.75 (2H, d, J=5.2 Hz), 7.49 (1H, dd, J=8.6, 2.0 Hz), 7.66 (1H, d, J=8.6 Hz), 7.79 (1H, d, J=2.0 Hz), 8.25 (1H, d, J=8.6 Hz), 8.47 (1H, dd, J=8.6, 1.0 Hz), 9.36 (1H, d, J=1.0 Hz), 10.24 (1H, br).

EXAMPLE 104

1-[6-Bromo-4-[(3-chloro-4-methoxybenzyl)amino]-1-phthalazinyl]-4-piperidinol Hydrochloride

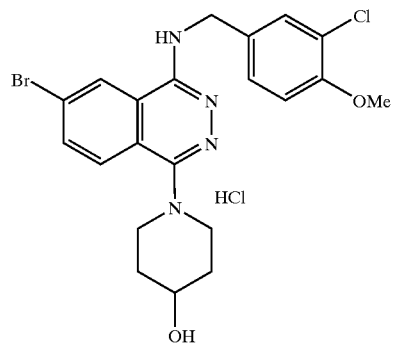

$^1$H-NMR (400 MHz, DMSO-d$_6$) δ; 1.59–1.68 (2H, m), 1.85–1.94 (2H, m), 2.94–3.08 (2H, m), 3.45–3.55 (2H, m), 3.70–3.76 (1H, m), 3.83 (3H, s), 4.69 (2H, d, J=4.8 Hz), 7.14 (1H, d, J=8.4 Hz), 7.44 (1H, d, J=8.4 Hz), 7.59 (1H, s), 8.01 (1H, d, J=8.8 Hz), 8.26 (1H, d, J=8.8 Hz), 9.18 (1H, s).

EXAMPLE 105

1-[4-[(3-Chloro-4-methoxybenzyl)amino]-6-(1H-1-pyrazolyl)-1-phthalazinyl]-4-piperidinol Hydrochloride

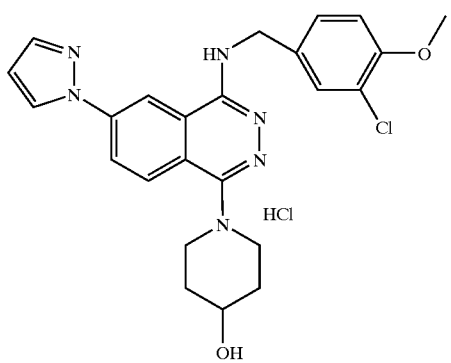

$^1$H-NMR (400 MHz, DMSO-d$_6$) δ; 1.6–1.75 (2H, m), 1.85–2.0 (2H, m), 2.95–3.1 (2H, m), 3.3–3.55 (2H, m), 3.7–3.8 (1H, m), 3.82 (3H, s), 4.68–4.77 (2H, m), 6.72 (1H, m), 7.14 (1H, d, J=8.4 Hz), 7.48 (1H, d, J=7.6 Hz), 7.63 (1H, s), 7.93 (1H, d, J=1.6 Hz), 8.22 (1H, d, J=8.8 Hz), 8.61 (1H, dd, J=1.6, 8.8 Hz), 8.97 (1H, s), 9.46 (1H, m).

EXAMPLE 106

7-[4-[(3-Chloro-4-methoxybenzyl)amino]-6-(1H-1-pyrazolyl)-1-phthalazinyl]-7-azaspiro[3.5]nonan-2-ol Hydrochloride

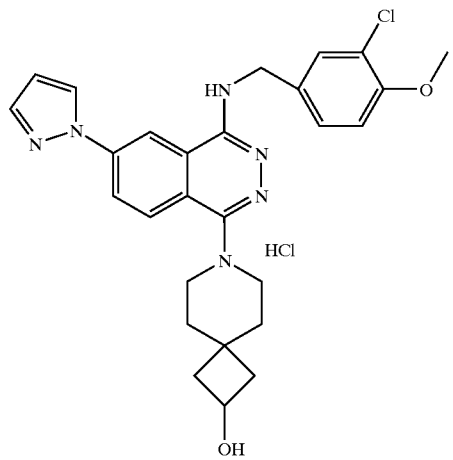

$^1$H-NMR (400 MHz, DMSO-d$_6$) δ; 1.55–1.68 (2H, m), 1.68–1.80 (4H, m), 2.14–2.25 (2H, m), 3.0–3.2 (4H, m), 3.82 (3H, s), 4.14 (1H, hep, J=7.2 Hz), 4.72 (2H, m), 6.72 (1H, t, J=2 Hz), 7.14 (1H, d, J=8.4 Hz), 7.47 (1H, d, J=8.4 Hz), 7.62 (1H, s), 7.93 (1H, d, J=1.6 Hz), 8.20 (1H, d, J=9.2 Hz), 8.60 (1H, dd, J=2.0, 9.2 Hz), 8.94 (1H, d, J=2.4 Hz), 9.43 (1H, s).

EXAMPLE 107

[1-[4-[(3-Chloro-4-methoxybenzyl)amino]-6-(1H-1-pyrazolyl)-1-phthalazinyl]-4-fluoro-4-piperidinyl] methanol Hydrochloride

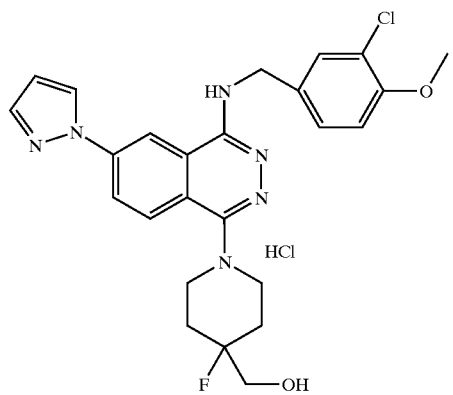

$^1$H-NMR (400 MHz, DMSO-d$_6$) δ; 1.85–2.0 (2H, m), 1.95–2.1 (2H, m), 3.05–3.2 (2H, m), 3.4–3.6 (2H, m), 3.51 (2H, d, J=2.0 Hz), 3.83 (3H, s), 4.74 (2H, d, J=5.2 Hz), 6.72 (1H, t, J=1.6 Hz), 7.14 (1H, d, J=8.8 Hz), 7.48 (1H, d, J=8.4 Hz), 7.64 (1H, s), 7.93 (1H, d, J=1.6 Hz), 8.25 (1H, d, J=9.2 Hz), 8.61 (1H, dd, J=2.0, 9.2 Hz), 8.95 (1H, s), 9.44 (1H, S).

EXAMPLE 108

1-[4-[(3-Bromo-4-methoxybenzyl)amino]-6-(1H-1-pyrazolyl)-1-phthalazinyl]-4-piperidinol Hydrochloride

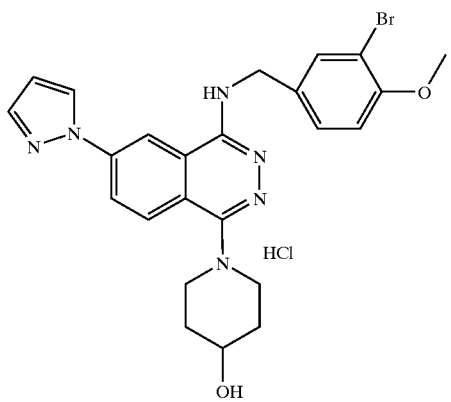

$^1$H-NMR (400 MHz, DMSO-d$_6$) δ; 1.6–1.74 (2H, m), 1.87–2.0 (2H, m), 2.9–3.1 (2H, m), 3.4–3.55 (2H, m), 3.7–3.8 (1H, m), 3.81 (3H, s), 4.65–4.8 (2H, m), 6.72 (1H, m), 7.10 (1H, d, J=8.8 Hz), 7.53 (1H, d, J=8.0 Hz), 7.79 (1H, s), 7.93 (1H, d, J=1.2 Hz), 8.21 (1H, d, J=8.8 Hz), 8.61 (1H, d, J=8.8 Hz), 9.00 (1H, d, J=2.8 Hz), 9.51 (1H, s).

EXAMPLE 109

1-[4-[(3-Chloro-4-methoxybenzyl)amino]-6-(1H-1,2,3-triazol-1-yl)-1-phthalazinyl]-4-piperidinol Hydrochloride

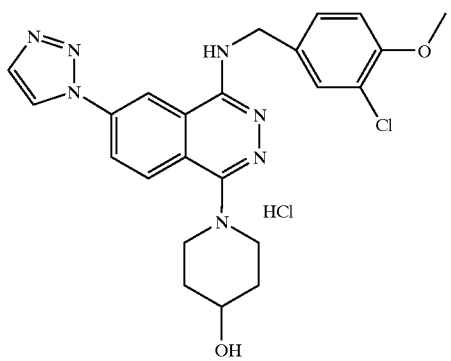

$^1$H-NMR (400 MHz, DMSO-d$_6$) δ; 1.62–1.75 (2H, m), 1.9–2.0 (2H, m), 3.0–3.1 (2H, m), 3.3–3.58 (2H, m), 3.7–3.8 (1H, m), 3.83 (3H, s), 4.73 (2H, d, J=5.6 Hz), 7.15 (1H, d, J=8.8 Hz), 7.46 (1H, d, J=8.4 Hz), 7.62 (1H, s), 8.13 (1H, m), 8.32 (1H, d, J=8.8 Hz), 8.68 (1H, d, J=9.2 Hz), 9.17 (1H, s), 9.56 (1H, s).

EXAMPLE 110

4-[(3-Chloro-4-methoxybenzyl)amino]-1-(4-hydroxypiperidino)-6-phthalazinecarbaldehyde O6-Methyloxime Hydrochloride

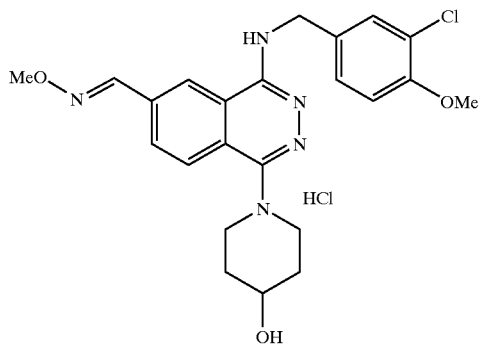

$^1$H-NMR (400 MHz, DMSO-d$_6$) δ; 1.60–1.70 (2H, m), 1.87–1.70 (2H, m), 2.96–3.05 (2H, m), 3.30–3.50 (2H, m), 3.68–3.78 (1H, m), 3.83 (3H, s), 3.99 (3H, s), 4.66–4.73 (2H, m), 7.14 (1H, d, J=8 Hz), 7.42 (1H, dd, J=2, 8 Hz), 7.57 (1H, d, J=2 Hz), 8.13 (1H, d, J=8 Hz), 8.28 (1H, d, J=8 Hz), 8.39 (1H, s), 8.94 (1H, br-s).

EXAMPLE 111

4-[(3-Chloro-4-methoxybenzyl)amino]-1-(4-hydroxypiperidino)-6-phthalazinecarbaldehyde O6-Ethyloxime Hydrochloride

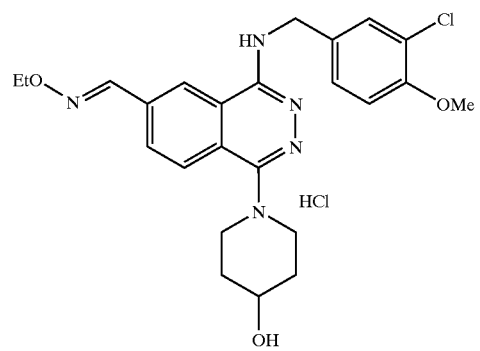

$^1$H-NMR (400 MHz, DMSO-d$_6$) δ; 1.28 (3H, t, J=6 Hz), 1.60–1.73 (2H, m), 1.87–1.98 (2H, m), 2.94–3.06 (2H, m), 3.39–3.52 (2H, m), 3.68–3.78 (1H, m), 3.83 (3H, s), 4.25 (2H, q, J=6 Hz), 4.67–4.74 (2H, m), 7.13 (1H, d, J=9 Hz), 7.42 (1H, d, J=9 Hz), 7.58 (1H, s), 8.13 (1H, d, J=8 Hz), 8.30 (1H, d, J=8 Hz), 8.39 (1H, s), 8.97 (1H, s).

EXAMPLE 112

4-[(3-Chloro-4-methoxybenzyl)amino]-1-(4-hydroxypiperidino)-6-phthalazinecarbaldehyde O6-Benzyloxime Hydrochloride

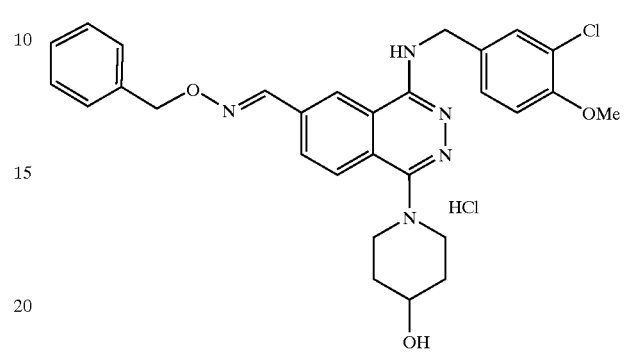

$^1$H-NMR (400 MHz, DMSO-d$_6$) δ; 1.59–1.71 (2H, m), 1.87–1.96 (2H, m), 2.94–3.05 (2H, m), 3.37–3.51 (2H, m), 3.68–3.78 (1H, m), 3.82 (3H, s), 4.67–4.76 (2H, m), 5.27 (2H, s), 7.13 (1H, d, J=9 Hz), 7.29–7.48 (6H, m), 7.59 (1H, s), 8.12 (1H, d, J=9 Hz), 8.29 (1H, d, J=9 Hz), 8.45 (1H, s), 9.04 (1H, br-s).

EXAMPLE 113

4-[(3-Chloro-4-methoxybenzyl)amino]-1-[3-fluoro-3-(hydroxymethyl)tetrahydro-1H-1-pyrrolyl]-6-phthalazinecarbonitrile Hydrochloride

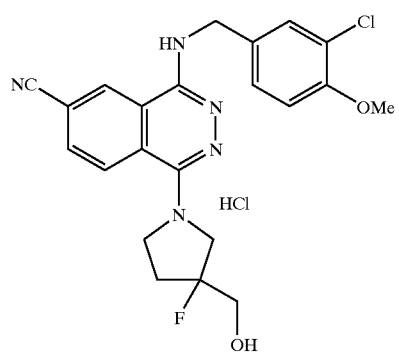

$^1$H-NMR (400 MHz, DMSO-d$_6$) δ; 2.09–2.28 (2H, m), 3.50–4.05 (6H, m), 3.81 (3H, s), 4.66 (2H, s), 7.11 (1H, d, J=8.0 Hz), 7.43 (1H, d, J=8.0 Hz), 7.58 (1H, s), 8.43 (1H, d, J=8.4 Hz), 8.53 (1H, s), 9.45 (1H, s).

EXAMPLE 114

4-[(3-Chloro-4-methoxybenzyl)amino]-1-(3-hydroxy-1-oxa-8-azaspiro[4.5]deca-8-yl)-6-phthalazinecarbonitrile Hydrochloride

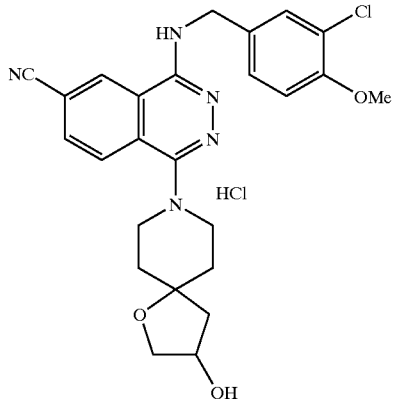

¹H-NMR (400 MHz, DMSO-d₆) δ; 1.65–1.85 (3H, m), 1.87–2.01 (2H, m), 3.16–3.63 (8H, m), 3.82 (3H, s), 4.32 (1H, s), 4.73 (2H, d, J=4.8 Hz), 7.13 (1H, d, J=8.4 Hz), 7.48 (1H, d, J=8.0 Hz), 7.62 (1H, s), 8.23 (1H, d, J=8.0 Hz), 8.44 (1H, d, J=8.0 Hz), 9.57 (1H, s), 10.78 (1H, s).

EXAMPLE 115

4-[(3-Chloro-4-methoxybenzyl)amino]-1-[2-(1-hydroxycyclopentyl)-1-ethynyl]-6-phthalazine Carbonitrile

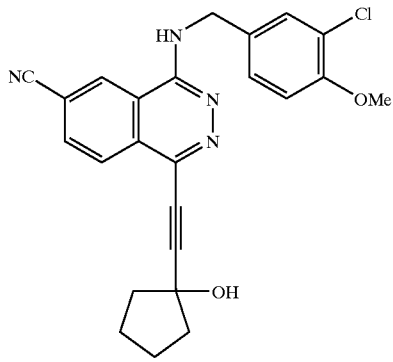

¹H-NMR (400 MHz, DMSO-d₆) δ; 1.69–1.86 (4H, m), 1.97–2.04 (4H, m), 3.82 (3H, s), 4.75 (2H, d, J=5.4 Hz), 5.60 (1H, s), 7.10 (1H, d, J=8.8 Hz), 7.36 (1H, dd, J=8.8, 1.2 Hz), 7.49 (1H, d, J=1.2 Hz), 8.19 (1H, d, J=8.8 Hz), 8.31 (1H, dd, J=8.8, 0.6 Hz), 8.52 (1H, t, J=5.4 Hz), 8.97 (1H, d, J=0.6 Hz).

EXAMPLE 116

4-[(3-Chloro-4-methoxybenzyl)amino]-1-[2-(1-hydroxycyclopentyl)ethyl]-6-phthalazinecarbonitrile Hydrochloride

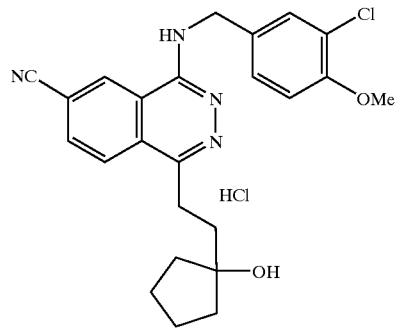

690 mg of 4-[(3-chloro-4-methoxybenzyl)amino]-1-[2-(1-hydroxycyclopentyl)-1-ethynyl]-6-phthalazine carbonitrile was dissolved in 200 ml tetrahydrofuran, 50 mg of 10% Pd—C was added thereto, and the mixture was stirred for 0.5 hr in a hydrogen atmosphere. The reaction solution was filtered through Celite, and the filtrate was evaporated. The resulitng residue was purified by silica gel column chromatography to give 400 mg of 4-[(3-chloro-4-methoxybenzyl)amino]-1-[2-(1-hydroxycyclopentyl)ethyl]-6-phthalazine carbonitrile. This product was converted in a usual manner into the hydrochloride.

¹H-NMR (400 MHz, DMSO-d₆) δ; 1.47–1.78 (8H, m), 1.89–1.94 (2H, m), 3.24–3.33 (2H, m), 3.84 (3H, s), 4.74 (2H, d, J=4.4 Hz), 7.15 (1H, d, J=8.4 Hz), 7.45 (1H, dd, J=8.4, 2.0 Hz), 7.60 (1H, d, J=2.0 Hz), 8.46 (1H, d, J=8.8 Hz), 8.55 (1H, dd, J=8.8, 1.2 Hz), 9.40 (1H, br).

The following compounds were obtained in the same manner.

EXAMPLE 117

4-[(3-Chloro-4-methoxybenzyl)amino]-1-(3-hydroxy-3-methylbutyl)-6-phthalazinecarbonitrile Hydrochloride

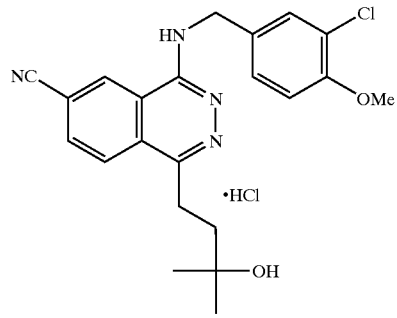

¹H-NMR (400 MHz, DMSO-d₆) δ; 1.17 (6H, s), 1.73–1.80 (2H, m), 3.17–3.24 (2H, m), 3.80 (3H, s), 4.78 (2H, d, J=4.4 Hz), 7.10 (1H, d, J=8.4 Hz), 7.48 (1H, dd, J=8.4, 1.8 Hz), 7.62 (1H, d, J=1.8 Hz), 8.43 (1H, d, J=8.6 Hz), 8.51 (1H, dd, J=8.6, 1.2 Hz), 9.63 (1H, br), 10.30 (1H, br).

EXAMPLE 118

1-(3-Amino-3-methylbutyl)-4-[(3-chloro-4-methoxybenzyl)amino]-6-phthalazinecarbonitrile Dihydrochloride

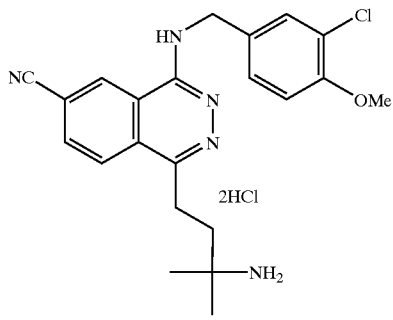

$^1$H-NMR (400 MHz, DMSO-d$_6$) δ; 1.37 (6H, s), 2.00–2.19 (2H, m), 3.21–3.56 (2H, m), 3.84 (3H, s), 4.78 (2H, d, J=4.4 Hz), 7.15 (1H, d, J=8.4 Hz), 7.46 (1H, d, J=8.4 Hz), 7.61 (1H, s), 8.15–8.29 (4H, m), 8.48 (1H, d, J=8.8 Hz), 8.56 (1H, d, J=8.8 Hz), 9.38 (1H, br).

EXAMPLE 119

4-[(3-Chloro-4-methoxybenzyl)amino]-1-[3-(dimethylamino)propyl]-6-phthalazinecarbonitrile Dihydrochloride

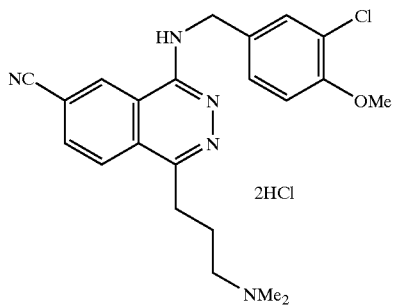

$^1$H-NMR (400 MHz, DMSO-d$_6$) δ; 2.11–2.19 (2H, m), 2.74 (3H, s), 2.75 (3H, s), 3.16–3.29 (4H, m), 3.85 (3H, s), 4.80 (2H, d, J=5.2 Hz), 7.16 (1H, d, J=8.4 Hz), 7.48 (1H, dd, J=8.4, 2.0 Hz), 7.63 (1H, d, J=2.0 Hz), 8.49 (1H, d, J=8.4 Hz), 8.56 (1H, dd, J=8.4, 1.4 Hz), 9.47 (1H, d, J=1.4 Hz), 10.56 (2H, br).

What is claimed is:

1. A phthalazine compound represented by the formula (I), a pharmacologically acceptable salt thereof or a hydrate thereof:

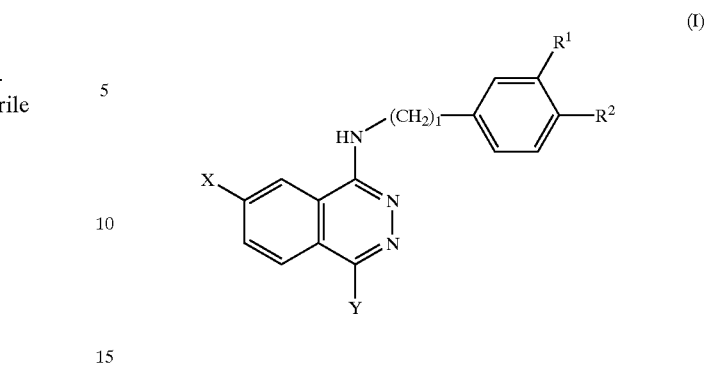

wherein $R^1$ and $R^2$ are the same as or different from each other and represent a halogen atom, a C1 to C4 alkyl group which may be substituted with a halogen atom, a hydroxyl group, a C1 to C4 alkoxy group which may be substituted with a halogen atom or a cyano group; l is an integer of 1 to 3;

X represents a cyano group, a nitro group, a halogen atom, a thiocarbamoyl group, a hydroxyimino group which may be substituted with a C1 to C4 alkyl group, a phenyl C1 to C4 alkyl group or a carboxy C1 to C4 alkyl group, or a heteroaryl group selected from the group consisting of pyrrole, pyrazole, imidazole, triazole, tetrazole, thiazole, isothiazole, thiadiazole, pyridine, pyrimidine, and triazine, said heteroaryl group optionally substituted with 1 to 3 substituents selected from the group consisting of C1 to C4 alkyl group which may be substituted with a halogen atom, a cyano group, a nitro group or a hydroxyl group; a C1 to C4 alkoxy group which may be substituted with a halogen atom, a cyano group, a nitro group or a hydroxyl group; a cyano group; a nitro group; a carboxyl group which may have a protective group which can be degraded by any means in vivo to form a carboxylic acid; a hydroxyl group which may have a protective group which can be degraded by any means in vivo to form a hydroxyl group; a carbamoyl group which may be substituted with a lower alkyl group; a halogen atom; and an amino group which may be substituted with a C1 to C4 acyl group, a C1 to C4 alkylsulfonyl group or a phenylsulfonyl group;

Y represents:

i) a group represented by the formula (III):

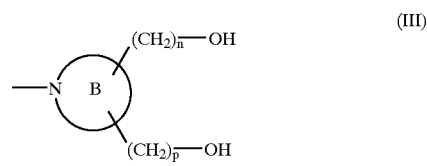

wherein ring B represents a 5- to 6-memberred amine ring which may have a double bond, and n and p are the same as or different from each other and represent an integer of 0 or 1 to 3; or ii) a group represented by the formula (IV):

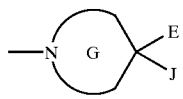

wherein ring G represents a 5- to 6-memberred amine ring which may have a double bond, E represents a hydroxyl group, a halogen atom, a C1 to C4 alkyl group or a C1 to C4 alkoxy group, J is represented by the formula —(CHR$^4$)q—Q wherein R$^4$ represents a hydrogen atom or a C1 to C4 alkyl group, Q represents a hydroxyl group, a halogen atom, a carboxyl group which may have a protective group which can be degraded by any means in vivo to form a carboxyl group, a carbamoyl group or an azolyl group not containing a heteroatom other than a nitrogen atom, q is an integer of 0 or 1 to 4; or E and J may form a 3- to 6-memberred ring together with the carbon atom to which they are bound, and the ring optionally having an oxygen or nitrogen atom and optionally having a substituent group selected from the group consisting of hydroxyl group, carboxyl group which may have a protective group which can be degraded by any means in vivo to form a carboxyl group, C1–C4 alkyl group, C1–C4 alkyl group substituted with a hydroxyl group, oxo group, and halogen group;

provided that the following compounds are excluded:

the compound wherein l is 1, E and Q are hydroxyl groups, and q is 0; the compound where l is 1, ring B is a 5- or 6-memberred amine ring, and both n and p are 0; and the compound wherein l is 1, q is 0, and E is a C1 to C2 alkyl group and Q is a hydroxyl group.

2. The phthalazine compound as claimed in claim 1, wherein R$^1$ is a halogen atom, a C1 to C4 alkyl group which may be substituted with a halogen atom, or a cyano group, and R$^2$ is a halogen atom, a hydroxyl group or a C1 to C4 alkoxy group, a pharmacologically acceptable salt thereof or a hydrate thereof.

3. The phthalazine compound as claimed in claim 1 or 2, wherein Y is represented by the formula (III):

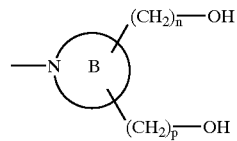

wherein ring B, n and p have the same meanings as defined in claim 1, a pharmacologically acceptable salt thereof or a hydrate thereof.

4. The phthalazine compound as claimed in claim 1 or 2, wherein Y is represented by the formula (IV):

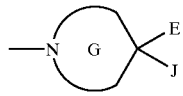

wherein ring G, E and J have the same meanings as defined in claim 1, a pharmacologically acceptable salt thereof or a hydrate thereof.

5. The phthalazine compound as claimed in claim 1 or 2, wherein Y is the group represented by the formula (III), ring B is a 6-memberred amino ring, n is 0 or 1 and p is 1, a pharmacologically acceptable salt thereof or a hydrate thereof.

6. The phthalazine compound as claimed in claim 1 or 2, a pharmacologically acceptable salt thereof or a hydrate thereof, wherein Y is the group represented by the formula (IV), E and J form a 3- to 6-memberred ring which may have an oxygen or nitrogen atom and may have a substituent group together with the carbon atom to which they are bound, and ring G is a 4- to 8-memberred amine ring which may have a double bond.

7. The phthalazine compound as claimed in claim 1 or 2, wherein Y is the group represented by the formula (IV), E is a hydroxyl group, a halogen atom, a C1 to C4 alkyl group or a C1 to C4 alkoxy group, J is represented by the formula —(CHR$^4$)q—Q, wherein R$^4$ is a hydrogen atom or a C1 to C4 alkyl group, Q is a hydroxyl group, a halogen atom, a carboxyl group which may have a protective group, a carbamoyl group or an azolyl group not containing a heteroatom other than a nitrogen atom, q is an integer of 0 or 1 to 4; and ring G is a 5- to 6-memberred amine ring which may have a double bond, a pharmacologically acceptable salt or a hydrate thereof.

8. The phthalazine compound as claimed in claim 1, wherein the compound is selected from the following group, a pharmacologically acceptable salt or a hydrate thereof:

1) 4-[(3-chloro-4-methoxybenzyl)amino]-1-[(4-hydroxy-4-hydroxymethyl)piperidino]-6-phthalazine carbonitrile;

2) 4-[(3-chloro-4-methoxybenzyl)amino]-1-(2-hydroxy-7-azaspiro[3.5]non-7-yl)-6-phthalazine carbonitrile;

3) 4-[(3-chloro-4-methoxyphenethyl)amino]-1-(2-hydroxy-7-azaspiro[3.5]non-7-yl)-6-phthalazine carbonitrile;

4) 4-[(3-bromo-4-methoxybenzyl)amino]-1-(2-hydroxy-7-azaspiro[3.5]non-7-yl)-6-phthalazine carbonitrile;

5) 4-[(3-chloro-4-methoxybenzyl)amino]-1-(2-hydroxy-6-azaspiro[3.4]oct-6-yl)-6-phthalazine carbonitrile;

6) 4-[(3-chloro-4-methoxybenzyl)amino]-1-[4-(1-fluoro-2-hydroxyethyl)piperidino]-6-phthalazine carbonitrile;

7) 4-[(3-chloro-4-methoxybenzyl)amino]-1-[4-fluoro-4-(hydroxymethyl)piperidino]-6-phthalazine carbonitrile;

8) 4-[(3-chloro-4-methoxybenzyl)amino]-1-[4-(hydroxymethyl)-4-methoxypiperidino]-6-phthalazine carbonitrile;

9) 1-[4-fluoro-4-(hydroxymethyl)piperidino]-4-[(4-methoxy-3-methylbenzyl)amino]-6-phthalazine carbonitrile; and 10) 4-[(3-chloro-4-methoxybenzyl)amino]-1-[4-(fluoromethyl)-4-hydroxypiperidino]-6-phthalazine carbonitrile.

9. The phthalazine compound as claimed in claim 1 or 2, wherein E and J form a 3- to 6-memberred ring together with the carbon atom to which they are bound, and the ring optionally having an oxygen or nitrogen atom and being optionally substituted with a substituent selected from the group consisting of hydroxyl group, carboxyl group which may have a protective group, C1–C4 alkyl group, C1–C4 alkyl group substituted with a hydroxyl group, oxo group, and halogen group.

10. The phthalazine compound of claim 1 or 2, wherein said protective group for said carboxylic acid consists of an optionally halogenated straight or branched chain C1–4 alkyl.

11. The phthalazine compound of claim 10, wherein said protective group is selected from the group consisting of methyl, ethyl, isopropyl, t-butyl, 2-iodo-ethyl and 2,2,2-trichloroethyl.

12. The phthalazine compound of claim 1, wherein said protective group for the carboxyl group is selected from the group consisting of lower alkyl group, p-methoxybenzyl, p-nitrobenzyl, 3,4-dimethoxybenzyl, diphenylmethyl, trityl, phenethyl, halogenated lower alkyl group, lower alkanoyloxy lower alkyl group, higher alkanoyloxy lower alkyl group, lower alkoxycarbonyloxy lower alkyl group, carboxy lower alkyl group, 3-phthalidyl, 4-glycyloxybenzoyloxymethyl, (5-methyl-2-oxo-1,3-dioxolene-4-yl)methyl, 1-cyclohexylacetyloxyethyl, and cycloalkyloxycarbonyloxy lower alkyl group.

13. The phthalazine compound of claim 1, wherein said protective group for the hydroxyl group is selected from the group consisting of acyl group, acetyl group, benzoyl group, and lower alkoxymethyl group.

14. The phthalazine compound of claim 1 or 2, wherein said ring formed by E and J together with the carbon atom to which they are bound is selected from the group consisting of cyclobutane, cyclopentane, cyclohexane, oxirane, tetrahydrofuran, tetrahydropyran, butyrolactone and butyrolactam.

15. The phthalazine compound of claim 1, wherein X represents a cyano group, and ring G represents a 5- to 6-memberred amine ring which may have a double bond.

16. A phthalazine compound represented by the formula (I), a pharmacologically acceptable salt thereof or a hydrate thereof:

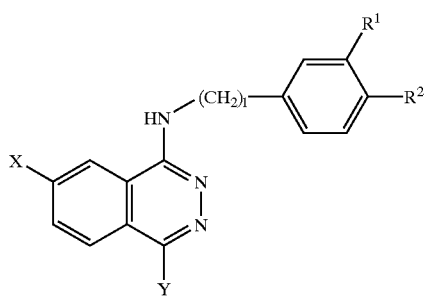

wherein $R^1$ and $R^2$ are the same as or different from each other and represent a halogen atom, a C1 to C4 alkyl group which may be substituted with a halogen atom, a hydroxyl group, a C1 to C4 alkoxy group which may be substituted with a halogen atom or a cyano group; l is an integer of 1 to 3;

X represents a cyano group, a nitro group, a halogen atom, a thiocarbamoyl group, a hydroxyimino group which may be substituted with a C1 to C4 alkyl group, a phenyl C1 to C4 alkyl group or a carboxy C1 to C4 alkyl group, or a heteroaryl group selected from the group consisting of pyrrole, pyrazole, imidazole, triazole, tetrazole, thiazole, isothiazole, pyridine, pyrimidine, triazine and thiadiazole, said heteroaryl group optionally substituted with 1 to 3 substituents selected from the group consisting of C1 to C4 alkyl group which may be substituted with a halogen atom, a cyano group, a nitro group or a hydroxyl group; a C1 to C4 alkoxy group which may be substituted with a halogen atom, a cyano group, a nitro group or a hydroxyl group; a cyano group; a nitro group; a carboxyl group which may be protected by any group which can be degraded by any means in vivo to form the carboxylic acid; a hydroxyl group which may be protected by any group which can be degraded by any means in vivo to form the hydroxyl group; a carbamoyl group which may be substituted with a lower alkyl group; a halogen atom; and an amino group which may be substituted with a C1 to C4 acyl group, a C1 to C4 alkylsulfonyl group or a phenylsulfonyl group;

Y represents a group represented by the formula (IV):

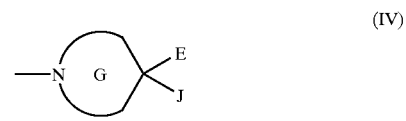

(IV)

wherein ring G represents a 5- to 6-memberred amine ring which may have a double bond; E and J form a 3- to 6-memberred carbocyclic ring together with the carbon atom to which they are bound, and the ring optionally having an oxygen or nitrogen atom and optionally having a substituent group selected from the group consisting of hydroxyl group, carboxyl group which may be protected by any group which can be degraded by any means in vivo to form the carboxyl group, C1–C4 alkyl group, C1–C4 alkyl group substituted with a hydroxyl group, oxo group, and halogen group.

17. A pharmaceutical composition comprising a pharmacologically effective dose of the phthalazine compound as claimed in claim 1, a pharmacologically acceptable salt thereof or a hydrate thereof, and a pharmacologically acceptable carrier.

18. The pharmaceutical composition as claimed in claim 1, wherein the phthalazine compound is selected from the following group consisting of:

1) 4-(3-chloro-4-methoxybenzyl)amino-6-cyano-1-(3,4-dihydroxypiperidino)phthalazine;
2) 4-(3-chloro-4-methoxybenzyl)amino-6-cyano-1-(4-hydroxy-4-hydroxymethylpiperidino)phthalazine;

3) 4-(3-chloro-4-methoxybenzyl)amino-6-cyano-1-(4,4-di-hydroxymethylpiperidino)phthalazine; and
4) 4-(3-chloro-4-methoxybenzyl)amino-6-cyano-1-(3,4-dihydroxypyrrolidino)phthalazine.

19. A method for treating erectile dysfunction, which comprises the step of administering a pharmacologically effective dose of the phthalazine compound as claimed in claim 1, a pharmacologically acceptable salt thereof or a hydrate thereof to a patient suffering from erectile dysfunction.

20. A method for treating erectile dysfunction, which comprises the step of administering a pharmacologically effective dose of the phthalazine compound as claimed in claim 8, a pharmacologically acceptable salt thereof or a hydrate thereof to a patient suffering from erectile dysfunction.

* * * * *